US008288517B2

(12) United States Patent
Clarkson et al.

(10) Patent No.: US 8,288,517 B2
(45) Date of Patent: Oct. 16, 2012

(54) ACID FUNGAL PROTEASES

(75) Inventors: Kathleen A. Clarkson, San Francisco, CA (US); Nigel Dunn-Coleman, El Sauzal (ES); Suzanne E. Lantz, San Carlos, CA (US); Craig E. Pilgrim, Roscoe, IL (US); Piet van Solingen, Naaldwijk (NL); Michael Ward, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/441,731

(22) Filed: Apr. 6, 2012

(65) Prior Publication Data
US 2012/0225469 A1 Sep. 6, 2012

Related U.S. Application Data

(60) Division of application No. 12/582,606, filed on Oct. 20, 2009, now Pat. No. 8,173,409, which is a continuation of application No. 12/167,092, filed on Jul. 2, 2008, now Pat. No. 7,629,451, which is a continuation of application No. 11/312,290, filed on Dec. 20, 2005, now Pat. No. 7,429,476.

(60) Provisional application No. 60/648,233, filed on Jan. 27, 2005, provisional application No. 60/640,399, filed on Dec. 30, 2004.

(51) Int. Cl.
*C12N 15/57* (2006.01)
*C12N 15/80* (2006.01)
*C12N 9/58* (2006.01)

(52) U.S. Cl. . 536/23.2; 435/69.1; 435/223; 435/254.11; 435/254.6

(58) Field of Classification Search .................. None
See application file for complete search history.

(56) References Cited

U.S. PATENT DOCUMENTS

| 4,473,644 | A | 9/1984 | Schindler et al. |
| 4,518,697 | A | 5/1985 | Bartnik et al. |
| 4,533,359 | A | 8/1985 | Kondo et al. |
| 4,683,195 | A | 7/1987 | Mullis et al. |
| 5,231,017 | A | 7/1993 | Lantero et al. |
| 5,874,276 | A | 2/1999 | Fowler et al. |
| 6,017,762 | A | 1/2000 | Jara et al. |
| 6,022,725 | A | 2/2000 | Fowler et al. |
| 6,255,515 | B1 | 7/2001 | Kato et al. |

(Continued)

FOREIGN PATENT DOCUMENTS
AU 21749/95 1/1996
(Continued)

OTHER PUBLICATIONS

Brigidi, P., et al., "Genetic transformation of intact cells of *Bacillus subtilis* by electroporation." *FEMS Microbiol. Lett.* 67: 135-138, 1990.

(Continued)

*Primary Examiner* — Manjunath Rao
*Assistant Examiner* — William W Moore
(74) *Attorney, Agent, or Firm* — Danisco US Inc.

(57) ABSTRACT

The present invention is directed to novel acid proteases and more specifically to NSP24 family proteases and NSP25 family proteases including biologically active fragments thereof and to nucleic acid molecules encoding said proteases. Also provided are vectors and host cells including nucleic acid sequences coding for the proteases, methods for producing the proteases, enzyme compositions and methods employing said proteases.

10 Claims, 15 Drawing Sheets

U.S. PATENT DOCUMENTS

Figure 1:
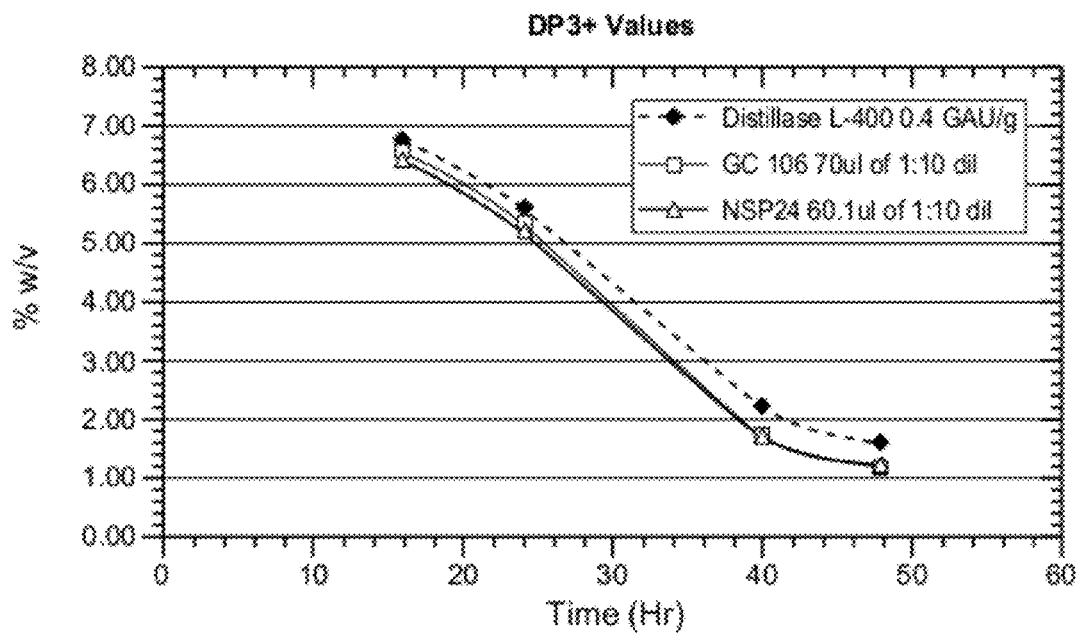
Figure 2:
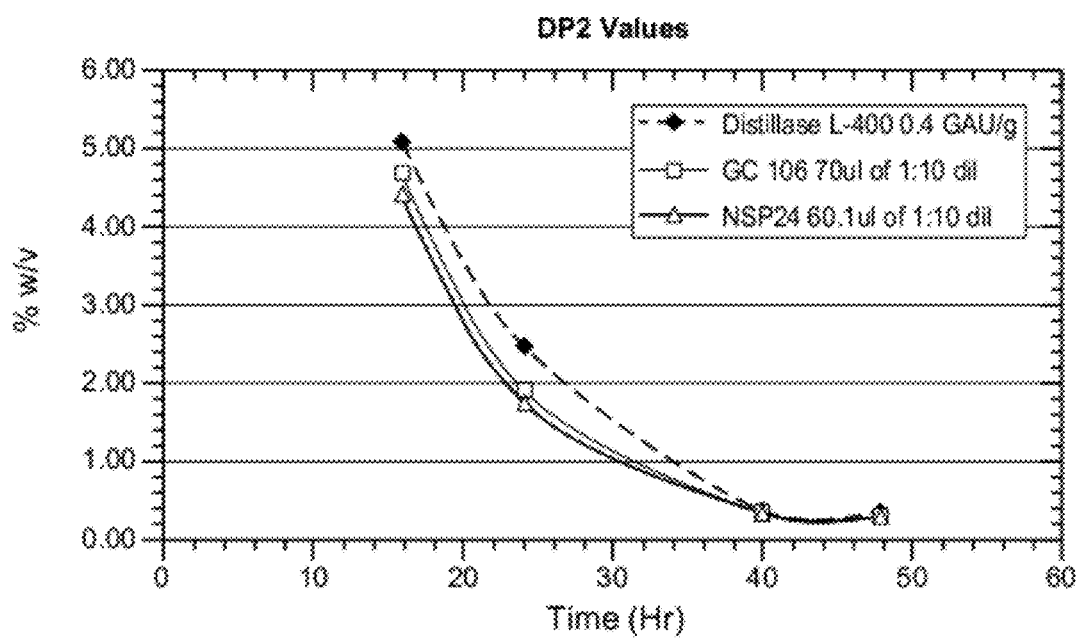
Figure 3:
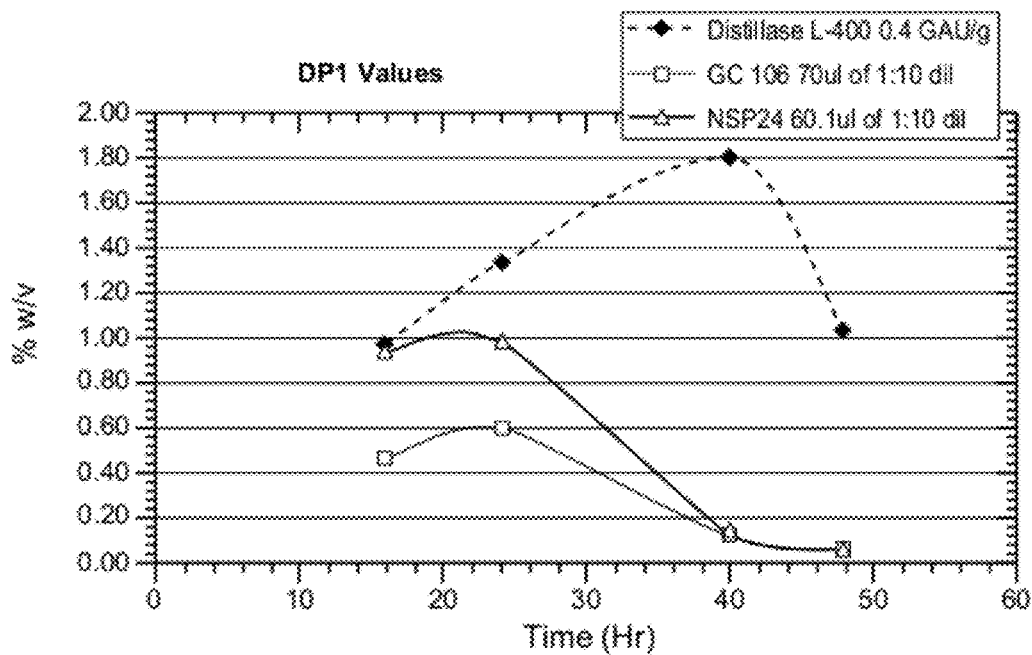
Figure 4:
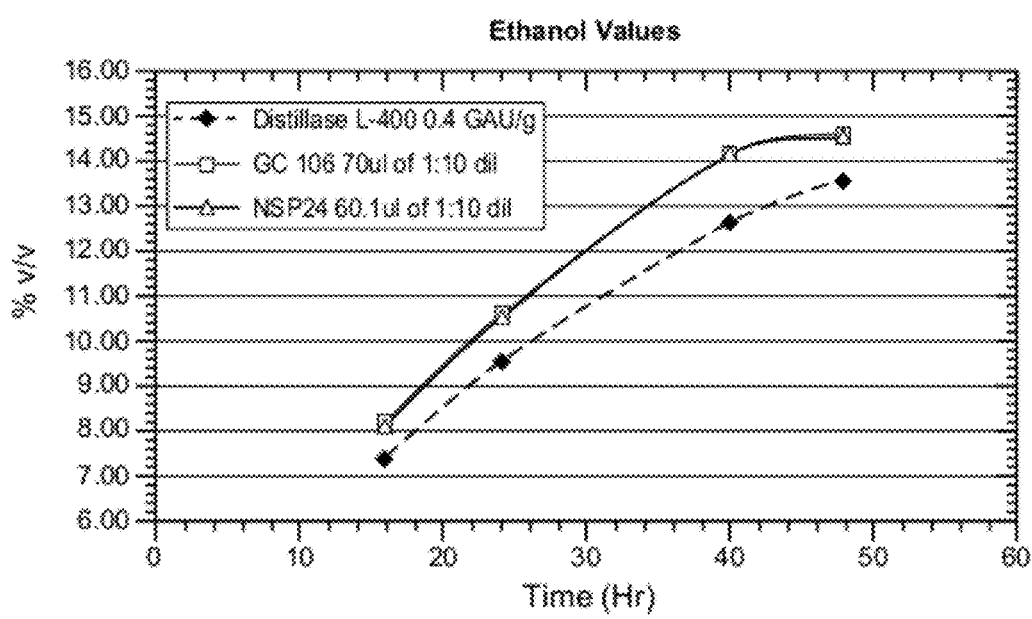

| | | |
|---|---|---|
| 6,268,328 B1 | 7/2001 | Mitchinson et al. |
| 6,605,458 B1 | 8/2003 | Hansen et al. |
| 6,768,001 B2 | 7/2004 | Saloheimo et al. |
| 2006/0154353 A1 | 7/2006 | Duan et al. |

FOREIGN PATENT DOCUMENTS

| | | |
|---|---|---|
| EP | 0 215 594 A2 | 3/1987 |
| EP | 0 134 267 A1 | 3/1995 |
| JP | 01240184 | 9/1989 |
| WO | WO 90/00192 | 1/1990 |
| WO | WO 90/10072 | 9/1990 |
| WO | WO 99/34011 | 7/1999 |

OTHER PUBLICATIONS

Altschul, S. F., et al., "Basic Local Alignment Search Tool." *J. Mol. Biol.*, 215:403-410, 1990.

Bajar, A., et al., "Identification of a fungal cutinase promoter that is inducible by a plant signal via a phosphorylated trans-acting factor," *Proc. Natl. Acad. Sci. USA* 88 : 8208-8212, 1991.

Berka, R.M. et al., "Isolation and characterization of the *Aspergillus oryzae* gene encoding aspergillopepsin O." *Gene* 125: 195-198, 1993.

Berka, R.M., et al. , "Molecular Cloning and Deletion of the Gene Encoding Aspergillopepsin A from *Aspergillus-awamori*." *Gene* 86(2) : 153-162, 1990.

Boel, E., et al., "Two different types of intervening sequences in the glucoamylase gene from *Aspergillus niger*." *The EMBO Journal* 3(7): 1581-1585, 1984.

Clegg, K.M., "Dietary Enzymatic Hydrolysates of Protein." In *Biochemical Aspects of New Protein Food*, J, Adler-Nissen, et al., eds., pp.109-117, Pergamon, Oxford, 1978.

Database EMBL, Dec. 3, 2000, "*Trichoderma harzianum* proA gene for putative aspartate protease," retrieved from EBI accession No. EM_PRO :AJ276388—UNIPROT:Q9HDT6.

Database Uniprot Oct. 25, 2004, Aspartyl protease,UNIPROT; Q641D0.

Davis, R.H., et al., "Genetic and Microbiological Research Techniques for *Neurospora crassa*." *Methods Enzymol.* 17: 79-143, 1970.

Dayhoff, M.O., et al., "A Model of Evolutionary Change in Proteins." In *Atlas of Protein Sequence and Structure* 5: Suppl. 3 (National Biomedical Research Foundation, Washington, D.C., pp. 345-362, 1978.

Delgado-Jarana, J., et al., "Aspartyl protease from *Trichoderma harzianum* CECT 2413: Cloning and characterization." *Microbiology* 148(5): 1305-1315, 2002.

Fernandez-Abalos, J.M., et al., "Posttranslational processing of the xylanase Xys1L from *Streptomyces halstedii* JM8 is carried out by secreted serine proteases." *Microbiology* 149: 1623-1632, 2003.

Finkelstein, D., et al., "Transformation." In *Biotechnology of Filamentous Fungi Technology and Products*, Chapter 6, pp. 113-156, D.B. Finkelstein et al., eds., Butterworth-Heinemann, Boston, MA, 1992.

Goldman, G.H., et al., "Transformation of *Trichoderma harzianum* by high-voltage electric pulse." *Current Genetics* 17: 169-174, 1990.

Gomi, K., et al. "Cloning and Nucleotide Seouence of the Acid Protease-encoding Gene (pepA) from *Aspergillus orvzae*." *Biosci. Biotech. Biochem.* 57(7): 1095-1100, 1993.

Lorito, M., et al., "Biolistic transformation of *Trichoderma harzianum* and *Gliocladium virens* using plasmid and genomic DNA." *Current Genetics* 24: 349-356, 1993.

Mullaney, E.J., et al., "Primary structure of the *trpC* gene from *Aspergillus nidulans*." *Mol. Gen. Genet.* 199: 37-45, 1985.

Needleman, S.B., et al., "A General Method Applicable to the Search for Similarities in the Amino Acid Sequence of Two Proteins." *J. Mol. Biol.* 48: 443-453, 1970.

Nevalainen, K.M.H., et al., "The Molecular Biology of *Trichoderma* and Its Application to the Expression of Both Homologous and Heterologous Genes." In *Molecular Industrial Mycology*, Leong and Berka, eds., Marcel Dekker, Inc., NY, pp. 129-148, 1992.

Nunberg, J.H., et al., "Molecular Cloning and Characterization of the Glucoamylase Gene of *Aspergillus awamori*." *Molecular and Cellular Biology* 4(11): 2306-2315, 1984.

Pearson, W.R., et al., "Improved tools for biological sequence comparison." *Proc. Natl. Acad. Sci. USA* 85: 2444-2448, 1988.

Penttila, M., et al., "A versatile transformation system for the cellulolytic filamentous fungus *Trichoderma reesei*." *Gene* 61: 155-164, 1987.

RD 216,034—"Enzymatic silk degumming," Research Disclosure Journal, Database No. 216034, 1982.

Seffernick, J.L., et al., "Melamine Deaminase and Atrazine Chlorohydrolase: 98 Percent Identical but Functionally Different." *Journal of Bacteriology* 183(8): 2405-2410, 2001.

Shpaer, E.G., "GeneAssist," In *Methods in Molecular Biology*, Sequence Data Analysis Guidebook, vol. 70, pp. 173-187, S.R. Swindall, ed., Humana Press, Totowa, NJ, 1997.

Smith, T.F., et al., "Comparison of Biosequences." *Adv. Appl. Math.* 2:482-489, 1981.

Timberlake, W.E., "Cloning and Analysis of Fungal Genes." In *More Gene Manipulations in Fungi*, J.W. Bennett et al. eds., Academic Press, San Diego, pp. 51-81, 1991.

Van Den Hondel, C.A.M.J.J., et al., "Heterologous Gene Expression in Filamentous Fungi." In *More Gene Manipulations in Fungi*, J.W. Bennett, et al. eds., Academic Press, San Diego, pp. 396-428, 1991.

Viterbo, A., et al., Isolation of two aspartyl proteases from *Trichoderma asperellum* expressed uring colonization of cucumber roots. '*FEMS Microbiology Letters* 238(1): 151-158, 2004.

Yelton, M.M., et al., "Transformation of *Aspergillus nidulans* by using a *trpC* plasmid." *Proc. Natl. Acad. Sci. USA*, vol. 81, pp. 1470-1474, Mar. 1984.

Database UniProt 201011 database entry Q8X177_9HYPO, integrated on Mar. 1, 2002, and sequence alignment with SEQ ID No. 9 of the instant application.

International Search Report and the Written Opinion of the International Searching Authority for International Patent Application No. PCT/US2005/046435 dated Sep. 11, 2006.

European Search Report and Partial European Search for European Patent Application No. EP 10 01 1492 dated Jul. 26, 2011.

pTrex3g_NSP24 Nucleic Acid Sequence (SEQ ID NO: 1):

CTGCAGCCACTTGCAGTCCCGTGGAATTCTCACGGTGAATGTAGGCCTTTTGTAGGGTAGGAAT
TGTCACTCAAGCACCCCCAACCTCCATTACGCCTCCCCCATAGAGTTCCCAATCAGTGAGTCAT
GGCACTGTTCTCAAATAGATTGGGGAGAAGTTGACTTCCGCCCAGAGCTGAAGGTCGCACAACC
GCATGATATAGGGTCGGCAACGGCAAAAAAGCACGTGGCTCACCGAAAAGCAAGATGTTTGCGA
TCTAACATCCAGGAACCTGGATACATCCATCATCACGCACGACCACTTTGATCTGCTGGTAAAC
TCGTATTCGCCCTAAACCGAAGTGCGTGGTAAATCTACACGTGGGCCCCTTTCGGTATACTGCG
TGTGTCTTCTCTAGGTGCCATTCTTTTCCCTTCCTCTAGTGTTGAATTGTTTGTGTTGGAGTCC
GAGCTGTAACTACCTCTGAATCTCTGGAGAATGGTGGACTAACGACTACCGTGCACCTGCATCA
TGTATATAATAGTGATCCTGAGAAGGGGGGTTTGGAGCAATGTGGGACTTTGATGGTCATCAAA
CAAAGAACGAAGACGCCTCTTTTGCAAAGTTTTGTTTCGGCTACGGTGAAGAACTGGATACTTG
TTGTGTCTTCTGTGTATTTTTGTGGCAACAAGAGGCCAGAGACAATCTATTCAAACACCAAGCT
TGCTCTTTTGAGCTACAAGAACCTGTGGGGTATATATCTAGAGTTGTGAAGTCGGTAATCCCGC
TGTATAGTAATACGAGTCGCATCTAAATACTCCGAAGCTGCTGCGAACCCGGAGAATCGAGATG
TGCTGGAAAGCTTCTAGCGAGCGGCTAAATTAGCATGAAAGGCTATGAGAAATTCTGGAGACGG
CTTGTTGAATCATGGCGTTCCATTCTTCGACAAGCAAAGCGTTCCGTCGCAGTAGCAGGCACTC
ATTCCCGAAAAAACTCGGAGATTCCTAAGTAGCGATGGAACCGGAATAATATAATAGGCAATAC
ATTGAGTTGCCTCGACGGTTGCAATGCAGGGGTACTGAGCTTGGACATAACTGTTCCGTACCCC
ACCTCTTCTCAACCTTTGGCGTTTCCCTGATTCAGCGTACCCGTACAAGTCGTAATCACTATTA
ACCCAGACTGACCGGACGTGTTTTGCCCTTCATTTGGAGAAATAATGTCATTGCGATGTGTAAT
TTGCCTGCTTGACCGACTGGGGCTGTTCGAAGCCCGAATGTAGGATTGTTATCCGAACTCTGCT
CGTAGAGGCATGTTGTGAATCTGTGTCGGGCAGGACACGCCTCGAAGGTTCACGGCAAGGGAAA
CCACCGATAGCAGTGTCTAGTAGCAACCTGTAAAGCCGCAATGCAGCATCACTGGAAAATACAA
ACCAATGGCTAAAAGTACATAAGTTAATGCCTAAAGAAGTCATATACCAGCGGCTAATAATTGT
ACAATCAAGTGGCTAAACGTACCGTAATTTGCCAACGGCTTGTGGGGTTGCAGAAGCAACGGCA
AAGCCCCACTTCCCCACGTTTGTTTCTTCACTCAGTCCAATCTCAGCTGGTGATCCCCCAATTG
GGTCGCTTGTTTGTTCCGGTGAAGTGAAAGAAGACAGAGGTAAGAATGTCTGACTCGGAGCGTT
TTGCATACAACCAAGGGCAGTGATGGAAGACAGTGAAATGTTGACATTCAAGGAGTATTTAGCC
AGGGATGCTTGAGTGTATCGTGTAAGGAGGTTTGTCTGCCGATACGACGAATACTGTATAGTCA
CTTCTGATGAAGTGGTCCATATTGAAATGTAAGTCGGCACTGAACAGGCAAAAGATTGAGTTGA
AACTGCCTAAGATCTCGGGCCCTCGGGCCTTCGGCCTTTGGGTGTACATGTTTGTGCTCCGGGC
AAATGCAAAGTGTGGTAGGATCGAACACACTGCTGCCTTTACCAAGCAGCTGAGGGTATGTGAT
AGGCAAATGTTCAGGGGCCACTGCATGGTTTCGAATAGAAAGAGAAGCTTAGCCAAGAACAATA
GCCGATAAAGATAGCCTCATTAAACGGAATGAGCTAGTAGGCAAAGTCAGCGAATGTGTATATA
TAAAGGTTCGAGGTCCGTGCCTCCCTCATGCTCTCCCCATCTACTCATCAACTCAGATCCTCCA
GGAGACTTGTACACCATCTTTTGAGGCACAGAAACCCAATAGTCAACCATCACAAGTTTGTACA
AAAAAGCAGGCTCCGCGGCCGCCCCCTTCACCATGCAGACCTTTGGAGCTTTTCTCGTTTCCTT
CCTCGCCGCCAGCGGCCTGGCCGCGGCCCTCCCCACCGAGGGTCAGAAGACGGCTTCCGTCGAG
GTCCAGTACAACAAGAACTACGTCCCCCACGGCCCTACTGCTCTCTTCAAGGCCAAGAGAAAGT
ATGGCGCTCCCATCAGCGACAACCTGAAGTCTCTCGTGGCTGCCAGGCAGGCCAAGCAGGCTCT
CGCCAAGCGCCAGACCGGCTCGGCGCCCAACCACCCCAGTGACAGCGCCGATTCGGAGTACATC
ACCTCCGTCTCCATCGGCACTCCGGCTCAGGTCCTCCCCCTGGACTTTGACACCGGCTCCTCCG
ACCTGTGGGTCTTTAGCTCCGAGACGCCCAAGTCTTCGGCCACCGGCCACGCCATCTACACGCC
CTCCAAGTCGTCCACCTCCAAGAAGGTGTCTGGCGCCAGCTG

*FIG. 5A*

```
GTCCATCAGCTACGGCGACGGCAGCAGCTCCAGCGGCGATGTCTACACCGACAAGGTCACCATC
GGAGGCTTCAGCGTCAACACCCAGGGCGTCGAGTCTGCCACCCGCGTGTCCACCGAGTTCGTCC
AGGACACGGTCATCTCTGGCCTCGTCGGCCTTGCCTTTGACAGCGGCAACCAGGTCAGGCCCGCA
CCCGCAGAAGACGTGGTTCTCCAACGCCGCCAGCAGCCTGGCTGAGCCCCTTTTCACTGCCGAC
CTGAGGCACGGACAGAGGTAAGTAGACACTCACTGGAATTCGTTCCTTTCCCGATCATCATGAAA
GCAAGTAGACTGACTGAACCAAACAACTAGACGGCAGCTACAACTTTGGCTACATCGACACCAG
CGTCGCCAAGGGCCCCGTTGCCTACACCCCCGTTGACAACAGCCAGGGCTTCTGGGAGTTCACT
GCCTCGGGCTACTCTGTCGGCGGCGGCAAGCTCAACCGCAACTCCATCGACGGCATTGCCGACA
CCGGCACCACCCTGCTCCTCCTCGACGACAACGTCGTCGATGCCTACTACGCCAACGTCCAGTC
GGCCCAGTACGACAACCAGCAGGAGGGTGTCGTCTTCGACTGCGACGAGGACCTCCCTTCGTTC
AGCTTCGGTGTTGGAAGCTCCACCATCACCATCCCTGGCGATCTGCTGAACCTGACTCCCCTCG
AGGAGGGCAGCTCCACCTGCTTCGGTGGCCTCCAGAGCAGCTCCGGCATTGGCATCAACATCTT
TGGTGACGTTGCCCTCAAGGCTGCCCTGGTTGTCTTTGACCTCGGCAACGAGCGCCTGGGCTGG
GCTCAGAAATAAAAGGGTGGGCGCGCCGACCCAGCTTTCTTGTACAAAGTGGTGATCGCGCCAG
CTCCGTGCGAAAGCCTGACGCACCGGTAGATTCTTGGTGAGCCCGTATCATGACGGCGGCGGGA
GCTACATGGCCCCGGGTGATTTATTTTTTTTGTATCTACTTCTGACCCTTTTCAAATATACGGT
CAACTCATCTTTCACTGGAGATGCGGCCTGCTTGGTATTGCGATGTTGTCAGCTTGGCAAATTG
TGGCTTTCGAAAACACAAAACGATTCCTTAGTAGCCATGCATTTTAAGATAACGGAATAGAAGA
AAGAGGAAATTAAAAAAAAAAAAAAAAAACAAACATCCCGTTCATAACCCGTAGAATCGCCGCTCT
TCGTGTATCCCAGTACCAGTTTATTTTGAATAGCTCGCCCGCTGGAGAGCATCCTGAATGCAAG
TAACAACCGTAGAGGCTGACACGGCAGGTGTTGCTAGGGAGCGTCGTGTTCTACAAGGCCAGAC
GTCTTCGCGGTTGATATATATGTATGTTTGACTGCAGGCTGCTCAGCGACGACAGTCAAGTTCG
CCCTCGCTGCTTGTGCAATAATCGCAGTGGGGAAGCCACACCGTGACTCCCATCTTTCAGTAAA
GCTCTGTTGGTGTTTATCAGCAATACACGTAATTTAAACTCGTTAGCATGGGGCTGATAGCTTA
ATTACCGTTTACCAGTGCCATGGTTCTGCAGCTTTCCTTGGCCCGTAAAATTCGGCGAAGCCAG
CCAATCACCAGCTAGGCACCAGCTAAACCCTATAATTAGTCTCTTATCAACACCATCCGCTCCC
CCGGGATCAATGAGGAGAATGAGGGGGATGCGGGGCTAAAGAAGCCTACATAACCCTCATGCCA
ACTCCCAGTTTACACTCGTCGAGCCAACATCCTGACTATAAGCTAACACAGAATGCCTCAATCC
TGGGAAGAACTGGCCGCTGATAAGCGCGCCCGCCTCGCAAAAACCATCCCTGATGAATGGAAAG
TCCAGACGCTGCCTGCGGAAGACAGCGTTATTGATTTCCCAAAGAAATCGGGGATCCTTTCAGA
GGCCGAACTGAAGATCACAGAGGCCTCCGCTGCAGATCTTGTGTCCAAGCTGGCGGCCGGAGAG
TTGACCTCGGTGGAAGTTACGCTAGCATTCTGTAAACGGGCAGCAATCGCCCAGCAGTTAGTAG
GGTCCCCTCTACCTCTCAGGGAGATGTAACAACGCCACCTTATGGGACTATCAAGCTGACGCTG
GCTTCTGTGCAGACAAACTGCGCCCACGAGTTCTTCCCTGACGCCGCTCTCGCGCAGGCAAGGG
AACTCGATGAATACTACGCAAAGCACAAGAGACCCGTTGGTCCACTCCATGGCCTCCCCATCTC
TCTCAAAGACCAGCTTCGAGTCAAGGTACACCGTTGCCCCTAAGTCGTTAGATGTCCCTTTTTG
TCAGCTAACATATGCCACCAGGGCTACGAAACATCAATGGGCTACATCTCATGGCTAAACAAGT
ACGACGAAGGGGACTCGGTTCTGACAACCATGCTCCGCAAAGCCGGTGCCGTCTTCTACGTCAA
GACCTCTGTCCCGCAGACCCTGATGGTCTGCGAGACAGTCAACAACATCATCGGGCGCACCGTC
AACCCACGCAACAAGAACTGGTCGTGCGGCGGCAGTTCTGGTGGTGAGGGTGCGATCGTTGGGA
TTCGTGGTGGCGTCATCGGTGTAGGAACGGATATCGGTGGCTCGATTCGAGTGCCGGCCGCGTT
CAACTTCCTGTACGGTCTAAGGCCGAGTCATGGGCGGCTGCCGTATGCAAAGATGGCGAACAGC
ATGGAGGGTCAGGAGACGGTGCACAGCGTTGTCGGGCCGATTACGCACTCTGTTGAGGGTGAGT
CCTTCGCCTCTTCCTTCTTTTCCTGCTCTATACCAGGCCTCCACTGTCCTCCTTTCTTGCTTTT
TATACTATATACGAGACCGGCAGTCACTGATGAAGTATGTTAGACCTCCGCCTCTTCACCAAAT
CCGTCCTCGGTCAGGAGCCATGGAAATACGACTCCAAGGTCATCCCCATGCCCTGGCGCCAGTC
CGAGTCGGACATTATTGCCTCCAAGATCAAGAACGGCGGGCTCAATATCGGCTACTACAACTTC
GACGGCAATGTCCTTCCACACCCTCCTATCCTGCGCGGCGTGGAAACCACCGTCGCCGCACTCG
CCAAAGCCGGTCACACCGTGACCCCGTGGACGCCATACAAGCACGATTTCGGCCACGATCTCAT
CTCCCATATCTACGCGGCTGACGGCAGCGCCGACGTAATGCGCGATATC
```

*FIG. 5B*

```
AGTGCATCCGGCGAGCCGGCGATTCCAAATATCAAAGACCTACTGAACCCGAACATCAAAGCTG
TTAACATGAACGAGCTCTGGGACACGCATCTCCAGAAGTGGAATTACCAGATGGAGTACCTTGA
GAAATGGCGGGAGGCTGAAGAAAAGGCCGGGAAGGAACTGGACGCCATCATCGCGCCGATTACG
CCTACCGCTGCGGTACGGCATGACCAGTTCCGGTACTATGGGTATGCCTCTGTGATCAACCTGC
TGGATTTCACGAGCGTGGTTGTTCCGGTTACCTTTGCGGATAAGAACATCGATAAGAAGAATGA
GAGTTTCAAGGCGGTTAGTGAGCTTGATGCCCTCGTGCAGGAAGAGTATGATCCGGAGGCGTAC
CATGGGGCACCGGTTGCAGTGCAGGTTATCGGACGGAGACTCAGTGAAGAGAGGACGTTGGCGA
TTGCAGAGGAAGTGGGGAAGTTGCTGGGAAATGTGGTGACTCCATAGCTAATAAGTGTCAGATA
GCAATTTGCACAAGAAATCAATACCAGCAACTGTAAATAAGCGCTGAAGTGACCATGCCATGCT
ACGAAAGAGCAGAAAAAAACCTGCCGTAGAACCGAAGAGATATGACACGCTTCCATCTCTCAAA
GGAAGAATCCCTTCAGGGTTGCGTTTCCAGTCTAGACACGTATAACGGCACAAGTGTCTCTCAC
CAAATGGGTTATATCTCAAATGTGATCTAAGGATGGAAAGCCCAGAATATCGATCGCGCGCAGA
TCCATATATAGGGCCCGGGTTATAATTACCTCAGGTCGACGTCCCATGGCCATTCGAATTCGTA
ATCATGGTCATAGCTGTTTCCTGTGTGAAATTGTTATCCGCTCACAATTCCACACAACATACGA
GCCGGAAGCATAAAGTGTAAAGCCTGGGGTGCCTAATGAGTGAGCTAACTCACATTAATTGCGT
TGCGCTCACTGCCCGCTTTCCAGTCGGGAAACCTGTCGTGCCAGCTGCATTAATGAATCGGCCA
ACGCGCGGGGAGAGGCGGTTTGCGTATTGGGCGCTCTTCCGCTTCCTCGCTCACTGACTCGCTG
CGCTCGGTCGTTCGGCTGCGGCGAGCGGTATCAGCTCACTCAAAGGCGGTAATACGGTTATCCA
CAGAATCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTAGGTC
GTTCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCCAGTTACCTTCGGAA
AAAGAGTTGGTAGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGATCTTTTCTACGGGG
TCTGACGCTCAGTGGAACGAAAACTCACGTTAAGGGATTTTGGTCATGAGATTATCAAAAAGGA
TCTTCACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAGCAAT
AAACCAGCCAGCCGGAAGGGCCGAGCGCAGAAGTGGTCCTGCAACTTTATCCGCCTCCATCCAG
TCTATTAATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAGCTCCTTC
GGTCCTCCGATCGTTGTCAGAAGTAAGTTGGCCGCAGTGTTATCACTCATGGTTATGGCAGCAC
TGCATAATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAATACGGGAT
AATACCGCGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTTTTTCAATATT
ATTGAAGCATTTATCAGGGTTATTGTCTCATGAGCGGATACATATTTGAATGTATTTAGAAAAA
TAAACAAATAGGGGTTCCGCGCACATTTCCCCGAAAAGTGCCACCTGACGTCTAAGAAACCATT
ATTATCATGACATTAACCTATAAAAATAGGCGTATCACGAGGCCCTTTCGTCTCGCGCGTTTCG
GTGATGACGGTGAAAACCTCTGACACATGCAGCTCCCGGAGACGGTCACAGCTTGTCTGTAAGC
GGATGCCGGGAGCAGACAAGCCCGTCAGGGCGCGTCAGCGGGTGTTGGC
```

FIG. 5C

GGGTGTCGGGGCTGGCTTAACTATGCGGCATCAGAGCAGATTGTACTGAGAGTGCACCATAAAA
TTGTAAACGTTAATATTTTGTTAAAAATTCGCGTTAAATTTTTGTTAAATCAGCTCATTTTTTAA
CCAATAGGCCGAAATCGGCAAAATCCCTTATAAATCAAAAGAATAGCCCGAGATAGGGTTGAGT
GTTGTTCCAGTTTGGAACAAGAGTCCACTATTAAAGAACGTGGACTCCAACGTCAAAGGGCGAA
AAACCGTCTATCAGGGCGATGGCCCACTACGTGAACCATCACCCAAATCAAGTTTTTTGGGGTC
GAGGTGCCGTAAAGCACTAAATCGGAACCCTAAAGGGAGCCCCCGATTTAGAGCTTGACGGGGA
AAGCCCGGCGAACGTGGCGAGAAAGGAAGGGAAGAAAGCGAAAGGAGCGGGCGCTAGGGCGCTGG
CAAGTGTAGCGGTCACGCTGCGCGTAACCACCACACCCGCCGCGCTTAATGCGCCGCTACAGGG
CGCGTACTATGGTTGCTTTGACGTATGCGGTGTGAAATACCGCACAGATGCGTAAGGAGAAAAT
ACCGCATCAGGCGCCATTCGCCATTCAGGCTGCGCAACTGTTGGGAAGGGCGATCGGTGCGGGC
CTCTTCGCTATTACGCCAGCTGGCGAAAGGGGATGTGCTGCAAGGCGATTAAGTTGGGTAACG
CCAGGGTTTTCCCAGTCACGACGTTGTAAAACGACGGCCAGTGCCCAAGCTTACTAGTACTTCT
CGAGCTCTGTACATGTCCGGTCGCGACGTACGCGTATCGATGGCGCCAGCTGCAGGCGGCCGC

FIG. 5D

NSP24 Amino Acid Sequence – 407 Amino Acids (SEQ ID NO: 2):

MQTFGAFLVSFLAASGLAAALPTEGQKTASVEVQYNKNYVPHGPTALFKAKRKYGAPISDNLKS
LVAARQAKQALAKRQTGSAPNHPSDSADSEYITSVSIGTPAQVLPLDFDTGSSDLWVPSSETPK
SSATGHAIYTPSKSSTSKKVSGASWSISYGDGSSSSGDVYTDKVTIGGFSVNTQGVESATRVST
EFVQDTVISGLVGLAFDSGNQVRPHPQKTWFSNAASSLAEPLFTADLRHGQNGSYNFGYIDTSV
AKGPVAYTPVDNSQGFWEFTASGYSVGGGKLNRNSIDGIADTGTTLLLLDDNVVDAYYANVQSA
QYDNQQEGVVFDCDEDLPSFSFGVGSSTITIPGDLLNLTPLEEGSSTCFGGLQSSSGIGINIFG
DVALKAALVVFDLGNERLGWAQK

FIG. 6A

NSP24 Polynucleotide Sequence (SEQ ID NO: 8)

ATGCAGACCTTTGGAGCTTTTCTCGTTTCCTTCCTCGCCGCCAGCGGCCTGGCCGCGGCCCTCC
CCACCGAGGGTCAGAAGACCGGCTTCCGTCGAGGTCCAGTACAACAAGAACTACGTCCCCCACGG
CCCTACTGCTCTCTTCAAGGCCAAGAGAAAGTATGGCGCTCCCATCAGCGACAACCTGAAGTCT
CTCGTGGCTGCCAGGCAGGCCAAGCAGGCTCTCGCCAAGCGCCAGACCGGCTCGGCGCCCAACC
ACCCCAGTGACAGCGCCGATTCGGAGTACATCACCTCCGTCTCCATCGGCACTCCGGCTCAGGT
CCTCCCCCTGGACTTTGACACCGGCTCCTCCGACCTGTGGGTCTTTAGCTCCGAGACGCCCAAG
TCTTCGGCCACCGGCCACGCCATCTACACGCCCTCCAAGTCGTCCACCTCCAAGAAGGTGTCTG
GCGCCAGCTGGTCCATCAGCTACGGCGACGGCAGCAGCTCCAGCGGCGATGTCTACACCGACAA
GGTCACCATCGGAGGCTTCAGCGTCAACACCCAGGGCGTCGAGTCTGCCACCCGCGTGTCCACC
GAGTTCGTCCAGGACACGGTCATCTCTGGCCTCGTCGGCCTTGCCTTTGACAGCGGCAACCAGG
TCAGGCCGCACCCGCAGAAGACGTGGTTCTCCAACGCCGCCAGCAGCCTGGCTGAGCCCCTTTT
CACTGCCGACCTGAGGCACGGACAGA**GTAAGTAGACACTCACTGGAATTCGTTCCTTTCCCGAT
CATCATGAAAGCAAGTAGACTGACTGAACCAAACAACTAGA**CGGCAGCTACAACTTTGGCTACA
TCGACACCAGCGTCGCCAAGGGCCCCGTTGCCTACACCCCCGTTGACAACAGCCAGGGCTTCTG
GGAGTTCACTGCCTCGGGCTACTCTGTCGGCGGCGGCAAGCTCAACCGCAACTCCATCGACGGC
ATTGCCGACACCGGCACCACCCTGCTCCTCCTCGACGACAACGTCGTCGATGCCTACTACGCCA
ACGTCCAGTCGGCCCAGTACGACAACCAGCAGGAGGGTGTCGTCTTCGACTGCGACGAGGACCT
CCCCTTCGTTCAGCTTCGGTGTTGGAAGCTCCACCATCACCATCCCTGGCGATCTGCTGAACCTG
ACTCCCCTCGAGGAGGGCAGCTCCACCTGCTTCGGTGGCCTCCAGAGCAGCTCCGGCATTGGCA
TCAACATCTTTGGTGACGTTGCCCTCAAGGCTGCCCTGGTTGTCTTTGACCTCGGCAACGAGCG
CCTGGGCTGGGCTCAGAAATAA

FIG. 6B

(SEQ ID NO: 3) - Nucleic Acid Sequence Encoding a pepA Protease, with Putative Introns in Bold ATGGTCGTCTTCAGCAAAACCGCTGCCCTCGTTCTGGGTCTGTCCTCCGCCGTCTCTGCGGCGC
CGGCTCCTACTCGCAAGGGCTTCACCATCAACCAGATTGCCCGGCCTGCCAACAAGACCCGCAC
CATCAACCTGCCAGGCATGTACGCCCGTTCCCTGGCCAAGTTTGGCGGTACGGTGCCCCAGAGC
GTGAAGGAGGCTGCCAGCAAGGGTAGTGCCGTGACCACGCCCCAGAACAATGACGAGGAGTACC
TGACTCCCGTCACTGTCGGAAAGTCCACCCTCCATCTGGACTTTGACACCGGATCTGCAGATCT
GTAAGCTTCCCTGCTCGGGTGTTCGGGCAAATCGTGACTAACCTGGACTAGCTGGGTCTTCTCG
GACGAGCTCCCTTCCTCGGAGCAGACCGGTCACGATCTGTACACGCCTAGCTCCAGCGCGACCA
AGCTGAGCGGCTACACTTGGGACATCTCCTACGGTGACGGCAGCTCGGCCAGCGGAGACGTGTA
CCCGGGATACTGTCACTGTCGGCGGTGTCACCACCAACAAGCAGGCTGTTGAAGCAGCCAGCAAG
ATCAGCTCCGAGTTCGTTCAGAACACGGCCAATGACGGCCTTTTGGGACTGGCCTTTAGCTCCA
TCAACACTGGTGAGTCAATCCTACATCAGCCGGGTTGACCTACCTGCTGACCGATACACAGTCC
AGCCCAAGGCGCAGACCACCTTCTTCGACACCGTCAAGTCCCAGCTGGACTCTCCCCTTTTCGC
CGTGCAGCTGAAGCACGACGCCCCCGGTGTTTACGACTTTGGCTACATCGATGACTCCAAGTAC
ACCGGTTCTATCACCTACACGGATGCCGATAGCTCCCAGGGTTACTGGGGCTTCAGCACCGACG
GCTACAGTATCGGTGACGGCAGCTCCAGCTCCAGCGGCTTCAGCGCCATTGCTG**GTAAGAACCG
CCTTCATTTAACACACAACTTGTCCACCTCTTTACTAACTAGTGTATAG**ACACCGGTACCACCC
TCATCCTCCTCGATGACGAAATCGTCTCCGCCTACTACGAGCAGGTTTCTGGCGCTCAGGAGAG
CGAGGAAGCCGGTGGCTACGTTTTCTCTTGCTCGACCAACCCCCCTGACTTCACTGTCGTGATT
GGCGACTACAAGGCCGTTGTTCCGGGCAAGTACATCAACTACGCTCCCATCTCGACTGGCAGCT
CCACCTGCTTTGGCGGTATCCAGAGCAACAGCGGTCTGGGACTGTCCATCCTGGGTGATGTTTT
CTTGAAGAGCCAGTACGTGGTCTTCAACTCTGAGGGCCCTAAGCTGGGATTCGCCGCTCAGGCT
TAG

*FIG. 8*

(SEQ ID NO: 4) Nucleic Acid Sequence Encoding a NSP25 Protease -

ATGCAGCCCTCATTTGGCAGCTTCCTCGTCACCGTCCTGTCTGCCTCCATGGCAGCAGGCAGTG
TCATTCCCAGCACAAACGCCAACCCTGGCTCCTTCGAGATCAAGAGATCCGCCAACAAAGCCTT
CACAGGCCGCAATGGCCCTCTAGCATTAGCCCGTACATACGCCAAGTACGGTGTTGAAGTCCCC
AAAACTCTGGTCGATGCTATTCAACTCGTCAAGTCCATCCAGCTCGCAAAGCGGGACAGCGCCA
CCGTCACTGCCACGCCCGGACCACGACGACATCGAGTATCTTGTCCCCGTCAAGATCGGAACTCC
TCCCCAAACACTTAACCTGGATTTTGACACGGGCAGCTCCGATCTCTGGGTCTTCTCATCAGAT
GTCGACCCGACCTCCTCCCAGGGCCATGACATCTACACCCCGTCCAAGAGCACATCTTCCAAAA
AGTTGGAAGGAGCCTCATGGAACATCACATATGGAGACCGCTCATCATCATCCGGCGATGTCTA
CCACGATATTGTCTCCGTCGGAAACCTGACAGTAAAGTCCCAAGCCGTCGAGTCCGCTCGAAAC
GTCTCGGCCAGTTCACCCAGGGCAACAACGACGGCCTCGTCGGCCTGGCGTTTAGCTCCATCAA
CACAGTCAAGCCCACGCCGCAAAAGACGTGGTACGACAACATCGTCGGCAGCCTTGACTCTCCC
GTCTTTGTTGCTGATCTGCGCCACGACACGCCCGGCAGCTACCACTTCGGCTCCATCCCCTCCG
AAGCAAGCAAAGCCTTCTACGCCCCCATCGACAACAGCAAGGGCTTCTGGCAATTCAGCACGAG
CAGCAACATTAGCGGCCAGTTCAACGCCGTTGCAGACACTGGCACTACTCTGCTGCTCGCCAGC
GACGACCTCGTCAAGGCCTACTACGCAAAGGTCCAGGGCGCCCGTGTGAACGTCTTCCTGGGCG
GCTACGTCTTCAACTGCACCACTCAGCTGCCCGACTTTACCTTTACTGTTGGAGAGGGCAACAT
CACTGTCCCCGGTACCTTGATAAACTATTCCGAGGCTGGCAACGGCCAGTGTTTTGGCGGTATT
CAGCCGTCGGGGGGTCTTCCTTTTGCTATCTTTGGTGACATTGCTCTTAAGGCTGCGTATGTTA
TTTTTGACAGTGGCAACAAGCAGGTTGGCTGGGCGCAGAAGAAATAG

*FIG. 9A*

SEQ ID NO: 9 - The Deduced NSP25 Amino Acid Sequence (399 Amino Acids)

MQPSFGSFLVTVLSASMAAGSVIPSTNANPGSFEIKRSANKAFTGRNGPLALARTYAKYG
VEVPKTLVDAIQLVKSIQLAKRDSATVTATPDHDDIEYLVPVKIGTPPQTLNLDFDTGSS
DLWVFSSDVDPTSSQGHDIYTPSKSTSSRKLEGASWNITYGDRSSSSGDVYHDIVSVGNL
TVKSQAVESARNVSXQFTQGNNDGLVGLAFSSINTVKPTPQKTWYDNIVGSLDSPVFVAD
LRHDTPGSYHFGSIPSEASKAFYAPIDNSKGFWQFSTSSNISGQFNAVADTGTTLLLASD
DLVKAYYAKVQGARVNVFLGGYVFNCTTQLPDFTFTVGEGNITVPGTLINYSEAGNGQCF
GGIQPSGGLPFAIFGDIALKAAYVIFDSGNKQVGWAQRK

FIG. 9B

SEQ ID NO: 5 - Nucleic Acid Sequence for a Novel pepA Protease (L388M)

ATGGTCGTCTTCAGCAAAACCGCTGCCCTCGTTCTGGGTCTGTCCTCCGCCGTCTCTGCGGCGC
CGGCTCCTACTCGCAAGGGCTTCACCATCAACCAGATTGCCCGGCCTGCCAACAAGACCCGCAC
CATCAACCTGCCAGGCATGTACGCCCGTTCCCTGGCCAAGTTTGGCGGTACGGTGCCCCAGAGC
GTGAAGGAGGCTGCCAGCAAGGGTAGTGCCGTGACCACGCCCCAGAACAATGACGAGGAGTACC
TGACTCCCGTCACTGTCGGAAAGTCCACCCTCCATCTGGACTTTGACACCGGATCTGCAGATCT
GTAAGCTTCCCTGCTCGGGTGTTCGGGCAAATCGTGACTAACCTGGACTAGCTGGGTCTTCTCG
GACGAGCTCCCTTCCTCGGAGCAGACCGGTCACGATCTGTACACGCCTAGCTCCAGCGCGACCA
AGCTGAGCGGCTACACTTGGGACATCTCCTACGGTGACGGCAGCTCGGCCAGCGGAGACGTGTA
CCGGGATACTGTCACTGTCGGCGGTGTCACCACCAACAAGCAGGCTGTTGAAGCAGCCAGCAAG
ATCAGCTCCGAGTTCGTTCAGAACACGGCCAATGACGGCCTTTTGGGACTGGCCTTTAGCTCCA
TCAACACTGGTGAGTCAATCCTACATCAGCCGGGTTGACCTACCTGCTGACCGATACACAGTCC
AGCCCAAGGCGCAGACCACCTTCTTCGACACCGTCAAGTCCCAGCTGGACTCTCCCCTTTTCGC
CGTGCAGCTGAAGCACGACGCCCCCGGTGTTTACGACTTTGGCTACATCGATGACTCCAAGTAC
ACCGGTTCTATCACCTACACGGATGCCGATAGCTCCCAGGGTTACTGGGGCTTCAGCACCGACG
GCTACAGTATCGGTGACGGCAGCTCCAGCTCCAGCGGCTTCAGCGCCATTGCT**GTAAGAACCG
CCTTCATTTAACACACAACTTGTCCACCTCTTTACTAACTAGTGTATAGA**CACCGGTACCACCC
TCATCCTCCTCGATGACGAAATCGTCTCCGCCTACTACGAGCAGGTTTCTGGCGCTCAGGAGAG
CGAGGAAGCCGGTGGCTACGTTTTCTCTTGCTCGACCAACCCCCCTGACTTCACTGTCGTGATT
GGCGACTACAAGGCCGTTGTTCCGGGCAAGTACATCAACTACGCTCCCATCTCGACTGGCAGCT
CCACCTGCTTTGGCGGTATCCAGAGCAACAGCGGTCTGGGACTGTCCATCCTGGGTGATGTTTT
CTTGAAGAGCCAGTACGTGGTCTTCAACTCTGAGGGCCCTAAGATGGGATTCGCCGCTCAGGCT
TAG

FIG. 10

SEQ ID NO:6

```
TACGTATTTT GAATAGCTCG CCCGCTGGAG AGCATCCTGA ATGCAAGTAA
CAACCGTAGA GGCTGACACG GCAGGTGTTG CTAGGGAGCG TCGTGTTCTA
CAAGGCCAGA CGTCTTCGCG GTTGATATAT ATGTATGTTT GACTGCAGGC
TGCTCAGCGA CGACAGTCAA GTTCGCCCTC GCTGCTTGTG CAATAATCGC
AGTGGGGAAG CCACACCGTG ACTCCATCT TTCAGTAAAG CTCTGTTGGT
GTTTATCAGC AATACACGTA ATTTAAACTC GTTAGCATGG GGCTGATAGC
TTAATTACCG TTTACCAGTG CCGCGGTCT GCAGCTTTCC TTGGCCCGTA
AAATTCGGCG AAGCCAGCCA ATCCAGCT AGGCACCAGC TAAACCCTAT
AATTAGTCTC TTATCAACAC CATCCGCTCC CCCGGGATCA ATGAGGAGAA
TGAGGGGGAT GCGGGCTAA AGAAGCCTAC ATAACCCTCA TGCCAACTCC
CAGTTTACAC TCGTCGAGCC AACATCCTGA CTATAAGCTA ACACAGAATG
CCTCAATCCT GGGAAGAACT GGCCGCTGAT AAGCGCGCCC GCCTCGCAAA
AACCATCCCT GATGAATGGA AAGTCCAGAC GCTGCCTGCG GAAGACAGCG
TTATTGATTT CCCAAAGAAA TCGGGGATCC TTTCAGAGGC CGAACTGAAG
ATCACAGAGG CCTCCGCTGC AGATCTTGTG TCCAAGCTGG CGGCCGGAGA
GTTGACCTCG GTGGAAGTTA CGCTAGCATT CTGTAAACGG GCAGCAATCG
CCCAGCAGTT AGTAGGGTCC CCTCTACCTC TCAGGGAGAT GTAACAACGC
CACCTTATGG GACTATCAAG CTGACGCTGG CTTCTGTGCA GACAAACTGC
GCCCACGAGT TCTTCCCTGA CGCCGCTCTC GCGCAGGCAA GGGAACTCGA
TGAATACTAC GCAAAGCACA AGAGACCCGT TGGTCCACTC CATGGCCTCC
CCATCTCTCT CAAAGACCAG CTTCGAGTCA AGGTACACCG TTGCCCCTAA
GTCGTTAGAT GTCCCTTTTT GTCAGCTAAC ATATGCCACC AGGGCTACGA
AACATCAATG GCTACATCT CATGGCTAAA CAAGTACGAC GAAGGGGACT
CGGTTCTGAC AACCATGCTC CGCAAAGCCG GTGCCGTCTT CTACGTCAAG
ACCTCTGTCC CGCAGACCCT GATGGTCTGC GAGACAGTCA ACAACATCAT
CGGGCGCACC GTCAACCCAC GCAACAAGAA CTGGTCGTGC GGCGGCAGTT
CTGGTGGTGA GGGTGCGATC GTTGGGATTC GTGGTGGCGT CATCGGTGTA
GGAACGGATA TCGGTGGCTC GATTCGAGTG CCGGCCGCGT TCAACTTCCT
GTACGGTCTA AGGCCGAGTC ATGGGCGGCT GCCGTATGCA AAGATGGCGA
ACAGCATGGA GGGTCAGGAG ACGGTGCACA GCGTTGTCGG GCCGATTACG
CACTCTGTTG AGGGTGAGTC CTTCGCCTCT TCCTTCTTTT CCTGCTCTAT
ACCAGGCCTC CACTGTCCTC CTTTCTTGCT TTTTATACTA TATACGAGAC
CGGCAGTCAC TGATGAAGTA TGTTAGACCT CCGCCTCTTC ACCAAATCCG
TCCTCGGTCA GGAGCCATGG AAATACGACT CCAAGGTCAT CCCCATGCCC
TGGCGCCAGT CCGAGTCGGA CATTATTGCC TCCAAGATCA AGAACGGCGG
GCTCAATATC GGCTACTACA ACTTCGACGG CAATGTCCTT CCACACCCTC
CTATCCTGCG CGGCGTGGAA ACCACCGTCG CCGCACTCGC CAAAGCCGGT
CACACCGTGA CCCCGTGGAC GCCATACAAG CACGATTTCG GCCACGATCT
CATCTCCCAT ATCTACGCGG CTGACGGCAG CGCCGACGTA ATGCGCGATA
TCAGTGCATC CGGCGAGCCG GCGATTCCAA ATATCAAAGA CCTACTGAAC
CCGAACATCA AAGCTGTTAA CATGAACGAG CTCTGGGACA CGCATCTCCA
GAAGTGGAAT TACCAGATGG AGTACCTTGA GAAATGGCGG GAGGCTGAAG
AAAAGGCCGG GAAGGAACTG GACGCCATCA TCGCGCCGAT TACGCCTACC
GCTGCGGTAC GGCATGACCA GTTCCGGTAC TATGGGTATG CCTCTGTGAT
CAACCTGCTG GATTTCACGA GCGTGGTTGT TCCGGTTACC TTTGCGGATA
```

FIG. 12A

```
AGAACATCGA TAAGAAGAAT GAGAGTTTCA AGGCGGTTAG TGAGCTTGAT
GCCCTCGTGC AGGAAGAGTA TGATCCGGAG GCGTACCATG GGGCACCGGT
TGCAGTGCAG GTTATCGGAC GGAGACTCAG TGAAGAGAGG ACGTTGGCGA
TTGCAGAGGA AGTGGGGAAG TTGCTGGGAA ATGTGGTGAC TCCATAGCTA
ATAAGTGTCA GATAGCAATT TGCACAAGAA ATCAATACCA GCAACTGTAA
ATAAGCGCTG AAGTGACCAT GCCATGCTAC GAAAGAGCAG AAAAAAACCT
GCCGTAGAAC CGAAGAGATA TGACACGCTT CCATCTCTCA AAGGAAGAAT
CCCTTCAGGG TTGCGTTTCC AGTCTAGCTA GAGTCGAGGA TTGCCTGAAC
ATTGACATTC GGCGTCCGGC CGGGACCACC GCGGACTCGA AGCTGCCTGT
GCTGGTCTGG ATCTTTGGCG GAGGCTTTGA ACTTGGTTCA AAGGCGATGT
ATGATGGTAC AACGATGGTA TCATCGTCGA TAGACAAGAA CATGCCTATC
GTGTTTGTAG CAATGAATTA TCGCGTGGGA GGTTTCGGGT TCTTGCCCGG
AAAGGAGATC CTGGAGGACG GGTCCGCGAA CCTAGGGCTC CTGGACCAAC
GCCTTGCCCT GCAGTGGGTT GCCGACAACA TCGAGGCCTT TGGTGGAGAC
CCGGACAAGG TGACGATTTG GGGAGAATCA GCAGGAGCCA TTTCCGTTTT
TGATCAGATG ATCTTGTACG ACGGAAACAT CACTTACAAG GATAAGCCCT
TGTTCCGGGG GGCCATCATG GACTCCGGTA GTGTTGTTCC CGCAGACCCC
GTCGATGGGG TCAAGGGACA GCAAGTATAT GATGCGGTAG TGGAATCTGC
AGGCTGTTCC TCTTCTAACG ACACCCTAGC TTGTCTGCGT GAACTAGACT
ACACCGACTT CCTCAATGCG GCAAACTCCG TGCCAGGCAT TTTAAGCTAC
CATTCTGTGG CGTTATCATA TGTGCCTCGA CCGGACGGGA CGGCGTTGTC
GGCATCACCG GACGTTTTGG GCAAAGCAGG GAAATATGCT CGGGTCCCGT
TCATCGTGGG CGACCAAGAG GATGAGGGGA CCTTATTCGC CTTGTTTCAG
TCCAACATTA CGACGATCGA CGAGGTGGTC GACTACCTGG CCTCATACTT
CTTCTATGAC GCTAGCCGAG AGCAGCTTGA AGAACTAGTG GCCCTGTACC
CAGACACCAC CACGTACGGG TCTCCGTTCA GGACAGGCGC GGCCAACAAC
TGGTATCCGC AATTTAAGCG ATTGGCCGCC ATTCTCGGCG ACTTGGTCTT
CACCATTACC CGGCGGGCAT TCCTCTCGTA TGCAGAGGAA ATCTCCCCTG
ATCTTCCGAA CTGGTCGTAC CTGGCGACCT ATGACTATGG CACCCCAGTT
CTGGGGACCT TCCACGGAAG TGACCTGCTG CAGGTGTTCT ATGGGATCAA
GCCAAACTAT GCAGCTAGTT CTAGCCACAC GTACTATCTG AGCTTTGTGT
ATACGCTGGA TCCGAACTCC AACCGGGGGG AGTACATTGA GTGGCCGCAG
TGGAAGGAAT CGCGGCAGTT GATGAATTTC GGAGCGAACG ACGCCAGTCT
CCTTACGGAT GATTTCCGCA ACGGGACATA TGAGTTCATC CTGCAGAATA
CCGCGGCGTT CCACATCTGA TGCCATTGGC GGAGGGGTCC GGACGGTCAG
GAACTTAGCC TTATGAGATG AATGATGGAC GTGTCTGGCC TCGGAAAAGG
ATATATGGGG ATCATGATAG TACTAGCCAT ATTAATGAAG GGCATATACC
ACGCGTTGGA CCTGCGTTAT AGCTTCCCGT TAGTTATAGT ACCATCGTTA
TACCAGCCAA TCAAGTCACC ACGCACGACC GGGGACGGCG AATCCCCGGG
AATTGAAAGA AATTGCATCC CAGGCCAGTG AGGCCAGCGA TTGGCCACCT
CTCCAAGGCA CAGGGCCATT CTGCAGCGCT GGTGGATTCA TCGCAATTTC
CCCCGGCCCG GCCCGACACC GCTATAGGCT GGTTCTCCCA CACCATCGGA
GATTCGTCGC CTAATGTCTC GTCCGTTCAC AAGCTGAAGA GCTTGAAGTG
GCGAGATGTC TCTGCAGGAA TTCAAGCTAG ATGCTAAGCG ATATTGCATG
GCAATATGTG TTGATGCATG TGCTTCTTCC TTCAGCTTCC CCTCGTGCAG
```

*FIG. 12B*

```
ATGAGGTTTG GCTATAAATT GAAGTGGTTG GTCGGGGTTC CGTGAGGGGC
TGAAGTGCTT CCTCCCTTTT AGACGCAACT GAGAGCCTGA GCTTCATCCC
CAGCATCATT ACACCTCGAG ATGGTCGTCT TCAGCAAAAC CGCTGCCCTC
                     ^^^^^^
               Xho I
GTTCTGGGTC TGTCCTCCGC CGTCTCTGCG GCGCCGGCTC CTACTCGCAA
GGGCTTCACC ATCAACCAGA TTGCCCGGCC TGCCAACAAG ACCCGCACCA
TCAACCTGCC AGGCATGTAC GCCCGTTCCC TGGCCAAGTT TGGCGGTACG
GTGCCCCAGA GCGTGAAGGA GGCTGCCAGC AAGGGTAGTG CCGTGACCAC
GCCCCAGAAC AATGACGAGG AGTACCTGAC TCCCGTCACT GTCGGAAAGT
CCACCCTCCA TCTGGACTTT GACACCGGAT CTGCAGATCT GTAAGCTTCC
CTGCTCGGGT GTTCGGGCAA ATCGTGACTA ACCTGGACTA GCTGGGTCTT
CTCGGACGAG CTCCCTTCCT CGGAGCAGAC CGGTCACGAT CTGTACACGC
CTAGCTCCAG CGCGACCAAG CTGAGCGGCT ACACTTGGGA CATCTCCTAC
GGTGACGGCA GCTCGGCCAG CGGAGACGTG TACCGGGATA CTGTCACTGT
CGGCGGTGTC ACCACCAACA AGCAGGCTGT TGAAGCAGCC AGCAAGATCA
GCTCCGAGTT CGTTCAGAAC ACGGCCAATG ACGGCCTTTT GGGACTGGCC
TTTAGCTCCA TCAACACTGG TGAGTCAATC CTACATCAGC CGGGTTGACC
TACCTGCTGA CCGATACACA GTCCAGCCCA AGGCGCAGAC CACCTTCTTC
GACACCGTCA AGTCCCAGCT GGACTCTCCC CTTTTCGCCG TGCAGCTGAA
GCACGACGCC CCCGGTGTTT ACGACTTTGG CTACATCGAT GACTCCAAGT
ACACCGGTTC TATCACCTAC ACGGATGCCG ATAGCTCCCA GGGTTACTGG
GGCTTCAGCA CCGACGGCTA CAGTATCGGT GACGGCAGCT CCAGCTCCAG
CGGCTTCAGC GCCATTGCTG GTAAGAACCG CCTTCATTTA ACACACAACT
TGTCCACCTC TTTACTAACT AGTGTATAGA CACCGGTACC ACCCTCATCC
TCCTCGATGA CGAAATCGTC TCCGCCTACT ACGAGCAGGT TTCTGGCGCT
CAGGAGAGCG AGGAAGCCGG TGGCTACGTT TTCTCTTGCT CGACCAACCC
CCCTGACTTC ACTGTCGTGA TTGGCGACTA CAAGGCCGTT GTTCCGGGCA
AGTACATCAA CTACGCTCCC ATCTCGACTG GCAGCTCCAC CTGCTTTGGC
GGTATCCAGA GCAACAGCGG TCTGGGACTG TCCATCCTGG GTGATGTTTT
CTTGAAGAGC CAGTACGTGG TCTTCAACTC TGAGGGCCCT AAGCTGGGAT
TCGCCGCTCA GGCTTAGTCT AGAGTCGACC GCGACGGTGA CCGACACCTG
                     *** ***
                       XbaI
GCGGTAGACT ATTTATTCCT GTTGATATGA AGGATGAGCA TGAGGGTAAT
TGCTCATATA ATCATGTATG TAGTGGATGT GCATAAGAGC AACGAAATGG
AAGCCTGATC ATGTGATTGT ATTGCGACCG ACGGAATTGA GGATATGCGG
AGATACGGAC AGTGCCAGAG CCATTGTCTT CACGTAAAGT ACCAGACGGT
CCCTGATTTC TTCTTGCACA TAGCATTAGG CAATTGACAT GTTGTCGCTC
TACTGATATC ACTGTCCCTC AAAGCATAGC CATGAGCTCA TCTTAGATCC
AAGCACGTAA TTCCATAGCC GAGGTCCACA GTGGAGCAAC AGCAGCATCC
ATCATTGCTT CTCCCCCAGG GGCCTCTTAG CGACTAAACC TGGAGTATGT
CTCAACCAGC CAATGAATCG TCTTCGCTTC AATGTCCTTG ACACTTCTGA
GAGGGTCCCC ATCCCTCAAT GCTAATTCAA AATATAGCCG AGATGCATGG
TGGAGTCCAA AGTAGACAGT ATTGCCGGAA TGACGGGGCC AGTTGCGCCG
```

FIG. 12C

```
AGGTCATTGG CCGGCTGTGA TGCCATCTGC CACTAAATCC GATCATTGAT
CCACCGCCCA CGAGGGCCGT CTTTGCTTTT GCGCTGCGTC CAGGTTCACA
CATCTCTCTC TCTGCAGCTC CAGACTGACC AGACTATTCT ACTTACTGGT
CTGATCGGCT CCATCAGAGC TATGGCGTTA TCCCGTGCCG TTGCTGCGCC
ATCGCTATCT TGATCGCGAG CTCGAACTCA CTTCTTGTTT TAATAGTTGT
TCTCGGTGAC TGAGTGTCGG TGAGTGACAG ACCACAACAC CATTGTTGCA
GGGGGTAAAT TTATTCAATT CAGGAATTGG ATTGTTCGTC CGCCATGAT
GTTCTTGCCG GCTTTGTTGG CCCTGTTTGT CGGATGCGAC GCCCTCGCTG
TGCAGCAGGC AGGTACTGCT GGATGATGAG CCGTCGGTCT CCGCGCGCAA
GCCTAACTTC CTCTTCATTC TTACGGATGA TCAGGATCTG CAGATCGAAT
TCCACCGGCG TATATGCCGT ATACACAGGC GAGAATCAAG GAGAAGGGTA
CTGAGTTTTG AATCATTTGT TACTACTGGC TCTGTGCTGT CCGTCGCGCG
TGAGTCTTTG GACGGAAGAC AGGCTCATAA TACTAATGTG ACGGATGTGA
ACCCGCCTTA TGGTATGAAT ACCTCTCAGA TCGGTCATGT TTCTTCGGTG
TAAAATTGCT AATGCAGCAT AGGCGGATAC CCCAAGTTCG TCGCCCAAGG
CTTCAACGAA AACTTCCTCC CCGTTTGGCT GCAGTCCGCC GGTTACAATA
CCTTCTACAC GGGGAAACTG TTCAACTGCC ACAGCGTCGC TACCTATAAT
GCACCGTTTG TGAACGGCTT CAATGGCTCT GATTTCCTCC TCGATCCCCA
CACCTATTCC TACTGGAACG CGACGTACCA ACGAAACCAT GAGCCTCCGC
GGAGCTACGA GGGACAATAC ACAACGGATG TGATGCGGGA GAAGGCATCG
GGGTTGTTGG CAGATGCGCT GGACAGGACG CGCCGTTCTT CTGACGGTGC
CTATCCGCCG CACACGAACA TCGACCTGCA GGCATGCAAG CTTGGCACTG
GCCGTCGTTT TACAACGTCG TGACTGGGAA AACCCTGGCG TTACCCAACT
TAATCGCCTT GCAGCACATC CCCCTTTCGC CAGCTGGCGT AATAGCGAAG
AGGCCCGCAC CGATCGCCCT TCCCAACAGT TGCGCAGCCT GAATGGCGAA
TGGCGCCTGA TGCGGTATTT TCTCCTTACG CATCTGTGCG GTATTTCACA
CCGCATATGG TGCACTCTCA GTACAATCTG CTCTGATGCC GCATAGTTAA
GCCAGCCCCG ACACCCGCCA ACACCCGCTG ACGCGCCCTG ACGGGCTTGT
CTGCTCCCGG CATCCGCTTA CAGACAAGCT GTGACCGTCT CCGGGAGCTG
CATGTGTCAG AGGTTTTCAC CGTCATCACC GAAACGCGCG AGACGAAAGG
GCCTCGTGAT ACGCCTATTT TTATAGGTTA ATGTCATGAT AATAATGGTT
TCTTAGACGT CAGGTGGCAC TTTTCGGGGA AATGTGCGCG GAACCCCTAT
TTGTTTATTT TTCTAAATAC ATTCAAATAT GTATCCGCTC ATGAGACAAT
AACCCTGATA AATGCTTCAA TAATATTGAA AAAGGAAGAG TATGAGTATT
CAACATTTCC GTGTCGCCCT TATTCCCTTT TTTGCGGCAT TTTGCCTTCC
TGTTTTTGCT CACCCAGAAA CGCTGGTGAA AGTAAAAGAT GCTGAAGATC
AGTTGGGTGC ACGAGTGGGT TACATCGAAC TGGATCTCAA CAGCGGTAAG
ATCCTTGAGA GTTTTCGCCC CGAAGAACGT TTTCCAATGA TGAGCACTTT
TAAAGTTCTG CTATGTGGCG CGGTATTATC CCGTATTGAC GCCGGGCAAG
AGCAACTCGG TCGCCGCATA CACTATTCTC AGAATGACTT GGTTGAGTAC
TCACCAGTCA CAGAAAAGCA TCTTACGGAT GGCATGACAG TAAGAGAATT
ATGCAGTGCT GCCATAACCA TGAGTGATAA CACTGCGGCC AACTTACTTC
TGACAACGAT CGGAGGACCG AAGGAGCTAA CCGCTTTTTT GCACAACATG
GGGGATCATG TAACTCGCCT TGATCGTTGG GAACCGGAGC TGAATGAAGC
CATACCAAAC GACGAGCGTG ACACCACGAT GCCTGTAGCA ATGGCAACAA
```

*FIG. 12D*

```
CGTTGCGCAA ACTATTAACT GGCGAACTAC TTACTCTAGC TTCCCGGCAA
CAATTAATAG ACTGGATGGA GGCGGATAAA GTTGCAGGAC CACTTCTGCG
CTCGGCCCTT CCGGCTGGCT GGTTTATTGC TGATAAATCT GGAGCCGGTG
AGCGTGGGTC TCGCGGTATC ATTGCAGCAC TGGGGCCAGA TGGTAAGCCC
TCCCGTATCG TAGTTATCTA CACGACGGGG AGTCAGGCAA CTATGGATGA
ACGAAATAGA CAGATCGCTG AGATAGGTGC CTCACTGATT AAGCATTGGT
AACTGTCAGA CCAAGTTTAC TCATATATAC TTTAGATTGA TTTAAAACTT
CATTTTTAAT TTAAAAGGAT CTAGGTGAAG ATCCTTTTTG ATAATCTCAT
GACCAAAATC CCTTAACGTG AGTTTTCGTT CCACTGAGCG TCAGACCCCG
TAGAAAAGAT CAAAGGATCT TCTTGAGATC CTTTTTTTCT GCGCGTAATC
TGCTGCTTGC AAACAAAAAA ACCACCGCTA CCAGCGGTGG TTTGTTTGCC
GGATCAAGAG CTACCAACTC TTTTTCCGAA GGTAACTGGC TTCAGCAGAG
CGCAGATACC AAATACTGTC CTTCTAGTGT AGCCGTAGTT AGGCCACCAC
TTCAAGAACT CTGTAGCACC GCCTACATAC CTCGCTCTGC TAATCCTGTT
ACCAGTGGCT GCTGCCAGTG GCGATAAGTC GTGTCTTACC GGGTTGGACT
CAAGACGATA GTTACCGGAT AAGGCGCAGC GGTCGGGCTG AACGGGGGGT
TCGTGCACAC AGCCCAGCTT GGAGCGAACG ACCTACACCG AACTGAGATA
CCTACAGCGT GAGCTATGAG AAAGCGCCAC GCTTCCCGAA GGGAGAAAGG
CGGACAGGTA TCCGGTAAGC GGCAGGGTCG GAACAGGAGA GCGCACGAGG
GAGCTTCCAG GGGGAAACGC CTGGTATCTT TATAGTCCTG TCGGGTTTCG
CCACCTCTGA CTTGAGCGTC GATTTTTGTG ATGCTCGTCA GGGGGGCGGA
GCCTATGGAA AAACGCCAGC AACGCGGCCT TTTTACGGTT CCTGGCCTTT
TGCTGGCCTT TTGCTCACAT GTTCTTTCCT GCGTTATCCC CTGATTCTGT
GGATAACCGT ATTACCGCCT TTGAGTGAGC TGATACCGCT CGCCGCAGCC
GAACGACCGA GCGCAGCGAG TCAGTGAGCG AGGAAGCGGA AGAGCGCCCA
ATACGCAAAC CGCCTCTCCC CGCGCGTTGG CCGATTCATT AATGCAGCTG
GCACGACAGG TTTCCCGACT GGAAAGCGGG CAGTGAGCGC AACGCAATTA
ATGTGAGTTA GCTCACTCAT TAGGCACCCC AGGCTTTACA CTTTATGCTT
CCGGCTCGTA TGTTGTGTGG AATTGTGAGC GGATAACAAT TTCACACAGG
AAACAGCTAT GACCATGATT ACGAATTCGA GCTCGG
```

FIG. 12E

The Amino Acid Sequence of the L388M pepA (SEQ ID NO:7).

Met Val Val Phe Ser Lys Thr Ala Ala Leu Val Leu Gly Leu Ser Ser
Ala Val Ser Ala Ala Pro Ala Pro Thr Arg Lys Gly Phe Thr Ile Asn
Gln Ile Ala Arg Pro Ala Asn Lys Thr Arg Thr Ile Asn Leu Pro Gly
Met Tyr Ala Arg Ser Leu Ala Lys Phe Gly Gly Thr Val Pro Gln Ser
Val Lys Glu Ala Ala Ser Lys Gly Ser Ala Val Thr Thr Pro Gln Asn
Asn Asp Glu Glu Tyr Leu Thr Pro Val Thr Val Gly Lys Ser Thr Leu
His Leu Asp Phe Asp Thr Gly Ser Ala Asp Leu Trp Val Phe Ser Asp
Glu Leu Pro Ser Ser Glu Gln Thr Gly His Asp Leu Tyr Thr Pro Ser
Ser Ser Ala Thr Lys Leu Ser Gly Tyr Thr Trp Asp Ile Ser Tyr Gly
Asp Gly Ser Ser Ala Ser Gly Asp Val Tyr Arg Asp Thr Val Thr Val
Gly Gly Val Thr Thr Asn Lys Gln Ala Val Glu Ala Ala Ser Lys Ile
Ser Ser Glu Phe Val Gln Asn Thr Ala Asn Asp Gly Leu Leu Gly Leu
Ala Phe Ser Ser Ile Asn Thr Val Gln Pro Lys Ala Gln Thr Thr Phe
Phe Asp Thr Val Lys Ser Gln Leu Asp Ser Pro Leu Phe Ala Val Gln
Leu Lys His Asp Ala Pro Gly Val Tyr Asp Phe Gly Tyr Ile Asp Asp
Ser Lys Tyr Thr Gly Ser Ile Thr Tyr Thr Asp Ala Asp Ser Ser Gln
Gly Tyr Trp Gly Phe Ser Thr Asp Gly Tyr Ser Ile Gly Asp Gly Ser
Ser Ser Ser Ser Gly Phe Ser Ala Ile Ala Asp Thr Gly Thr Thr Leu
Ile Leu Leu Asp Asp Glu Ile Val Ser Ala Tyr Tyr Glu Gln Val Ser
Gly Ala Ser Gly Glu Thr Glu Ala Gly Gly Tyr Val Phe Ser Cys Ser
Thr Asn Pro Pro Asp Phe Thr Val Val Ile Gly Asp Tyr Lys Ala Val
Val Pro Gly Lys Tyr Ile Asn Tyr Ala Pro Ile Ser Thr Gly Ser Ser
Thr Cys Phe Gly Gly Ile Gln Ser Asn Ser Gly Leu Gly Leu Ser Ile
Leu Gly Asp Val Phe Leu Lys Ser Gln Tyr Val Val Phe Asn Ser Glu
Gly Pro Lys Met Gly Phe Ala Ala Gln Ala

FIG. 13

ACID FUNGAL PROTEASES

RELATED APPLICATIONS

The present application is a divisional application of U.S. patent application Ser. No. 12/582,606, filed Oct. 20, 2009, now U.S. Pat. No. 8,173,409, which is a continuation of U.S. patent application Ser. No. 12/167,092, filed Jul. 2, 2008, now U.S. Pat. No. 7,629,451, which is a continuation of U.S. patent application Ser. No. 11/312,290, filed Dec. 20, 2005, now U.S. Pat. No. 7,429,476, which claims the benefit of U.S. Provisional Patent Application No. 60/640,399, filed Dec. 30, 2004 and U.S. Provisional Patent Application No. 60/648,233, filed Jan. 27, 2005, the contents of which are fully incorporated herein by reference.

SEQUENCE LISTING

The sequence listing submitted via EFS, in compliance with 37 C.F.R. §1.52(e), is incorporated herein by reference. The sequence listing text file submitted via EFS contains the file "863-D1-SEQ-LIST.txt" created on Mar. 27, 2012, which is 46,822 bytes in size.

FIELD OF THE INVENTION

The invention relates to polynucleotides encoding acid proteases, designated NSP24 family proteases, NSP25 family proteases and PepA proteases; the NSP24 and NSP25 family protease polypeptides; compositions including said proteases and uses thereof.

BACKGROUND OF THE INVENTION

Proteases are enzymes capable of cleaving peptide bonds. Acid proteases (e.g., proteases having an acidic pH optimum) are produced by a number of different organisms including mammals and microbes. For instance, microbial acid proteases are produced by bacterial strains such as strains of *Bacillus* sp. (JP 01240184) and fungal strains, such as strains of *Rhizopus* sp. (EP 72978), *Schytalidium* sp. (JP 48091273), *Sulpholobus* sp., *Thermoplasma* sp. (WO/90 10072) and *Aspergillus* sp. (JP 50121486 and EP 82 395).

Berka et al. (Gene (1990) 96:313) disclose a gene encoding the aspartic proteinase aspergillopepsin A from *Aspergillus awamori*. The cloning of a gene encoding the aspartic proteinase aspergillopepsin O from *Aspergillus oryzae* is described by Berka et al. (Gene (1993) 125:195-198). The cloning of a gene encoding the acid protease (PepA) from *Aspergillus oryzae* is disclosed by Gomi et al. (Biosci. Biotech. Biochem. (1993) 57(7):1095-1100).

Proteases and particularly acid proteases are widely used in industrial applications, e.g., in the preparation of food and feed, in the leather industry (e.g., to dehair hides), in the production of protein hydrolysates, and in the production of alcohols, such as ethanol production, wine production and brewing.

Yet, there is a continuing need for proteases for many different applications, especially in the food and feed industry.

SUMMARY OF THE INVENTION

Applicants have discovered a number of novel protease genes, which include a novel nsp24 gene that encodes an NSP24 protease (SEQ ID NO: 2 or SEQ ID NO: 10); a novel nsp25 gene that encodes an NSP25 protease (SEQ ID NO: 9); and a novel pepA variant gene that encodes a novel PepA protease (SEQ ID NO: 7).

Accordingly, the invention features a recombinant or substantially pure preparation of an NSP24 protease, an NSP25 protease or a PepA protease and variants thereof.

In some aspects of the invention, the protease is an NSP24 family protease polypeptide which includes an amino acid sequence essentially the same as an amino acid sequence in SEQ ID NO: 2 or SEQ ID NO: 10 (illustrated in FIG. 6, infra). In some embodiments, an NSP24 family protease polypeptide is encoded by the nucleic acid in SEQ ID NO: 8 (illustrated in FIG. 5, infra), or by a nucleic acid having essentially the same nucleic acid sequence as with the nucleic acid from SEQ ID NO: 8.

In other aspects of the invention, the NSP24 family protease polypeptide differs in amino acid sequence at up to 10 residues, from a sequence in SEQ ID NO: 10. In some embodiments, the NSP24 family protease polypeptide differs in amino acid sequence at up to 10% of the residues from a sequence in SEQ ID NO: 10. In some embodiments, the differences are such that the NSP24 family protease polypeptide exhibits an NSP24 protease biological activity, e.g., the NSP24 protease retains a biological activity of a naturally occurring NSP24 protease.

In further aspects of the invention, the NSP24 family protease polypeptide includes a NSP24 protease sequence described herein as well as other N-terminal and/or C-terminal amino acid sequences.

In additional aspects of the invention, the NSP24 family protease polypeptide includes all or a fragment of an amino acid sequence from SEQ ID NO: 2 or SEQ ID NO: 10, fused, in reading frame, to additional amino acid residues, preferably to residues encoded by genomic DNA 5' to the genomic DNA which encodes a sequence from SEQ ID NO: 1 or SEQ ID NO: 8.

In yet other aspects of the invention, the NSP24 family protease is a recombinant fusion protein having a first NSP24 family protease portion and a second polypeptide portion, e.g., a second polypeptide portion having an amino acid sequence unrelated to an NSP24 family protease. The second polypeptide portion can be a DNA binding domain or a polymerase activating domain. Polypeptides of the invention include those which arise as a result of the existence of multiple genes, alternative transcription events, alternative RNA splicing events, and alternative translational and posttranslational events. The polypeptide can be expressed in systems, e.g., cultured cells, which result in substantially the same postranslational modifications present when expressed NSP24 protease is expressed in a native cell, or in systems which result in the omission of postranslational modifications present when expressed in a native cell.

In still other aspects, the invention relates to an enzyme composition, which includes a NSP24 family protease and one or more additional components, e.g., a carrier, diluent, or solvent. The additional component can be one, which renders the composition useful for in vitro, in vivo, pharmaceutical, or veterinary use. In some embodiments of this aspect, the enzyme composition will include additional enzymes. In preferred embodiments, the additional enzyme will be a glucoamylase, an alpha amylase or combinations thereof.

In yet a further aspect, the invention provides a substantially pure nucleic acid having or comprising a nucleotide sequence which encodes an NSP24 family protease polypeptide comprising an amino acid sequence having at least 80% sequence identity to the amino acid sequence of SEQ ID NO: 2 or SEQ ID NO: 10.

In some aspects, the NSP24 family protease nucleic acid will include a transcriptional regulatory sequence, e.g. at least one of a transcriptional promoter or transcriptional enhancer sequence, operably linked to the NSP24 family protease gene sequence, e.g., to render the NSP24 family protease gene sequence suitable for use as an expression vector.

In yet other aspects, the nucleic acid which encodes an NSP24 protease polypeptide of the invention (e.g., SEQ ID NO: 2), hybridizes under stringent conditions to a nucleic acid probe corresponding to at least 12 consecutive nucleotides from SEQ ID NO: 8, more preferably to at least 20 consecutive nucleotides from SEQ ID NO: 8.

Another aspect of the present invention provides for applications of an NSP24 family protease (e.g. NSP24) in a variety of industrial settings. For example, the NSP24 family protease may be used to enzymatically breakdown agricultural wastes for production of alcohol fuels and other important industrial chemicals, for production of animal or human foodstuffs, or as a component in a detergent composition, for leather processing and protein based fiber processing (such as wool or silk), for biomass applications, for personal care applications (skin, hair, oral care, etc.) for pharmaceutical and health care applications and for production of novel peptides for use in applications above.

In further aspects, the invention relates to polynucleotides encoding a pepA variant protease, L388M having SEQ ID NO: 7. In some embodiments, the polynucleotide has the sequence of SEQ ID NO: 5.

In yet another aspect, the invention relates to NSP25 family proteases. In some embodiments, the NSP25 family protease will have at least 85% sequence identity to SEQ ID NO: 9. In other embodiments the NSP25 family protease will be encoded by a polynucleotide having at least 85% sequence identity to SEQ ID NO: 4. In yet other embodiments the NSP25 family protease will be a biologically active fragment of a parent NSP25 family protease.

BRIEF DESCRIPTION OF THE DRAWINGS

FIG. 1 illustrates the sugar degradation (DP+3) % w/v using 1) NSP24, 2) a commercially available protease, GC106 and 3) DISTILLASE, which does not include a protease (see, Example 5).

FIG. 2 depicts sugar degradation (DP2) % w/v using NSP24, GC106 and DISTILLASE.

FIG. 3 illustrates glucose formation (DP1) using NSP24, GC106 and DISTILLASE. The amount of glucose remaining at the end of 40 hours is less than 0.2% w/v and less than 0.1% w/v at the end of 48 hours for both the NSP24 and GC106 samples. In contrast, the amount of glucose measured as % w/v at the end of 48 hours is slightly greater than 1.0% w/v for DISTILLASE.

FIG. 4 illustrates ethanol production (% v/v) for NSP24, GC106 and DISTILLASE. The rate and amount of ethanol produced by use of the two protease samples is essentially the same. In contrast, DISTILLASE produced less ethanol and at a slower rate.

FIGS. 5A-D illustrates the nucleotide sequence (SEQ ID NO: 1) of a pTrex3g_NSP24 cDNA clone obtained from *Trichoderma reesei*. The NSP24 gene sequence is underlined, and the putative gene intron sequence is identified in bolded format. The nucleic acid sequence which encodes the protease is represented by the sequence of SEQ ID NO: 8.

FIGS. 6A-B illustrates the predicted amino acid sequence (407 amino acids) (SEQ ID NO: 2) for NSP24 from *Trichoderma reesei* (FIG. 6A) and the NSP24 nucleotide sequence with the putative intron identified in bolded letters (FIG. 6B) (SEQ ID NO: 8). In FIG. 6A, the signal peptide is in bold, the prepro sequence is in bold and underlined and the mature NSP24 protein starts with KYGAPIS . . . and is represented by SEQ ID NO: 10.

FIG. 7 illustrates the pTrex3g_NSP24 vector and locations of restriction enzyme cleavage sites along the nucleotide sequence of FIG. 5.

FIG. 8 illustrates the nucleic acid sequence (SEQ ID NO: 3) for a pepA protease. The putative introns are in bold.

FIG. 9A-B illustrates the nucleic acid sequence (SEQ ID NO: 4) encoding a novel NSP25 protease (399 amino acids) (SEQ ID NO: 9). The signal sequence is in bold.

FIG. 10 illustrates the nucleic acid sequence (SEQ ID NO: 5) for a novel pepA protease variant (L388M) (SEQ ID NO: 7), wherein the underlined ‘A’ in the figure, is changed from a ‘C’ in pepA, in FIG. 8.

FIG. 11 illustrates the expression vector, pSL899_pepA.

FIGS. 12A-E illustrates the nucleotide sequence (SEQ ID NO: 6) of the expression vector pSL899_pepA. The Xho I cleavage site is indicated by A and the Xba I site is indicated by *. The coding sequence for pepA is shown in bold. The introns are underlined.

FIG. 13 illustrates the amino acid sequence of the PepA variant, L388M (SEQ ID NO: 7) for the protein encoded by SEQ ID NO: 5.

DETAILED DESCRIPTION OF THE INVENTION

The invention will now be described in detail by way of reference only using the following definitions and examples. All patents and publications, including all sequences disclosed within such patents and publications, referred to herein are expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); Ausubel et al., Eds *Short Protocols in Molecular Biology* ($5^{th}$ Ed. 2002); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986). Also, information regarding methods of preparation, expression, isolation and use of proteases may be obtained by review of U.S. Pat. No. 6,768,001, which is herein, in its entirety, incorporated by reference.

Other features and advantages of the invention will be apparent from the following detailed description, and from the claims. Although any methods and materials similar or equivalent to those described herein can be used in the practice or testing of the present invention, the preferred methods and materials are described.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with general dictionaries of many of the terms used in this invention.

The headings provided herein are not limitations of the various aspects or embodiments of the invention which can be had by reference to the specification as a whole. Accordingly, the terms defined immediately below are more fully defined by reference to the specification as a whole.

Numeric ranges are inclusive of the numbers defining the range.

Unless otherwise indicated, nucleic acids are written left to right in 5' to 3' orientation; amino acid sequences are written left to right in amino to carboxy orientation, respectively.

It should be noted that, as used in this specification and the appended claims, the singular forms "a," "an," and "the" include plural references unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Definitions—

"Protease" means a protein or polypeptide domain of a protein or polypeptide derived from a microorganism, e.g. a fungus, bacterium, or from a plant or animal, and that has the ability to catalyze cleavage of peptide bonds at one or more of various positions of a protein backbone (e.g. E.C. 3.4).

An "acid protease" refers to a protease having the ability to hydrolyze proteins under acid conditions.

As used herein, "NSP24 family protease" means an enzyme having protease activity in its native or wild type form, (e.g. the protein of FIG. 6), protease proteins having at least 50%, at least 60%, at least 70%, at least 80%, at least 85%, at least 90%, at least 93%, at least 95%, at least 97%, at least 98% and at least 99% sequence identity with the amino acid sequence of SEQ ID NO: 2 or SEQ ID NO: 10; a derivative of the amino acid sequence of SEQ ID NO: 2 or SEQ ID NO: 10, and biologically active fragments of a protease sequence.

As used herein, "derivative" means a protein which is derived from a precursor or parent protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence.

As used herein, a "native sequence NSP24" or "wildtype NSP24 sequence "includes a polypeptide having the same amino acid sequence as an NSP24 family protease derived from nature.

A "biologically active fragment" (e.g., a biologically active fragment of the NSP24 family protease having the sequence of SEQ ID NO: 10) means an NSP24 family protease or an NSP25 family protease, having protease activity but comprising less than the full sequence of a NSP24 family protease or NSP25 family protease precursor or parent protein.

The terms "isolated" or "purified" refers to a protease that is altered from its natural state by virtue of separating the protease from one or more or all of the naturally occurring constituents with which it is associated in nature.

"PepA" refers to an acid protease having at least 95% sequence identity to SEQ ID NO: 7.

"L388M" refers to a variant PepA having the sequence of SEQ ID NO: 7.

As used herein "NSP25 family protease" means a protease enzyme having at least 85% sequence identity to SEQ ID NO: 9 and biologically active fragments thereof.

"Unrelated to an NSP24 family protease" means having an amino acid sequence with less than 30% homology, less than 20% homology, or less than 10% homology with the NSP24 protease of SEQ ID NO: 10.

The terms "peptides", "proteins", and "polypeptides" are used interchangeably herein.

As used herein, "percent (%) sequence identity" with respect to the amino acid or nucleotides sequences identified is defined as the percentage of amino acid residues or nucleotides in a candidate sequence that are identical with the amino acid residues or nucleotides in a sequence of interest (e.g. a NSP24 family protease sequence), after aligning the sequences and introducing gaps, if necessary, to achieve the maximum percent sequence identity, and not considering any conservative substitutions as part of the sequence identity.

As used herein the term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Exemplary enzymes include alpha-1,4-glucan 4-glucanohydrase glucanohydrolase.

As used herein the term "glucoamylase" refers to the amyloglucosidase class of enzymes (e.g., EC.3.2.1.3, glucoamylase, 1,4-alpha-D-glucan glucohydrolase). These are exo-acting enzymes, which release glucosyl residues from the non-reducing ends of amylose and amylopectin molecules. The enzyme also hydrolyzes alpha-1,6 and alpha-1,3 linkages although at much slower rate than alpha-1,4 linkages.

The term "promoter" means a regulatory sequence involved in binding RNA polymerase to initiate transcription of a gene.

A "heterologous promoter", as used herein is a promoter which is not naturally associated with a gene or a purified nucleic acid.

A "purified preparation" or a "substantially pure preparation" of a polypeptide, as used herein, means a polypeptide that has been separated from cells, other proteins, lipids or nucleic acids with which it naturally occurs.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "substantially pure nucleic acid", e.g., a substantially pure DNA, is a nucleic acid which is one or both of: not immediately contiguous with either one or both of the sequences, e.g., coding sequences, with which it is immediately contiguous (e.g., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional NSP24 protease sequence.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein the term "vector" refers to a polynucleotide sequence designed to introduce nucleic acids into one or more cell types. Vectors include cloning vectors, expression vectors, shuttle vectors, plasmids, phage particles, cassettes and the like.

As used herein, "expression vector" means a DNA construct including a DNA sequence which is operably linked to a suitable control sequence capable of affecting the expression of the DNA in a suitable host.

The term "expression" means the process by which a polypeptide is produced based on the nucleic acid sequence of a gene.

As used herein, "operably linked" means that a regulatory region, such as a promoter, terminator, secretion signal or enhancer region is attached to or linked to a structural gene and controls the expression of that gene.

As used herein, a substance (e.g. a polynucleotide or protein) "derived from" a microorganism means that the substance is native to the microorganism.

As used herein, "microorganism" refers to a bacterium, a fungus, a virus, a protozoan, and other microbes or microscopic organisms.

As used herein, "host strain" or "host cell" means a suitable host for an expression vector including DNA according to the present invention and includes progeny of said cells.

The term "filamentous fungi" refers to all filamentous forms of the subdivision Eumycotina (See, Alexopoulos, C. J. (1962), INTRODUCTORY MYCOLOGY, Wiley, New York and AINSWORTH AND BISBY DICTIONARY OF THE FUNGI, 9$^{th}$ Ed. (2001) Kirk et al., Eds., CAB International University Press, Cambridge UK). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

As used herein, the term "*Trichoderma*" or "*Trichoderma* sp.*" refer to any fungal genus previously or currently classified as *Trichoderma*.

As used herein the term "quad-delete" or "quad-deleted" host cells, refers to both the cells and protoplasts created from the cells of a *Trichoderma* host strain that lacks at least two genes coding for functional endoglucanases and at least two genes coding for functional cellobiohydrolases.

As used herein the term "culturing" refers to growing a population of microbial cells under suitable conditions in a liquid or solid medium. In one embodiment, culturing refers to fermentative bioconversion of a starch substrate, such as a substrate comprising granular starch, to an end-product (typically in a vessel or reactor). Fermentation is the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

As used herein the term "contacting" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein the term "heterologous" with reference to a polypeptide or polynucleotide means a polypeptide or polynucleotide that does not naturally occur in a host cell.

The term "overexpression" means the process of expressing a polypeptide in a host cell wherein a polynucleotide has been introduced into the host cell.

As described herein, one aspect of the invention features a "substantially pure" (or recombinant) nucleic acid that includes a nucleotide sequence encoding a NSP24 family protease or a NSP25 family protease, and/or equivalents of such nucleic acids.

The term "equivalent" refers to nucleotide sequences encoding functionally equivalent polypeptides. Equivalent nucleotide sequences will include sequences that differ by one or more nucleotide substitutions, additions or deletions, such as allelic variants. For example in some embodiments, due to the degeneracy of the genetic code equivalent nucleotide sequences include sequences that differ from the nucleotide sequence of SEQ ID NO: 8, which encodes the NSP24 protease shown in SEQ ID NO: 2.

As used herein the term "saccharification" refers to enzymatic conversion of starch to glucose.

As used herein "starch" refers to any material comprised of the complex polysaccharide carbohydrates of plants comprised of amylase and amylopectin with the formula $(C_6H_{10}O_5)_x$, wherein X can be any number.

The term "granular starch" refers to uncooked (raw) starch (e.g. starch that has not been subject to gelatinization).

As used herein the term "gelatinization" means solubilization of a starch molecule by cooking to form a viscous suspension.

As used herein the term "liquefaction" refers to the stage in starch conversion in which gelatinized starch is hydrolyzed to give low molecular weight soluble dextrins.

As used herein the term "soluble starch hydrolyzate" refers to soluble products resulting from starch hydrolysis, which may comprise mono-, di-, and oligosaccharides (e.g. glucose, maltose and higher sugars).

The term "monosaccharide" means a monomeric unit of a polymer such as starch wherein the degree of polymerization (DP) is 1 (e.g., glucose, mannose, fructose and galactose).

The term "disaccharide" means a compound that comprises two covalently linked monosaccharide units (DP2) (e.g., sucrose, lactose and maltose).

The term "DP3+" means polymers with a degree of polymerization greater than 3.

Proteases and Polynucleotides Encoding the Same—

The invention relates to NSP24 family proteases, such as an acid protease and also an acid fungal protease, having at least 50%, at least 60%, at least 70%, at least 80%, at least 85%, at least 90%, at least 93%, at least 95%, at least 97%, at least 98% and at least 99% sequence identity to the protease of SEQ ID NO: 2 or the protease of SEQ ID NO: 10 (FIG. 6). In some embodiments, the NSP24 family protease is designated NSP24 comprising the sequence of SEQ ID NO: 10 (the mature protein sequence) or also the preprotein sequence of SEQ ID NO: 2.

In some embodiments, the invention relates to biologically active fragments of an NSP24 family protease. In some embodiments, biologically active fragments include proteases having at least 250 amino acid residues, at least 300 amino acid residues, at least 350 amino acid residues, at least 375 amino acid residues, and also at least 400 amino acid residues.

In other embodiments, biologically active fragments include at least 60%, at least 70%, at least 80%, at least 85%, at least 90%, at least 93%, at least 95%, at least 97%, at least 98%, at least 99% of a polypeptide sequence having at least 80%, at least 85%, at least 90%, at least 93%, at least 95%, at least 97%, at least 98% and at least 99% sequence identity with the protein sequence in FIG. 6 (SEQ ID NO: 2 or SEQ ID NO: 10). In some embodiments, a biologically active fragment will comprise at least 60%, at least 70%, at least 80%, at least 85%, at least 90%, at least 95% and at least 98% of a polypeptide sequence having at least 95% sequence identity to the parent NSP24 protease having SEQ ID NO: 2 or SEQ ID NO: 10. In some embodiments, a biologically active fragment will comprise at least 60%, at least 70%, at least 80%, at least 85%, at least 90%, at least 95% and at least 98% of a polypeptide sequence having at least 99% sequence identity to the parent NSP24 protease having SEQ ID NO: 2 or SEQ ID NO: 10.

In some embodiments, biologically active fragments are fragments that exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Some preferred fragments are fragments, e.g., active fragments, which are generated by proteolytic cleavage or alternative splicing events. Because peptides, such as an NSP24 family protease often exhibit a range of physiological properties and because such properties may be attributable to different portions of the molecule, a useful NSP24 family protease fragment or NSP24 family protease analog is one which exhibits a biological activity in any biological assay for NSP24 protease activity.

In some embodiments, a biologically active fragment will comprise at least 20%, at least 30%, at least 40%, at least 50%, at least 60%, at least 70%, at least 80%, at least 90%, at least 95%, and at least 100% of the protease activity of the NSP24 having SEQ ID NO: 2 or SEQ ID NO: 10. In some preferred embodiments, a fragment or analog possesses at least 40% or at least 90% of the protease activity of NSP24 protease (SEQ ID NO: 2 or SEQ ID NO: 10), in any in vivo or in vitro NSP24 protease assay.

Fragments of an NSP24 family protease or an NSP25 family protease can be generated by methods known to those skilled in the art. The ability of a candidate fragment to exhibit a biological activity of a protease can be assessed by methods known to those skilled in the art as described herein. Also included are NSP24 family proteases and NSP25 family protease containing residues that are not required for biological activity of the peptide or that result from alternative mRNA splicing or alternative protein processing events.

In some embodiments, the protease encompassed by the invention is a derivative of a protease having SEQ ID NO: 2 or SEQ ID NO: 10. A derivative may have at least 80%, 85%, 90%, 93%, 95%, 97%, 98% and 99% sequence identity to SEQ ID NO: 10.

The invention also includes protease analogs. The analogs are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., b or amino acids; and cyclic analogs. Analogs can differ from naturally occurring proteases, such as an NSP24 or NSP25 protein, in amino acid sequence or in ways that do not involve sequence, or both. Non-sequence modifications include in vivo or in vitro chemical derivatization of the proteases encompassed by the invention. Non-sequence modifications include changes in acetylation, methylation, phosphorylation, carboxylation, or glycosylation. In further embodiments, the invention includes NSP25 family proteases. NSP25 family proteases are acid proteases having at least 85%, at least 90%, at least 93%, at least 95%, at least 97%, at least 98%, and at least 99% amino acid sequence identity to the mature protein sequence of SEQ ID NO: 9 (FIG. 9) or biologically active fragments thereof. One specific NSP25 family protease is the protease designated NSP25 having SEQ ID NO: 9. In some embodiments, a NSP25 family protease will be a biologically active fragment of a protease comprising at least 75%, at least 80%, at least 85%, at least 90% and at least 95% of a sequence having at least 90% sequence identity to SEQ ID NO: 9. In other embodiments, an NSP25 family protease will be a biologically active fragment of a protease comprising at least 75%, at least 80%, at least 85%, at least 90% and at least 95% of a sequence having at least 95% sequence identity to SEQ ID NO: 9.

While an acid protease according to the invention is one able to hydrolyze proteins under acid conditions, in some embodiments an optimum pH for protease activity is in the range of pH 3.0 to 5.5. In some embodiments, the optimum pH range for protease activity is between pH 3.0 and 5.0 and in other embodiments the optimum pH range for protease activity is between pH 3.0 and 4.5.

A protease according to the invention, such as an NSP24 family protease or an NSP25 family protease may include an amino acid substitution such as a "conservative amino acid substitution" using L-amino acids, wherein one amino acid is replaced by another biologically similar amino acid. Conservative amino acid substitutions are those that preserve the general charge, hydrophobicity/hydrophilicity, and/or steric bulk of the amino acid being substituted. Examples of conservative substitutions are those between the following groups: Gly/Ala, Val/Ile/Leu, Lys/Arg, Asn/Gln, Glu/Asp, Ser/Cys/Thr, and Phe/Trp/Tyr. A derivative may, for example, differ by as few as 1 to 10 amino acid residues, such as 6-10, as few as 5, as few as 4, 3, 2, or even 1 amino acid residue. Table 1 illustrates exemplary amino acid substitutions that are recognized in the art. In addition, substitution may be by one or more non-conservative amino acid substitutions, deletions, or insertions that do not abolish the protease biological activity.

TABLE 1

CONSERVATIVE AMINO ACID REPLACEMENTS

| For Amino Acid | Code | Replace with any of |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3, 4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In some embodiments, the proteases of the invention are native sequences. Such a native sequence can be isolated from nature or can be produced by recombinant or synthetic means. The term "native sequence" specifically encompasses naturally-occurring truncated or secreted forms of an NSP24 or NSP25 family protease (e.g., biologically active fragments), and naturally-occurring variant forms (e.g., alternatively spliced forms).

In some embodiments, an acid protease of the invention is a PepA protease having at least 97%, at least 98%, and at least 99% sequence identity to SEQ ID NO: 7. In some embodiments, the protease has the sequence of SEQ ID NO: 7 and is designated "L388M. In further embodiments, the protease is encoded by a nucleotide sequence having the sequence of SEQ ID NO: 5 or SEQ ID NO: 3.

The invention also relates to polynucleotide sequences encoding proteases encompassed by the invention. Some of these polynucleotides include:

a) polynucleotides encoding an NSP24 family protease having at least 80% at least 85%, at least 90%, at least 93%, at least 95%, at least 97%, at least 98%, and at least 99% sequence identity to SEQ ID NO: 2 or SEQ ID NO: 10;

b) polynucleotides encoding the sequence of SEQ ID NO: 2;

c) a polynucleotide having the sequence of SEQ ID NO: 8;

d) polynucleotides encoding a biologically active fragment of an NSP24 family protease;

e) polynucleotides which have at least 80%, at least 85%, at least 90%, at least 95%, at least 97%, at least 98% and at least 99% sequence identity to the sequence of SEQ ID NO:8;

f) polynucleotides which hybridizes to a nucleic acid probe corresponding to the DNA sequence of SEQ ID NO: 4, SEQ ID NO: 8 or a fragment of SEQ ID NO: 4 or SEQ ID NO: 8, said fragment having at least 10, 15, 20, 30, 40, 50, 60, 70, 80, 90, 100 or 150 consecutive nucleotides;

g) polynucleotides encoding a NSP25 family protease having at least 85%, at least 90%, at least 93%, at least 95%, at least 97%, at least 98%, and at least 99% sequence identity to SEQ ID NO: 4;

h) polynucleotides encoding the protease of SEQ ID NO: 9;

i) a polynucleotide having the sequence of SEQ ID NO: 4;

j) polynucleotides encoding a biologically active fragment of NSP25 family proteases;

k) polynucleotides encoding the sequence of SEQ ID NO: 7 and biologically active fragments thereof; and l) a polynucleotide having the sequence of SEQ ID NO: 3 or SEQ ID NO: 5.

Because of the degeneracy of the genetic code, more than one codon may be used to code for a particular amino acid. Therefore different DNA sequences may encode a polypeptide having the same amino acid sequence as the polypeptide of, for example SEQ ID NO: 2. The present invention encompasses polynucleotides which encode the same polypeptide.

A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art for hydridization under low, medium, high and very high stringency conditions (See, e.g., Sambrook (1989) supra, particularly chapters 9 and 11). In general hybridization involves a nucleotide probe and a homologous DNA sequence that from stable double stranded hybrids by extensive base-pairing of complementary polynucleotides (Also see, Chapter 8, Gene Cloning, An Introduction, T. A. Brown (1995) Chapman and Hall London). In some embodiments the filter with the probe and homologous sequence may be washed in 2× sodium chloride/sodium citrate (SSC), 0.5% SDS at about 60° C. (medium stringency), 65° C. (medium/high stringency), 70° C. (high stringency) and about 75° C. (very high stringency) (Current Protocols in Molecular Biology, John Wiley & Sons, New York, 1989, 6.3.1-6.3.6, hereby incorporated by reference);

Included in the invention are: allelic variations; natural mutants; induced mutants; proteins encoded by DNA that hybridizes under high or low stringency conditions to a nucleic acid which encodes a polypeptide of SEQ ID NO: 2, SEQ ID NO: 8, SEQ ID NO: 9 and SEQ ID NO: 10 and polypeptides specifically bound by antisera to an NSP24 protease having SEQ ID NO: 2 or SEQ ID NO: 10, especially by antisera to an active site or binding domain of NSP24 protease. In some embodiments, a nucleic acid which encodes a NSP24 family protease of the invention, such as the nucleic acid which encodes the NSP24 protease of SEQ ID NO: 2, hybridizes under high stringency conditions to a nucleic acid corresponding to at least 12, 15 or 20 consecutive nucleotides from SEQ ID NO: 8.

Nucleic acids and polypeptides of the invention include those that differ from the sequences disclosed herein by virtue of sequencing errors in the disclosed sequences.

Homology of DNA sequences is determined by the degree of identity between two DNA sequences. Homology or percent identity may be determined for polypeptide sequences or nucleotides sequences using computer programs. Methods for performing sequence alignment and determining sequence identity are known to the skilled artisan, may be performed without undue experimentation, and calculations of identity values may be obtained with definiteness. See, for example, Ausubel et al., eds. (1995) Current Protocols in Molecular Biology, Chapter 19 (Greene Publishing and Wiley-Interscience, New York); and the ALIGN program (Dayhoff (1978) in Atlas of Protein Sequence and Structure 5:Suppl. 3 (National Biomedical Research Foundation, Washington, D.C.). A number of algorithms are available for aligning sequences and determining sequence identity and include, for example, the homology alignment algorithm of Needleman et al. (1970) J. Mol. Biol. 48:443; the local homology algorithm of Smith et al. (1981) Adv. Appl. Math. 2:482; the search for similarity method of Pearson et al. (1988) Proc. Natl. Acad. Sci. 85:2444; the Smith-Waterman algorithm (Meth. Mol. Biol. 70:173-187 (1997); and BLASTP, BLASTN, and BLASTX algorithms (see Altschul et al. (1990) J. Mol. Biol. 215:403-410). Computerized programs using these algorithms are also available, and include, but are not limited to: ALIGN or Megalign (DNASTAR) software, or WU-BLAST-2 (Altschul et al., Meth. Enzym., 266:460-480 (1996)); or GAP, BESTFIT, BLAST Altschul et al., supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can be determined by the Smith-Waterman homology search algorithm (Meth. Mol. Biol. 70:173-187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum62 amino acid substitution matrix, with a gap weight of 12 and a length weight of 2. With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for increased sequence identity associated with inclusion of gaps in the derivative's amino acid sequence can be made by assigning gap penalties.

In some embodiments, the proteases encompassed by the invention (e.g. an NSP24 family protease having at least 80% sequence identity to the sequence of SEQ ID NO: 2), is derived from a bacterium or a fungus, such as a filamentous fungus. Some preferred filamentous fungi include *Aspergillus* spp. and *Trichoderma* spp. One preferred *Trichoderma* spp. is *T. reesei*. However, the proteases and/or DNA encoding the proteases according to the instant invention may be derived from a fungus, such as, *Absidia* spp.; *Acremonium* spp.; *Agaricus* spp.; *Anaeromyces* spp.; *Aspergillus* spp., including *A. aculeatus, A. awamori, A. flavus, A. foetidus, A. fumaricus, A. fumigatus, A. nidulans, A. niger, A. oryzae, A. terreus* and *A. versicolor; Aeurobasidium* spp.; *Cephalosporum* spp.; *Chaetomium* spp.; *Coprinus* spp.; *Dactylium* spp.; *Fusarium* spp., including *F. conglomerans, F. decemcellulare, F. javanicum, F. lini, F. oxysporum* and *F. solani; Gliocladium* spp.; *Humicola* spp., including *H. insolens* and *H. lanuginosa; Mucor* spp.; *Neurospora* spp., including *N. crassa* and *N. sitophila; Neocallimastix* spp.; *Orpinomyces* spp.; *Penicillium* spp; *Phanerochaete* spp.; *Phlebia* spp.; *Piromyces* spp.; *Rhizopus* spp.; *Schizophyllum* spp.; *Trametes* spp.; *Trichoderma* spp., including *T. reesei, T. reesei* (longibrachiatum) and *T. viride;* and *Zygorhynchus* spp.

Host Cells—

In some embodiments, this invention provides for host cells transformed with DNA constructs and vector as described herein. In some embodiments, a polynucleotide encoding a protease encompassed by the invention (e.g. a NSP24 family protease having at least 95% sequence identity to SEQ ID NO: 2) that is introduced into a host cell codes for a heterologous protease and in other embodiments the polynucleotide codes for an endogenous protease which is overexpressed in the host cell. In some embodiments the invention provides for the expression of heterologous protease genes or overexpression of protease genes under control of gene promoters functional in host cells such as bacterial and fungal host cells.

Some preferred host cells include filamentous fungal cells. Non-limiting examples of filamentous fungal host cells include *Trichoderma* spp. (e.g. *T. viride* and *T. reesei*, the asexual morph of *Hypocrea jecorina*, previously classified as *T. longibrachiatum*), *Penicillium* spp., *Humicola* spp. (e.g. *H. insolens* and *H. grisea*), *Aspergillus* spp. (e.g., *A. niger, A. nidulans, A. orzyae,* and *A. awamori*), *Fusarium* spp. (*F. graminum*), *Neurospora* spp., *Hypocrea* spp. and *Mucor* spp. Further host cells may include *Bacillus* spp (e.g. *B. subtilis, B. licheniformis, B. lentus, B. stearothremophilus* and *B. brevis*) and *Streptomyces* spp. (e.g., *S coelicolor* and *S. lividans* (TK23 and TK21)).

Molecular Biology—

This invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Ausubel et al., eds., Current Protocols in Molecular Biology (1994)).

Heterologous genes comprising gene promoter sequences for example of filamentous fungi are typically cloned into intermediate vectors before transformation into host cells, such as *Trichoderma reesei* cells for replication and/or expression. These intermediate vectors are typically prokaryotic vectors, e.g., plasmids, or shuttle vectors.

To obtain high level expression of a cloned gene, the heterologous gene is preferably positioned about the same distance from the promoter as is in the naturally occurring gene. As is known in the art, however, some variation in this distance can be accommodated without loss of promoter function.

Those skilled in the art are aware that a natural promoter can be modified by replacement, substitution, addition or elimination of one or more nucleotides without changing its function. The practice of the invention encompasses and is not constrained by such alterations to the promoter.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites. The practice of the invention is not constrained by the choice of promoter in the genetic construct. However, exemplary promoters are the *Trichoderma reesei* cbh1, cbh2, eg1, eg2, eg3, eg5, xln1 and xln2 promoters. Also promoters from *A. awamori* and *A. niger* glucoamylase genes (glaA) (Nunberg et al., (1984) *Mol. Cell. Biol.* 4:2306-2315) and the promoter from *A. nidulans* acetamidase find use in the vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* is cbhl.

In addition to a promoter sequence, the expression cassette should also contain a transcription termination region downstream of the structural gene to provide for efficient termination. The termination region may be obtained from the same gene as the promoter sequence or may be obtained from different genes.

Although any fungal terminator is likely to be functional in the present invention, some preferred terminators include: the terminator from *Aspergillus nidulans* trpC gene (Yelton, M. et al. (1984) PNAS USA 81:1470-1474, Mullaney, E. J. et al. (1985) MGG 199:37-45), the *Aspergillus awamori* or *Aspergillus niger* glucoamylase genes (Nunberg, J. H. et al. (1984) Mol. Cell Biol. 4:2306, Boel, E. et al. (1984) EMBO J. 3:1581-1585), the *Aspergillus oryzae* TAKA amylase gene, and the *Mucor miehei* carboxyl protease gene (EPO Publication No. 0 215 594).

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Examples of suitable expression and/or integration vectors are provided in Sambrook et al., (1989) supra, Bennett and Lasure (Eds.) More Gene Manipulations in Fungi, (1991) Academic Press pp. 70-76 and pp. 396-428 and articles cited therein; U.S. Pat. No. 5,874,276 and Fungal Genetic Stock Center Catalogue of Strains, (FGSC, www.fgsc.net.). Useful vectors may be obtained from Promega and Invitrogen. Some specific useful vectors include pBR322, pUC18, pUC100, pDON™201, pENTR™, pGEN®3Z and pGEN®4Z. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC19 and their derivatives, wider host range plasmids, e.g., RP4, phage DNAs e.g., the numerous derivatives of phage .lambda., e.g., NM989, and other DNA phages, e.g., M13 and filamentous single stranded DNA phages, yeast plasmids such as the 2.mu plasmid or derivatives thereof.

In some embodiments, an expression vector includes a selectable marker. Examples of selectable markers include ones which confer antimicrobial resistance. Nutritional markers also find use in the present invention including those markers known in the art as amdS, argB and pyr4. Markers useful for the transformation of *Trichoderma* are known in the art (see, e.g., Finkelstein, chapter 6, in Biotechnology of Filamentous Fungi, Finkelstein et al., EDS Butterworth-Heinemann, Boston Mass. (1992) and Kinghorn et al., (1992) Applied Molecular Genetics of Filamentous Fungi, Blackie Academic and Professional, Chapman and Hall, London). In some embodiments, the expression vectors will also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication or integration of the DNA in *Trichoderma reesei*.

The methods of transformation of the present invention may result in the stable integration of all or part of the transformation vector into the genome of a host cell, such as a filamentous fungal host cell. However, transformation resulting in the maintenance of a self-replicating extra-chromosomal transformation vector is also contemplated.

Many standard transfection methods can be used to produce bacterial and filamentous fungal (e.g. *Aspergillus* or *Trichoderma*) cell lines that express large quantities of the protease. Some of the published methods for the introduction of DNA constructs into cellulase-producing strains of *Trichoderma* include Lorito, Hayes, DiPietro and Harman, (1993) Curr. Genet. 24: 349-356; Goldman, VanMontagu and Herrera-Estrella, (1990) Curr. Genet. 17:169-174; and Penttila, Nevalainen, Ratto, Salminen and Knowles, (1987) Gene 6: 155-164, also see U.S. Pat. No. 6,022,725; U.S. Pat. No. 6,268,328 and Nevalainen et al., "The Molecular Biology of *Trichoderma* and its Application to the Expression of Both Homologous and Heterologous Genes" in Molecular Industrial Mycology, Eds, Leong and Berka, Marcel Dekker Inc., NY (1992) pp 129-148; for *Aspergillus* include Yelton, Hamer and Timberlake, (1984) Proc. Natl. Acad. Sci. USA 81: 1470-1474, for *Fusarium* include Bajar, Podila and Kolattukudy, (1991) Proc. Natl. Acad. Sci. USA 88: 8202-8212, for *Streptomyces* include Hopwood et al., 1985, Genetic Manipulation of *Streptomyces*: Laboratory Manual, The John Innes Foundation, Norwich, UK and Fernandez-Abalos et al., Microbiol 149:1623-1632 (2003) and for *Bacillus* include Brigidi, DeRossi, Bertarini, Riccardi and Matteuzzi, (1990) FEMS Microbiol. Lett. 55: 135-138).

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the gene. In one embodiment, the invention concerns a method for producing a protease encompassed by the invention (e.g. an NSP 24 family protease) which comprises introducing into a host cell a polynucleotide comprising a promoter operably linked to a nucleic acid encoding a protease, such as a NSP family protease, culturing the host cell under suitable culture conditions for the expression and production of the protease, and producing said protease. In some preferred embodiments, the protease is a NSP24 family protease having at least 95% sequence identity to SEQ ID NO: 2 or SEQ ID NO: 10 or biologically active fragments thereof.

After the expression vector is introduced into the cells, the transfected or transformed cells are cultured under conditions favoring expression of genes under control of protease gene promoter sequences. Large batches of transformed cells can be cultured as described in Example 3, infra. Finally, product is recovered from the culture using standard techniques.

Thus, the invention herein provides for the expression and enhanced secretion of desired polypeptides whose expression is under control of gene promoter sequences including naturally occurring protease genes, fusion DNA sequences, and various heterologous constructs. The invention also provides processes for expressing and secreting high levels of such desired polypeptides.

Protein Expression

Proteins of the present invention are produced by culturing cells transformed with a vector such as an expression vector containing genes whose expression is under control of gene promoter sequences. The present invention is particularly useful for enhancing the intracellular and/or extracellular production of proteins, such as proteases encompassed by the invention. The protein may be homologous or heterologous. Conditions appropriate for expression of said genes comprise providing to the culture an inducing feed composition of the instant invention. Optimal conditions for the production of the proteins will vary with the choice of the host cell, and with the choice of protease protein to be expressed. Such conditions will be easily ascertained by one skilled in the art through routine experimentation or optimization.

The protease protein of interest is may be isolated or recovered and purified after expression. The protein of interest may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard anti-protein of interest antibody column. Ultrafiltration and diafiltration techniques, in conjunction with protein concentration, are also useful. For general guidance in suitable purification techniques, see Scopes, Protein Purification (1982). The degree of purification necessary will vary depending on the use of the protein of interest. In some instances no purification will be necessary.

Cell Culture

Host cells and transformed cells can be cultured in conventional nutrient media. The culture media for transformed host cells may be modified as appropriate for activating promoters and selecting transformants. The specific culture conditions, such as temperature, pH and the like, may be those that are used for the host cell selected for expression, and will be apparent to those skilled in the art. In addition, preferred culture conditions may be found in the scientific literature such as Sambrook, (1982) supra; Kieser, T, M J. Bibb, M J. Buttner, K F Chater, and D. A. Hopwood (2000) PRACTICAL STREPTOMYCES GENETICS. John Innes Foundation, Norwich UK; Harwood, et al., (1990) MOLECULAR BIOLOGICAL METHODS FOR BACILLUS, John Wiley and/or from the American Type Culture Collection (ATCC; www.atcc.org). Stable transformants of fungal host cells, such as *Trichoderma* cells can generally be distinguished from unstable transformants by their faster growth rate or the formation of circular colonies with a smooth rather than ragged outline on solid culture medium.

Recovery of Expressed Polypeptides and Methods for Purifying the Proteases—

A polypeptide encompassed by the invention, such as a polypeptide having at least 80% sequence identity to SEQ ID NO: 10, produced by the transformed host cell may be recovered from the culture medium by conventional procedures including separating the host cells from the medium by centrifugation or filtration, or if necessary, disrupting the cells and removing the supernatant from the cellular fraction and debris. In some cases, after clarification, the proteinaecous components of the supernatant or filtrate are precipitated by means of a salt, e.g., ammonium sulphate. The precipitated proteins are then solubilized and may be purified by a variety of chromatographic procedures, e.g., ion exchange chromatography, gel filtration chromatography, affinity chromatography, and other art-recognized procedures. Antibodies to the peptides and proteins can be made by immunizing an animal, e.g., a rabbit or mouse, and recovering anti-NSP24 protease antibodies by prior art methods.

Assays that find use in the present invention include, but are not limited to those described in WO 9934011 and U.S. Pat. No. 6,605,458.

Compositions and Applications—

In some embodiments, the present invention is directed to compositions comprising a protease of the invention as described herein. Some non-limiting examples of proteases useful in compositions and applications according to the invention include for example an NSP24 family protease or a NSP25 family protease, more specifically an NSP24 family protease having at least 85% sequence identity to SEQ ID NO: 2 or biologically active fragments thereof, such as a protease having at least 90% sequence identity to the sequence of SEQ ID NO: 10. In some embodiments, the enzyme composition is a single-component protease composition. In some embodiments, the present invention is directed to methods of using the proteases of the invention in industrial and commercial applications. The following description of compositions and industrial applications is intended to be exemplary and non-inclusive.

Compositions comprising proteases of the invention may further include additional enzymes, such as, but not limited to, glucoamylases, alpha amylases, granular starch hydrolyzing enzymes, cellulases, lipases, xylanases, cutinases, hemicellulases, oxidases and combinations thereof.

In some preferred embodiments, the compositions will include a protease of the invention having at least 85% sequence identity to the sequence of SEQ ID NO: 10 and a glucoamylase. The glucoamylase may be a wild type glucoamylase obtained from a filamentous fungal source, such as a strain of *Aspergillus, Trichoderma* or *Rhizopus* or the glucoamylase may be a protein engineered glucoamylase, such as a variant of an *Aspergillus niger* glucoamylase. In other preferred embodiments, a composition will include a protease of the invention and an alpha amylase. In some embodiments, the alpha amylase may be obtained from a bacterial source such as a *Bacillus* spp or from a fungal source such as an *Aspergillus* spp. In some embodiments, the compositions may include a protease according to the invention and both glucoamylase and alpha amylase enzymes. Commercially sources of these enzymes are known and available from, for example Genencor International, Inc. and Novozymes A/S.

In several embodiments, the present invention has contemplated use in ethanol production, baking, fruit juice production, brewing, distilling, wine making, leather, oils and fats, paper and pulp and the animal feed production.

In other embodiments, the present invention as contemplated is the active "biological" component of detergents and cleaning products. Here, proteases, amylases and lipases are used to break down protein, starch and fatty stains. Embodiments of the invention include testing the compatibility of enzymes with detergent ingredients by doing stability studies and testing them in a variety of formulations.

In yet another embodiment, the present invention has contemplated enzymatic uses for the liquefaction and saccharification of starch into glucose and isomerisation into fructose. The present invention may be used to convert large volumes of plant substrates, such as grains, (e.g. corn, wheat, milo, rye and the like) into sweeteners, like high fructose corn syrup and maltose syrup.

The enzyme(s) of the instant invention has application in the food and feed industry to improve the digestibility of proteins. The proteases also find uses in various industrial applications, particularly in the textile, lithographic, chemical arts, agriculture, environmental waste conversion, biopulp processing, biomass conversion to fuel, and other chemical procedure(s). Further, the proteases have applications, which find use in healthcare and personal care products such as cosmetics, skin care, toothpaste and the like.

Feed—

The present enzymes described herein find use in animal feeds. The feeds may include plant material such as corn, wheat, sorghum, soybean, canola, sunflower or mixtures of any of these plant materials or plant protein sources for poultry, pigs, ruminants, aquaculture and pets. It is contemplated that the performance parameters, such as growth, feed intake and feed efficiency, but also improved uniformity, reduced ammonia concentration in the animal house and consequently improved welfare and health status of the animals will be improved.

Food—

Dietary protein hydrolysates represent a small, but important market segment. Such preparations are used for postoperative patients or for individuals with an impaired digestive system. The hydrolysates may be administered as comparatively crude preparations per se (Clegg, 1978 In "Biochemical Aspects of New Protein Food", J, Adler-Nissen, B, O, Eggum, L, Munck & H. S. Olsen eds., p. 109-117, Pergamon, Oxford) or as highly purified mixtures of amino acids for intravenous administration. Enzyme hydrolysates of milk proteins have been applied as dietary preparations.

Enzymatic tenderization of muscle foods, and in particular meat, represents a large market segment, which is presently dominated by plant proteases and certain microbial enzymes. Enzymatic maturation and tenderization of fish muscle is also of considerable importance in many countries. Thus, the presently describe enzymes find use in various uses in food.

Further the enzyme or enzyme compositions of the invention may be useful to make protein hydrolysates from, e.g., vegetable proteins like soy, pea, lupine or rape seed protein, milk like casein, meat proteins, or fish proteins. The enzyme(s) described herein may be used for protein hydrolysates to improve the solubility, consistency or fermentability, to reduce antigenicity, to reduce bitter taste of hydrolysates or for other purposes to make food, feed or medical products. The enzyme(s) described herein may be used alone or together with other peptidases or together with other enzymes like exopeptidases. The use of the enzyme(s) described herein together with exopeptidase rich enzyme preparations will improve the taste of the protein hydrolysates.

Furthermore, the enzyme or enzyme compositions may be used in the processing of fish or meat, e.g. to change texture and/or viscosity.

Leather—

Industrial leather manufacture relies on a series of steps involving cleaning, dehairing and finally tanning and dying of the hides. Enzyme treatment plays an important part in the dehairing step, which is achieved by the application of proteolytic enzymes, the present peptide hydrolases; can provide an effective alternative to the mammalian proteases presently used in leather manufacture, both because of their high proteolytic activity, and their efficiency at low pH.

Wool and Silk—

Proteases described herein find use in the industrial treatment of wool goods to impart desirable properties. In one embodiment, the present invention provides compositions for the treatment of textiles. The composition can be used to treat for example silk or wool (See e.g., RE 216,034; EP 134,267; U.S. Pat. No. 4,533,359; and EP 344,259).

The method of this invention can be applied to treat protein containing fibers, for instance keratin fibers. It is suitable to treat wool, wool fiber or animal hair, such as angora, mohair, cashmere, alpacca, or other commercially useful animal hair product, which may originate from sheep, goat, lama, camel, rabbit etc. Also silk, spidersilk or human hair can be treated with the method of this invention. The fibers may be in the form of fiber, top, yarn or woven or knitted fabric or garments.

Cleaning—

The present invention also relates to cleaning compositions containing the protease(s) of the invention. The cleaning compositions may additionally contain additives which are commonly used in cleaning compositions. These can be selected from, but not limited to, bleaches, surfactants, builders, enzymes and bleach catalysts. It would be readily apparent to one of ordinary skill in the art what additives are suitable for inclusion into the compositions. The list provided herein is by no means exhaustive and should be only taken as examples of suitable additives. It will also be readily apparent to one of ordinary skill in the art to only use those additives which are compatible with the enzymes and other components in the composition, for example, surfactant.

Proteins, particularly those of the invention can be formulated into known powdered and liquid detergents having an acidic pH between 3.5 and 7.0 at levels of about 0.01 to about 5% (preferably 0.1% to 0.5%) by weight. In some embodiments, these detergent cleaning compositions further include other enzymes such as amylases, additional proteases, cellulases, lipases or endoglycosidases, as well as builders and stabilizers. In some embodiments the pH is between 4.0 and 6.5, preferably between 4.0 and 5.6. Although these are referred to as acid proteases due to their pH optimum, depending upon the level of activity required, it may also be possible to use these enzymes at pH 7-9.

The addition of proteins to conventional cleaning compositions does not create any special use limitations. In other words, any temperature and pH suitable for the detergent are also suitable for the present compositions, as long as the pH is within the above range, and the temperature is below the described protein's denaturing temperature. In addition, proteins of the invention find use in cleaning compositions without detergents, again either alone or in combination with builders and stabilizers.

Protein Processing—

Enzymatic hydrolysis of protein raw materials frequently leads to the formation of bitter peptides (Clegg, 1978). The bitter peptides occurring in protein hydrolysates may represent a considerable practical problem, as is the case, e,g, during the ripening of different types of cheese and in the production of dietary protein hydrolysates. The bitterness of hydrolysates is usually due to particular peptides, and especially those which contain a high proportion of hydrophobic amino acids. Bitterness can be effectively reduced by complete or partial hydrolyses of the bitter peptides. Thus, the enzymes described herein find use in debittering of foods. The enzyme or enzyme compositions of the invention may be used for reducing the bitterness of proteins and/or protein hydrolysate for foodstuff.

Also contemplated according to the invention is the production of free amino acids from proteins and/or protein hydrolysates. In the case when the free amino acid is glutamine acid, it enhances the flavor of food products.

Said protein or protein hydrolysate may be of animal or vegetable origin. In an embodiment of the invention the protein to be hydrolyzed is casein or soy protein.

The protein may be use for producing foodstuff such as cheese and foodstuff containing cocoa.

Even though the enzyme(s) described herein and enzyme preparations enriched with an enzyme of the invention may be used especially advantageously in connection with producing proteins or protein hydrolysates without bitter taste, the enzyme(s) described herein can be used for a number of industrial applications, including degradation or modification of protein containing substances, such cell walls. Some proteins, like extensins, are components of plant cell walls. The enzyme(s) described herein will therefore facilitate the degradation or modification of plant cell walls.

The dosage of the enzyme preparation of the invention and other conditions under which the preparation is used may be determined on the basis of methods known in the art.

Protein precipitates may also present a considerable problem in certain products such as e.g, beer, because the precipitate causes the product to be hazy, In beer the haziness arises when soluble proteins precipitate during chill storage of the beer, The problem is of considerable economic importance and, apart from selecting suitable raw materials for the manufacture of beer, the main way of avoiding the problem today is to add proteolytic enzymes to the beer.

Personal Care—

In some embodiments, once the proteases described herein have been synthesized and purified, an effective amount is added to personal care composition(s) that find use in personal care products. Personal care products can be classified/described as cosmetic, over-the-counter ("OTC") compounds that find use in personal care applications (e.g., cosmetics, skin care, oral care, hair care, nail care). In some embodiments, the proteases described herein are added to a personal care composition such as a hair care composition, a skin care composition, a nail care composition, a cosmetic composition, or any combinations thereof. Thus, the enzyme or enzyme preparation may be used, for example, in solutions for cleaning contact lenses, toothpaste, cosmetics and skin care products.

Sweeteners—

Proteases described herein find use in the production of high maltose or high fructose syrups as well as other sweeteners. Raw materials that contain fermentable sugars or constituents which can be converted into sugars are usually starch-containing plant materials including but not limited to tubers, roots, stems, cobs and grains of cereal plants (e.g. corn, wheat, milo, barely, and rye) and sugar-containing raw materials such as sugar beet, sugar cane, fruit materials, and molasses.

Prebiotics—

The enzyme preparation may be useful for production of peptides from proteins, where it is advantageous to use a cloned enzyme essentially free from other proteolytic activities.

By using the enzyme(s) (e.g. purified enzymes) described herein to hydrolyze a suitable protein source, it is possible to produce a crude preparation of free amino acids and peptides which is highly suitable as a substrate for microorganisms that have a specific requirement for amino acids for growth.

This is the case of a considerable number of the microorganisms used in industrial fermentations. The supply of the necessary amino acids often represents an important factor for process economy in such fermentations. The preparation of amino acids produced by applying enzymes is suitable as a substrate both in laboratory and large scale industrial fermentations.

The enzyme(s) described herein may also be used for the in situ generation of functional peptides, prebiotics and the like. The term "prebiotic" refers to a food or feed ingredient that beneficially affects the host by selectively stimulating the growth and/or activity of one or a limited number of bacteria in the digestive track, preferably in the colon.

Fermentation and Bioethanol—

Production of alcohol from the fermentation of starch containing substrates using protease compositions of the invention may include the production of fuel alcohol or portable alcohol. In some embodiments, the enzyme compositions may also be used to facilitate yeast fermentation of barley, malt and other raw materials for the production of e.g. beer.

Amylases are enzymes fundamental to the brewing and baking industries. Amylases are required to break down starch in malting and in certain baking procedures carried out in the absence of added sugars or other carbohydrates. Obtaining adequate activity of these enzymes is problematic especially in the malting industry. A method of adequately increasing the activity of amylases with a physiologically acceptable system, leads to more rapid malting methods and, owing to increased sugar availability, to alcoholic beverages such as beers with reduced carbohydrate content.

In some embodiments, the hydrolysis of starch containing substrates, such as grains (e.g. corn, wheat and sorghum), cobs, and other plant residues will produce alcohol such as ethanol. Methods for alcohol production are described in The Alcohol Textbook, A Reference for the Beverage, Fuel and Industrial Alcohol Industries, $3^{rd}$ Ed., Eds., K. A. Jacques et al., (1999) Nottingham University Press, UK. In some embodiments of the invention, the protease will be used in compositions with glucoamylase and optionally alpha amylases in a combined saccharification and fermentation step, also referred to as simultaneous saccharification and fermentation. Reference is also made to Chapter 2.1, Fermentation Alcohol, S. Lewis in Industrial Enzymology, $2^{nd}$. Ed. Eds., T. Godfrey and S. West, (1996) Stockton Press, NY. Methods for producing ethanol from fermentations using acid fungal proteases in combination with glucoamylases are known. For example, U.S. Pat. No. 5,231,017 discloses a process for producing ethanol using a protease derived from *Aspergillus niger* which includes obtaining a liquefied mash and introducing the protease into the liquefied mash during the saccharification step which may be combined with a fermentation step In some embodiments, the protease composition of the invention will be used to produce alcohol, e.g. ethanol, in a no cook process with granular starch substrates, wherein the process is conducted at a temperature below the gelatinization temperature of the starch in the substrate used to produce the alcohol. While the quantity of the protease used in the starch hydrolysis processes will depend on the enzymatic activity of the protease. In some embodiments, the amount will be in the range of 0.001 to 2.0 ml of a 2% solution of the protease added to 450 g of a slurry adjusted to 20-33% dry solids, wherein the slurry is the liquefied mash during the saccharification and/or in the hydrolyzed starch. Other useful ranges include 0.005 to 1.5 ml and also 0.01 to 1.0 ml.

Seeds or grains treated with proteases provide advantages in the production of malt and beverages produced by a fermentation process.

It is desirable also to use proteases during saccharification so as to hydrolyze the proteins in the flour and thus enrich the wort with soluble nitrogen in anticipation of the subsequent alcoholic fermentation stage. Enhanced activity of amylases in grain increases the speed and efficiency of germination, important in malting, where malt is produced having increased enzymatic activity resulting in enhanced hydrolysis of starch to fermentable carbohydrates, thereby, improving the efficiency of fermentation in the production of alcoholic beverages, for example, beer and scotch whiskey.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); Ci (Curies) mCi (milliCuries); μCi (microCuries); TLC (thin layer chromatography); Ts (tosyl); Bn (benzyl); Ph (phenyl); Ms (mesyl); Et (ethyl), Me (methyl), ds or DS (dry solids content), SAPU (spectrophotometric acid protease unit, wherein in 1 SAPU is the amount of protease enzyme activity that liberates one micromole of tyrosine per minute from a casein substrate under conditions of the assay) and GAU (glucoamylase unit, which is defined as the amount of enzyme that will produce 1 g of reducing sugar calculated as glucose per hour from a soluble starch substrate at pH 4.2 and 60° C.).

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

*Trichoderma reesei* DNA Cloning of a Novel Protease, NSP24

Genomic DNA was extracted from *T. reesei* strain QM6a. PCR primers were designed, based on the putative protease sequence found in contig 1-5500 of the *T. reesei* genome (Joint Genome Institute (JGI) *T. reesei* genome v1.0). The forward primer contained a motif for directional cloning into the pENTR/D vector (Invitrogen).

The sequence of the afp6f primer was CACCATGCAGACCTTTGGAGCT (SEQ ID NO: 11), and the sequence of the afp7r primer was TTATTTCTGAGCCCAGCCCAG (SEQ ID NO: 12). The 1.3 kb PCR product was purified by gel extraction (Gel Purification kit, Qiagen) and cloned into pENTR/D, according to the Invitrogen Gateway system protocol.

Figure 7:
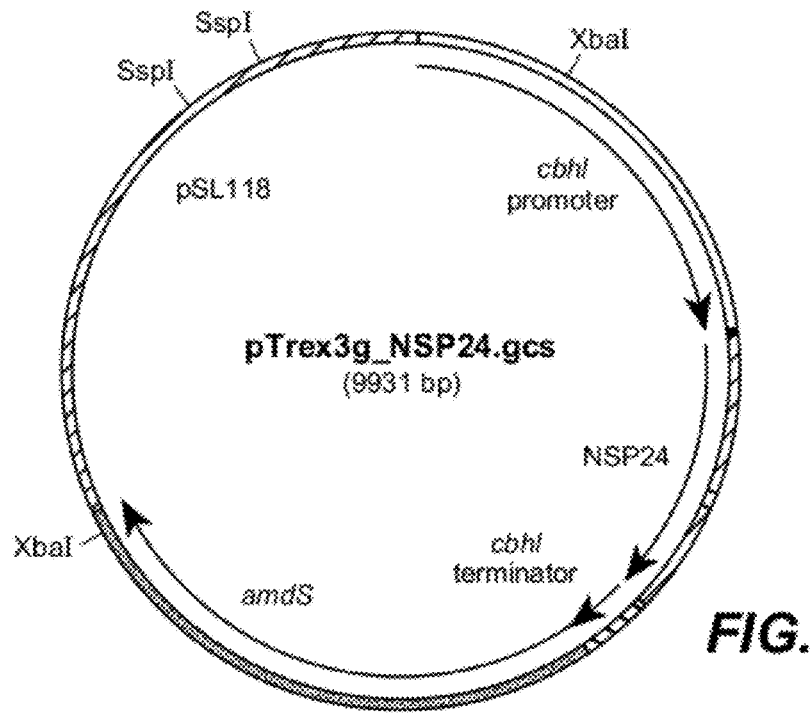
Figure 11:
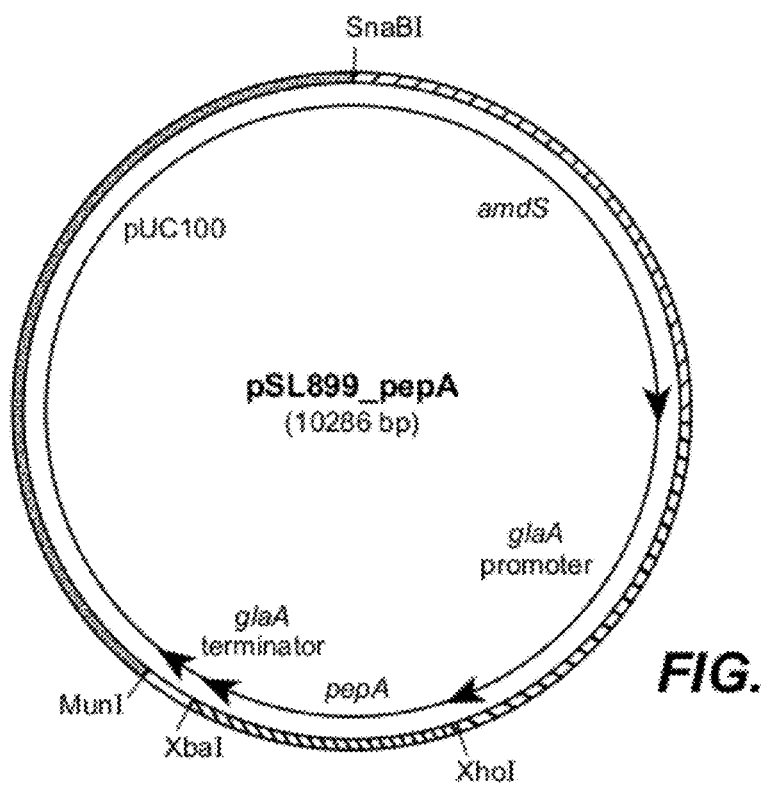

The vector was then transformed into chemically competent Top10 *E. coli* (Invitrogen) with kanamycin selection. Plasmid DNA, from several independent clones, was digested with restriction enzymes to confirm the correct size insert. The protease gene insert was sequenced (Sequetech, Mountain View, Calif.) from several clones. Plasmid DNA from one clone, pENTR/D_55.3, was added to the LR clonase reaction (Invitrogen Gateway system) with pTrex3g/amdS destination vector DNA. The pTrex3g vector is based on the *E. coli* pSL1180 (Pharmacia Inc., NJ), which is a pUC118 phagemid based vector and is described in WO 05/001036. Recombination, in the LR clonase reaction, replaced the CmR and ccdB genes of the destination vector with the *T. reesei* protease from pENTR/D_55.3. This recombination directionally inserted protease between the cbh1 promoter and terminator of the destination vector. Recombination site sequences of 44 and 50 bp remained upstream and downstream, respectively, of the protease gene. An aliquot of the LR clonase reaction was transformed into chemically competent Top10 *E. coli* and grown overnight with carbenicillin selection. Plasmid DNA from several clones was digested with restriction enzymes to confirm the correct insert size. Plasmid DNA from clone, pTrex3g_55.3.1 was digested with XbaI to release the expression cassette including the cbh1 promoter: NSP24 protease:terminator:amdS. This 5.8 kb cassette was purified by agarose gel extraction, using standard techniques, and transformed into a strain of *T. reesei* derived from the publicly available strain QM6a (See, WO 05/001036). Reference is made to FIGS. 5, 6, and 7.

Example 2

*Trichoderma reesei* DNA Cloning of a Novel Protease, NSP25

Genomic DNA was extracted from *T. reesei* strain QM6a. PCR primers were designed, based on the putative protease sequence found in contig 22-263400 of the *T. reesei* genome (JGI *T. reesei* genome v1.0). The forward primer contained a motif for directional cloning into the pENTR/D vector (Invitrogen).

The sequence of the afp8f primer was CACCATGCAGCCCTCATTTGGCAG (SEQ ID NO: 13), and the sequence of the afp9r primer was CTATTTCTTCTGCGCCCAGCCAAC (SEQ ID NO: 14). The 1.2 kb PCR product was purified by gel extraction (Gel Purification kit, Qiagen) and cloned into pENTR/D, according to the Invitrogen Gateway system protocol. The vector was then transformed into chemically competent Top10 *E. coli* (Invitrogen) with kanamycin selection. Plasmid DNA, from several independent clones, was digested with restriction enzymes to confirm the correct size insert. The protease gene insert was sequenced (Sequetech, Mountain View, Calif.) from several clones. Plasmid DNA from one clone, pENTR/D_22.2, was added to the LR clonase reaction (Invitrogen Gateway system) with pTrex3g/amdS destination vector DNA. Recombination, in the LR clonase reaction, replaced the CmR and ccdB genes of the destination vector with the *T. reesei* protease from pENTR/D_22.2. This recombination directionally inserted protease between the cbh1 promoter and terminator of the destination vector. Recombination site sequences of 44 and 50 bp remained upstream and downstream, respectively, of the protease gene.

An aliquot of the LR clonase reaction was transformed into chemically competent Top10 E. coli and grown overnight with carbenicillin selection. Plasmid DNA from several clones was digested with restriction enzymes to confirm the correct insert size. Plasmid DNA from clone, pTrex3g_22.2#1 was digested with XbaI (and EcoRI to digest the bacterial backbone into small fragments, which migrated away from the cassette during electrophoresis) to release the expression cassette including the cbhI promoter:NSP25 protease:terminator:amdS. This 5.7 kb cassette was purified by agarose gel extraction, using standard techniques, and transformed into a strain of T. reesei derived from the publicly available strain QM6a. The plasmid used for transformation was essentially the same as the plasmid illustrated in FIG. 7 except, the NSP24 insert was replaced with the NSP25 sequence.

Example 3

Trichoderma PEG Fungal Transformation

A 2 cm$^2$ agar plug from a plate of sporulated mycelia was inoculated into 50 ml of YEG broth in a 250 ml, 4-baffled shake flask and incubated at 37° C. for 16-20 hours at 200 rpm. The mycelia were recovered by transferring liquid volume into 50 ml conical tubes and spun at 2500 rpm for 10 minutes. The supernatant was aspirated off. The mycelial pellet was transferred into a 250 ml, 0.22 μm CA Corning filter bottle containing 40 ml of filter-sterilized β-D-glucanase (InterSpex Products, Inc.) solution and incubated at 30° C., 200 rpm for 2 hours. The mycelia were harvested through sterile Miracloth (CalBiochem, LaJolla, Calif.) into a 50 ml conical centrifuge tube, centrifuged at 2000 rpm for 5 minutes, aspirated. The pellet was washed once with 50 ml of 1.2M sorbitol, centrifuged again, aspirated, and washed with 25 ml of sorbitol/CaCl$_2$. The protoplasts were counted using a hemocytometer, centrifuged, aspirated, and resuspended in a volume of sorbitol/CaCl$_2$ sufficient to generate a protoplast concentration of $1.25 \times 10^8$/ml. Aliquots of 200 μl were used per transformation reaction. 20 μg of DNA (≧1 μg/ul) was placed into 15 ml conical tubes and the tubes were placed on ice. 200 μl of the protoplasts were added. 50 μl PEG mix was added and mixed gently and incubated on ice for 20 minutes. 2 ml of PEG mix was added to the tubes and incubated at room temperature for 5 minutes. 4 ml sorbitol/CaCl$_2$ (for a total of 6.25 ml) was added to the tubes. This transformation mixture was divided into 3 aliquots of ~2 ml per each overlay. The 2 ml was added to a tube of melted acetamide sorbitol top agar and the overlay mixture was poured onto acetamide sorbitol plates for selection of transformants able to grow with acetamide as the sole nitrogen source. Plates were incubated at 28-30° C. until colonies appeared. Transformants were purified by repeat passage of single colonies on acetamide media (acetamide sorbitol recipe without the sorbitol).

Materials—
    40 ml β-D-glucanase Solution: 600 mg β-D-glucanase; 400 mg MgSO$_4$.7H$_2$0 and 40 ml 1.2 M sorbitol.
    200 ml PEG Mix: 50 g PEG 4000 (BDH Laboratory Supplies Poole, England) and 1.47 g CaCl$_2$2H$_2$O made up in Milli Q water
    Sorbitol/CaCl$_2$: 1.2M Sorbitol and 50 mM CaCl$_2$
    For amdS selection, Acetamide Sorbitol plates and overlays were used. For spore purification, the same plates were used, but without sorbitol.
Acetamide Sorbitol Agar (Plates and Top Agar)
    Acetamide (Aldrich 99% sublimed)—0.6 g/L; CsCl—1.68 g/L; Glucose—20 g/L; KH$_2$PO$_4$—20 g/L; MgSO$_4$*7H$_2$O—0.6 g/L; CaCl$_2$*2H$_2$O—0.6 g/L; 1000× salts (see below)—1 ml. pH adjusted to 5.5 and volume brought to 300 ml. Filter sterilized with 0.22 micron filter and warmed to 55° C. in an oven.
    To 700 ml water Noble Agar (low-melt for top agar) 20 g and Sorbitol 218 g was added and then autoclaved. This mixture was cooled to 55° C., and filter sterilized acetamide mix was added. Plates or tubes were poured.
    1000× Salts—FeSO$_4$.7H$_2$O (0.5 g/100 ml); MnSO$_4$.H$_2$O (0.16 g/100 ml); ZnSO$_4$.7H$_2$O (0.14 g/100 ml); CoCl$_2$.6H$_2$O (0.1 g/100 ml) and filter sterilize with 0.22 micron filter.
    Potato Dextrose Agar (PDA, Difco Dehydrated Culture Media)—Potatoes, infusion from 200 g/L; Dextrose, 20 g/L and Agar, 15 g/L were mixed well in 50-80% final volume of dH2O, and then brought to 100% final volume. This mixture is autoclaved, cooled to 55° C. and pour.
    To make up 1% skim milk agar for a pH 3.5 media PDA was prepared as above and to 100 ml molten PDA, 1.8 ml 10% tartaric acid and 12.5 ml sterilized 8% skim milk was added and plates were poured. To pre-sterilize skim milk, 8% skim milk (Difco) was autoclaved for 10 minutes, 122-123° C., and chamber pressure during exposure of 32-35 psi. The mixture was removed, cooled and stored at room temperature.
    Protease Expression was evaluated in transformants after 3 days growth in shake flasks. T. reesei culture media (Davis, et al., (1970) Methods Enzymol. 17:79-143) was inoculated with an agar plug. Cultures were incubated for 3 days at 30° C., with shaking. Culture broth was passed through a 0.22 micron filter, and the filtrate spotted onto 1% Skim milk agar. Clearing zones were observed following overnight incubation at room temperature.

Example 4

PH Activity Profiles of NSP24, NSP25 and L388M PepA

The pH-activity profiles of PepA (Wild type and L388M), NSP24 and NSP25 all of which were overexpressed in a strain of Trichoderma reesei were determined using a fluorescently labeled casein assay obtained from Molecular Probes (EnzChek Portease Kit—Green fluorescence). The PepA (wild-type and L388M) and NSP were whole fermentation samples and NSP24 was a purified protein stabilized in 50% glycerol. The enzymes were diluted to 1.0 mg/ml, 0.5 mg/ml and 0.25 mg/ml. Fluorescently labeled substrate was diluted to 0.1 mg/ml in DI H$_2$O. 10 ml of substrate was added to 50 ml of buffer of various pH and 30 ul DI H$_2$O. reactions were initiated by the addition of 10 ml of enzyme and allowed to continue for various time periods before being quenched by the addition of 100 ul 1.0M phosphate at pH 10. the fluorescence of the sample was measured at 538 nm emission with excitation at 485 and an emission cut off filter at 530 nm in a SpectraMAX EM fluorescence plate reader. NSP24 has optimal activity at pH 3.7, wild-type PepA has optimal activity at pH 3.4 and L388M pepA has optimal pH at 3.5. NSP25 has optimal activity at pH 4.6.

Example 5

Comparison of Trichoderma reesei NSP24 Protease to GC 106 in Laboratory Fermentations A standard protease used in the ethanol industry today is the protease GC106 sold commercially by Genencor International, Inc. The functionality of NSP24 to GC 106 was compared with respect to sugar degradation, glucose formation, and ethanol production.
Materials
Distillase L-400 (Lot#107-04057-901, 372 GAU/g)
GC 106 (Lot#A01-01300-001, 1010 SAPU/g)
NSP 24 (Lot#20040423, 1165 SAPU/g)
Red Star Red Yeast
Mash and Thin Stillage (Corn) from an ethanol producer
Method Mash and thin stillage (also referred to as backset, prior to fermentation) from an ethanol producer was obtained and mixed to 26.5 brix. The pH was adjusted to pH 4.3 using 1N HCL. Samples were then divided into 3-300 gram aliquots and placed into a 32° C. water bath. After equilibration, the following enzyme combinations were added:

TABLE 2

| Enzyme | Level | Enzyme | Level |
|---|---|---|---|
| — | — | Distillase L-400 | 0.4 GAU/g |
| GC106 | 70 ul of 1:10 dil | Distillase L-400 | 0.4 GAU/g |
| NSP24 | 60 ul of 1:10 dil | Distillase L-400 | 0.4 GAU/g |

DISTILLASE L-400 is a liquid glucoamylase derived from *Aspergillus niger* which can be obtained from Genencor International Inc. After enzyme addition, 1.00 gram/flask of Red Star Red yeast was added. Samples were taken at 16, 24, 40, and 48 hours and centrifuged. 500 ul of each sample was placed into a test tube with 50 ul of a 1.1 $NH_2SO_4$ to stop the reaction. After 2 minutes, the samples were diluted with 4.5 ml of DI $H_2O$ and mixed. After mixing, the samples were run through a 0.45-micron filter and placed into HPLC vials for analysis. The samples were analyzed by HPLC (Phenomenex Rezex 8u). Results are illustrated in FIGS. 1-4. NSP24 performed similarly to GC 106.

Example 6

Effect of NSP24 on Ethanol Yield from Ground Corn in a Non-Cook Process

A 30% DS slurry of ground corn was made up with DI $H_2O$. The ground corn was a typical sample of #2 Yellow dent corn used in the ethanol industry, which was ground so that greater than 70% would pass thru a 30 mesh screen. The moisture content of the grain was measured using an OHAUS, MB 35 Halogen moisture balance (NJ). The pH was adjusted to 4.2 using 6N $H_2SO_4$. Fermentations were conducted in 125 ml flasks containing 100 g mash with STARGEN 001 dosed at 1.0 GAU/g and with or without NSP24 dosed at 0.5 kg/MT.

5 g Red Star Ethanol Red dry yeast (Lesaffre yeast Corporation, Milwaukee, Wis.) in 45 mls of water was prepared and mixed in a 32° C. water bath one hour prior to inoculating the fermenters. 0.5 ml of the yeast slurry was added to each 125 ml flask. The flasks were placed in a 32° C. water bath and the mash mixed gently. During the fermentations, samples were removed for HPLC analysis (HPLC Column: Phenomenex Rezex Organic Acid Column (RHM-Monosaccharide) #00H 0132-KO; Column Temperature: 60 C; Mobile Phase: 0.01N H2SO4; Flow Rate: 0.6 mL/min; Detector: RI; and Injection Volume: 20 uL. The fermentations were terminated after 72 hours. Production of compounds including sugars, lactic acid, glycerol and ethanol at different sampling interval is shown below in Table 3, wherein + indicated that NSP 24 was added to the flasks and -- indicates that NSP24 was not added to the flasks. Lactic acid for all samples was measured at between about 0.01 and 0.02% w/v and DP-2 was determined to be 0.0. At 24 hours, acetic acid was determine to be approximately 0, and at 71 hours between 0.03 and 0.04 for all samples.

TABLE 3

| NSP24 | Hours | % w/v DP > 4 | % w/v DP-2 | % w/v DP-1 | % w/v glycerol | % v/v Ethanol |
|---|---|---|---|---|---|---|
| + | 24 | 0.44 | 0.04 | 0.96 | 0.73 | 11.23 |
| + | 48 | 0.52 | 0.11 | 1.66 | 0.86 | 15.47 |
| + | 71 | 0.54 | 0.14 | 2.27 | 0.90 | 16.82 |
| -- | 24 | 0.62 | 0.04 | 0.32 | 0.69 | 14.24 |
| -- | 48 | 0.59 | 0.13 | 0.95 | 0.80 | 17.81 |
| -- | 71 | 0.58 | 0.16 | 1.64 | 0.82 | 18.03 |

Example 7

Comparison of Different Proteases on Ethanol Production Using Corn Endosperm

A 29.5% DS mash using endosperm (degermed corn, 75.8% starch, particle size of 99.5%<30 mesh) as a granular starch substrate was prepared. One hundred grams of each mash was transferred to a 125 ml flask, and the pH of the medium was adjusted to pH 4.5. Proteases, (NSP24; neutral Proteases (MULTIFECT NEUTRAL, PROTEINASE-T) and alkaline proteases (SPEZYME FAN, PROTEX 6L MULTIFECT P-3000 and PROTEASE 899 (Genencor International)), were added at 0.5 kg/MT followed by the addition of STARGEN 001 (Genencor International) at 2.5 Kgs/MT of starch). The flasks were then inoculated with 0.5 ml of 20% yeast (Red Star Ethanol Red) and placed in a water bath maintained at 32° C. The contents of the flask were continuously stirred for uniform mixing during incubation. Samples were taken at different intervals of time for HPLC analysis. The residual starch and protein content of the DDGS from 72 hours fermentor broth were determined. The results for ethanol production are shown below in Table 4.

TABLE 4

| Protease | % alcohol, v/v 20 hr | % alcohol, v/v 27 hr | % alcohol, v/v 43 hr | % alcohol, v/v 51 hr | % alcohol, v/v 75 hr |
|---|---|---|---|---|---|
| NSP24 | 11.50 | 14.42 | 17.39 | 17.97 | 18.61 |
| MULTIFECT P3000 | 9.58 | 12.12 | 15.04 | 15.75 | 16.96 |
| PROTEX 6L | 9.94 | 12.54 | 15.46 | 15.95 | 17.29 |
| SPEZYME FAN | 9.78 | 12.27 | 15.03 | 15.88 | 17.19 |
| PROTEINASE T | 9.29 | 11.73 | 15.01 | 15.87 | 17.28 |
| PROTEASE 899 | 9.62 | 11.90 | 14.66 | 15.37 | 17.95 |
| MULTIFECT NEUTRAL | 9.63 | 11.91 | 14.73 | 15.31 | 16.85 |

We claim:

1. An isolated polynucleotide encoding an NSP25 family protease having at least 97% sequence identity to the polypeptide sequence of SEQ ID NO:9.

2. The isolated polynucleotide of claim 1 having the nucleotide sequence of SEQ ID NO:4.

3. A vector comprising the polynucleotide of claim 1.

4. An isolated host cell transformed with the polynucleotide of claim 1.

5. The host cell of claim 4, wherein the host cell is a filamentous fungal cell.

6. The host cell of claim 5, wherein the filamentous fungal cell is an *Aspergillus* spp., a *Fusarium* spp., or a *Trichoderma* spp.

7. The host cell of claim 6, wherein the *Aspergillus* is *A. niger, A. oryzae, A. nidulans,* or *A. awamori.*

8. The host cell of claim 6, wherein the *Trichoderma* is *T. reesei.*

9. The host cell of claim 6, wherein the *Trichoderma* host cell comprises deletions of at least two endoducanase-encoding genes and at least two cellobiohydrolase-encoding genes.

10. A method for producing a protease comprising
   a) introducing into an isolated host cell a polynucleotide comprising a promoter operably linked to a nucleic acid encoding a NSP25 family protease having at least 97% sequence identity to the polypeptide sequence of SEQ ID NO:9,
   b) culturing the host cell under suitable culture conditions for the expression and production of the NSP25 family protease, and
   c) producing said NSP25 family protease.

* * * * *

SEQUENCE LISTING

<160> NUMBER OF SEQ ID NOS: 14

<210> SEQ ID NO 1
<211> LENGTH: 9931
<212> TYPE: DNA
<213> ORGANISM: Artificial Sequence
<220> FEATURE:
<223> OTHER INFORMATION: synthetic pTrex3g_NSP24 plasmid

<400> SEQUENCE: 1

```
ctgcagccac ttgcagtccc gtggaattct cacggtgaat gtaggccttt tgtagggtag      60
gaattgtcac tcaagcaccc ccaacctcca ttacgcctcc cccatagagt tcccaatcag     120
tgagtcatgg cactgttctc aaatagattg gggagaagtt gacttccgcc cagagctgaa     180
ggtcgcacaa ccgcatgata tagggtcggc aacggcaaaa aagcacgtgg ctcaccgaaa     240
agcaagatgt ttgcgatcta acatccagga acctggatac atccatcatc acgcacgacc     300
actttgatct gctggtaaac tcgtattcgc cctaaaccga agtgcgtggt aaatctacac     360
gtgggcccct ttcggtatac tgcgtgtgtc ttctctaggt gccattcttt tcccttcctc     420
tagtgttgaa ttgtttgtgt tggagtccga gctgtaacta cctctgaatc tctggagaat     480
ggtggactaa cgactaccgt gcacctgcat catgtatata atagtgatcc tgagaagggg     540
ggtttggagc aatgtgggac tttgatggtc atcaaacaaa gaacgaagac gcctcttttg     600
caaagttttg tttcggctac ggtgaagaac tggatacttg ttgtgtcttc tgtgtatttt     660
tgtggcaaca agaggccaga gacaatctat tcaaacacca gcttgctct tttgagctac      720
aagaacctgt ggggtatata tctagagttg tgaagtcggt aatcccgctg tatagtaata     780
cgagtcgcat ctaaatactc cgaagctgct gcgaacccgg agaatcgaga tgtgctggaa     840
agcttctagc gagcggctaa attagcatga aaggctatga gaaattctgg agacggcttg     900
ttgaatcatg gcgttccatt cttcgacaag caaagcgttc cgtcgcagta gcaggcactc     960
attcccgaaa aaactcggag attcctaagt agcgatggaa ccggaataat ataataggca    1020
atacattgag ttgcctcgac ggttgcatg cagggggtact gagcttggac ataactgttc    1080
cgtaccccac ctcttctcaa cctttggcgt ttccctgatt cagcgtaccc gtacaagtcg    1140
taatcactat taacccagac tgaccggacg tgttttgccc ttcatttgga gaataatgt     1200
cattgcgatg tgtaatttgc ctgcttgacc gactggggct gttcgaagcc gaatgtagg     1260
attgttatcc gaactctgct cgtagaggca tgttgtgaat ctgtgtcggg caggacacgc    1320
ctcgaaggtt cacggcaagg gaaaccaccg atagcagtgt ctagtagcaa cctgtaaagc    1380
cgcaatgcag catcactgga aaatacaaac caatggctaa aagtacataa gttaatgcct    1440
aaagaagtca tataccagcg gctaataatt gtacaatcaa gtggctaaac gtaccgtaat    1500
ttgccaacgg cttgtggggt tgcagaagca acggcaaagc cccacttccc cacgtttgtt    1560
tcttcactca gtccaatctc agctggtgat ccccaattg ggtcgcttgt tgttccggt      1620
gaagtgaaag aagacagagg taagaatgtc tgactcggag cgttttgcat acaaccaagg    1680
gcagtgatgg aagacagtga atgttgaca ttcaaggagt atttagccag ggatgcttga     1740
gtgtatcgtg taaggaggtt tgtctgccga tacgacgaat actgtatagt cacttctgat    1800
gaagtggtcc atattgaaat gtaagtcggc actgaacagg caaagattg agttgaaact     1860
gcctaagatc tcgggccctc gggcttcgg cctttgggtg tacatgtttg tgctccgggc     1920
aaatgcaaag tgtggtagga tcgaacacac tgctgccttt accaagcagc tgagggtatg    1980
```

```
tgataggcaa atgttcaggg gccactgcat ggtttcgaat agaaagagaa gcttagccaa    2040
gaacaatagc cgataaagat agcctcatta acggaatga gctagtaggc aaagtcagcg     2100
aatgtgtata tataaaggtt cgaggtccgt gcctccctca tgctctcccc atctactcat    2160
caactcagat cctccaggag acttgtacac catcttttga ggcacagaaa cccaatagtc    2220
aaccatcaca gtttgtaca aaaaagcagg ctccgcggcc gcccccttca ccatgcagac     2280 cttttggagct tttctcgttt ccttcctcgc cgccagcggc ctggccgcgg ccctccccac   2340
cgagggtcag aagacggctt ccgtcgaggt ccagtacaac aagaactacg tcccccacgg    2400
ccctactgct ctcttcaagg ccaagagaaa gtatggcgct cccatcagcg acaacctgaa    2460
gtctctcgtg gctgccaggc aggccaagca ggctctcgcc aagcgccaga ccggctcggc    2520
gcccaaccac cccagtgaca cgcgccgattc ggagtacatc acctccgtct ccatcggcac   2580
tccggctcag gtcctccccc tggactttga caccggctcc tccgacctgt gggtctttag    2640
ctccgagacg cccaagtctt cggccaccgg ccacgccatc tacacgccct ccaagtcgtc    2700
cacctccaag aaggtgtctg cgccagctg gtccatcagc tacggcgacg gcagcagctc    2760
cagcggcgat gtctacaccg acaaggtcac catcggaggc ttcagcgtca cacccaggg    2820 cgtcgagtct gccacccgcg tgtccaccga gttcgtccag gacacggtca tctctggcct    2880
cgtcggcctt gcctttgaca gcggcaacca ggtcaggccg cacccgcaga gacgtggtt    2940 ctccaacgcc gccagcagcc tggctgagcc ccttttcact gccgacctga ggcacggaca    3000
gagtaagtag acactcactg gaattcgttc cttccccgat catcatgaaa gcaagtagac    3060
tgactgaacc aaacaactag acggcagcta caactttggc tacatcgaca ccagcgtcgc    3120
caagggcccc gttgcctaca cccccgttga caacagccag ggcttctggg agttcactgc    3180
ctcgggctac tctgtcggcg gcggcaagct caaccgcaac tccatcgacg gcattgccga    3240
caccggcacc accctgctcc tcctcgacga caacgtcgtc gatgcctact acgccaacgt    3300
ccagtcggcc cagtacgaca accagcagga gggtgtcgtc ttcgactgcg acgaggacct    3360
cccttcgttc agcttcggtg ttggaagctc caccatcacc atccctggcg atctgctgaa    3420
cctgactccc ctcgaggagg gcagctccac ctgcttcggt ggcctccaga gcagctccgg    3480
cattggcatc aacatctttg tgacgttgc cctcaaggct gccctggttg tctttgacct    3540
cggcaacgag cgcctgggct gggctcagaa ataaaagggt gggcgcgccg acccagcttt    3600
cttgtacaaa gtggtgatcg cgccagctcc gtgcgaaagc ctgacgcacc ggtagattct    3660
tggtgagccc gtatcatgac ggcggcggga gctacatggc cccgggtgat ttatttttt    3720 tgtatctact tctgacccctt ttcaaatata cggtcaactc atctttcact ggagatgcgg    3780
cctgcttggt attgcgatgt tgtcagcttg gcaaattgtg gctttcgaaa acacaaaacg    3840
attccttagt agccatgcat tttaagataa cggaatagaa gaaagaggaa attaaaaaaa    3900
aaaaaaaaac aaacatcccg ttcataaccc gtagaatcgc cgctcttcgt gtatcccagt    3960
accagtttat tttgaatagc tcgcccgctg gagagcatcc tgaatgcaag taacaaccgt    4020
agaggctgac acggcaggtg ttgctaggga gcgtcgtgtt ctacaaggcc agacgtcttc    4080
gcggttgata tatgtatg tttgactgca ggctgctcag cgacgacagt caagttcgcc     4140
ctcgctgctt gtgcaataat cgcagtgggg aagccacacc gtgactccca tctttcagta    4200
aagctctgtt ggtgtttatc agcaatacac gtaatttaaa ctcgttagca tggggctgat    4260
agcttaatta ccgttaccca gtgccatggt tctgcagctt ccttggccc gtaaaattcg     4320 gcgaagccag ccaatcacca gctaggcacc agctaaaccc tataattagt ctcttatcaa    4380
```

```
caccatccgc tcccccggga tcaatgagga gaatgagggg gatgcggggc taaagaagcc    4440
tacataaccc tcatgccaac tcccagttta cactcgtcga gccaacatcc tgactataag    4500
ctaacacaga atgcctcaat cctgggaaga actggccgct gataagcgcg cccgcctcgc    4560
aaaaaccatc cctgatgaat ggaaagtcca gacgctgcct gcggaagaca gcgttattga    4620
tttcccaaag aaatcgggga tcctttcaga ggccgaactg aagatcacag aggcctccgc    4680
tgcagatctt gtgtccaagc tggcggccgg agagttgacc tcggtggaag ttacgctagc    4740
attctgtaaa cgggcagcaa tcgcccagca gttagtaggg tcccctctac ctctcaggga    4800
gatgtaacaa cgccacctta tgggactatc aagctgacgc tggcttctgt gcagacaaac    4860
tgcgcccacg agttcttccc tgacgccgct ctcgcgcagg caagggaact cgatgaatac    4920
tacgcaaagc acaagagacc cgttggtcca ctccatggcc tccccatctc tctcaaagac    4980
cagcttcgag tcaaggtaca ccgttgcccc taagtcgtta gatgtccctt tttgtcagct    5040
aacatatgcc accagggcta cgaaacatca atgggctaca tctcatggct aaacaagtac    5100
gacgaagggg actcggttct gacaaccatg ctccgcaaag ccggtgccgt cttctacgtc    5160
aagacctctg tcccgcagac cctgatggtc tgcgagacag tcaacaacat catcgggcgc    5220
accgtcaacc cacgcaacaa gaactggtcg tgcggcggca gttctggtgg tgagggtgcg    5280
atcgttggga ttcgtggtgg cgtcatcggt gtaggaacgg atatcggtgg ctcgattcga    5340
gtgccggccg cgttcaactt cctgtacggt ctaaggccga gtcatgggcg gctgccgtat    5400
gcaaagatgg cgaacagcat ggagggtcag gagacggtgc acagcgttgt cgggccgatt    5460
acgcactctg ttgagggtga gtccttcgcc tcttccttct tttcctgctc tataccaggc    5520
ctccactgtc ctcctttctt gctttttata ctatatacga gaccggcagt cactgatgaa    5580
gtatgttaga cctccgcctc ttcaccaaat ccgtcctcgg tcaggagcca tggaaatacg    5640
actccaaggt catccccatg ccctggcgca gtccgagtc ggacattatt gcctccaaga    5700
tcaagaacgg cgggctcaat atcggctact acaacttcga cggcaatgtc cttccacacc    5760
ctcctatcct gcgcggcgtg gaaaccaccg tcgccgcact cgccaaagcc ggtcacaccg    5820
tgaccccgtg gacgccatac aagcacgatt tcggccacga tctcatctcc catatctacg    5880
cggctgacgg cagcgccgac gtaatgcgcg atatcagtgc atccggcgag ccggcgattc    5940
caaatatcaa agacctactg aacccgaaca tcaaagctgt taacatgaac gagctctggg    6000
acacgcatct ccagaagtgg aattaccaga tggagtacct tgagaaatgg cgggaggctg    6060
aagaaaaggc cgggaaggaa ctggacgcca tcatcgcgcc gattacgcct accgctgcgg    6120
tacggcatga ccagttccgg tactatgggt atgcctctgt gatcaacctg ctggatttca    6180
cgagcgtggt tgttccggtt acctttgcgg ataagaacat cgataagaag aatgagagtt    6240
tcaaggcggt tagtgagctt gatgccctcg tgcaggaaga gtatgatccg gaggcgtacc    6300
atggggcacc ggttgcagtg caggttatcg gacggagact cagtgaagag aggacgttgg    6360
cgattgcaga ggaagtgggg aagttgctgg gaaatgtggt gactccatag ctaataagtg    6420
tcagatagca atttgcacaa gaaatcaata ccagcaactg taaataagcg ctgaagtgac    6480
catgccatgc tacgaaagag cagaaaaaaa cctgccgtag aaccgaagag atatgacacg    6540
cttccatctc tcaaaggaag aatcccttca ggtttgcgtt tccagtctag acacgtataa    6600
cggcacaagt gtctctcacc aaatgggtta tatctcaaat gtgatctaag gatggaaagc    6660
ccagaatatc gatcgcgcgc agatccatat atagggcccg ggttataatt acctcaggtc    6720
gacgtcccat ggccattcga attcgtaatc atggtcatag ctgtttcctg tgtgaaattg    6780
```

```
ttatccgctc acaattccac acaacatacg agccggaagc ataaagtgta aagcctgggg    6840
tgcctaatga gtgagctaac tcacattaat tgcgttgcgc tcactgcccg ctttccagtc    6900
gggaaacctg tcgtgccagc tgcattaatg aatcggccaa cgcgcgggga gaggcggttt    6960
gcgtattggg cgctcttccg cttcctcgct cactgactcg ctgcgctcgg tcgttcggct    7020
gcggcgagcg gtatcagctc actcaaaggc ggtaatacgg ttatccacag aatcagggga    7080
taacgcagga aagaacatgt gagcaaaagg ccagcaaaag gccaggaacc gtaaaaaggc    7140
cgcgttgctg gcgttttttcc ataggctccg ccccccctgac gagcatcaca aaaatcgacg    7200
ctcaagtcag aggtggcgaa acccgacagg actataaaga taccaggcgt ttccccctgg    7260
aagctccctc gtgcgctctc ctgttccgac cctgccgctt accggatacc tgtccgcctt    7320
tctcccttcg ggaagcgtgg cgctttctca tagctcacgc tgtaggtatc tcagttcggt    7380
gtaggtcgtt cgctccaagc tgggctgtgt gcacgaaccc cccgttcagc ccgaccgctg    7440
cgccttatcc ggtaactatc gtcttgagtc caacccggta agacacgact tatcgccact    7500
ggcagcagcc actggtaaca ggattagcag agcgaggtat gtaggcggtg ctacagagtt    7560
cttgaagtgg tggcctaact acggctacac tagaagaaca gtatttggta tctgcgctct    7620
gctgaagcca gttaccttcg gaaaaagagt tggtagctct tgatccggca aacaaaccac    7680
cgctggtagc ggtggttttt ttgtttgcaa gcagcagatt acgcgcagaa aaaaggatc    7740
tcaagaagat cctttgatct tttctacggg gtctgacgct cagtggaacg aaaactcacg    7800
ttaagggatt ttggtcatga gattatcaaa aaggatcttc acctagatcc ttttaaatta    7860
aaaatgaagt tttaaatcaa tctaaagtat atatgagtaa acttggtctg acagttacca    7920
atgcttaatc agtgaggcac ctatctcagc gatctgtcta tttcgttcat ccatagttgc    7980
ctgactcccc gtcgtgtaga taactacgat acgggagggc ttaccatctg gccccagtgc    8040
tgcaatgata ccgcgagacc cacgctcacc ggctccagat ttatcagcaa taaaccagcc    8100
agccggaagg gccgagcgca gaagtggtcc tgcaacttta tccgcctcca tccagtctat    8160
taattgttgc cgggaagcta gagtaagtag ttcgccagtt aatagtttgc gcaacgttgt    8220
tgccattgct acaggcatcg tggtgtcacg ctcgtcgttt ggtatggctt cattcagctc    8280
cggttcccaa cgatcaaggc gagttacatg atcccccatg ttgtgcaaaa aagcggttag    8340
ctccttcggt cctccgatcg ttgtcagaag taagttggcc gcagtgttat cactcatggt    8400
tatggcagca ctgcataatt ctcttactgt catgccatcc gtaagatgct tttctgtgac    8460
tggtgagtac tcaaccaagt cattctgaga atagtgtatg cggcgaccga gttgctcttg    8520
cccggcgtca atacgggata ataccgcgcc acatagcaga actttaaaag tgctcatcat    8580
tggaaaacgt tcttcgggc gaaaactctc aaggatctta ccgctgttga tccagttc    8640
gatgtaaccc actcgtgcac ccaactgatc ttcagcatct tttactttca ccagcgtttc    8700
tgggtgagca aaaacaggaa ggcaaaatgc cgcaaaaaag gaataagggc gacacggaa    8760
atgttgaata ctcatactct ccttttttca atattattga agcatttatc agggttattg    8820
tctcatgagc ggatacatat ttgaatgtat ttagaaaaat aaacaaatag gggttccgcg    8880
cacatttccc cgaaaagtgc cacctgacgt ctaagaaacc attattatca tgacattaac    8940
ctataaaaat aggcgtatca cgaggccctt tcgtctcgcg cgtttcggtg atgacggtga    9000
aaacctctga cacatgcagc tcccggagac ggtcacagct tgtctgtaag cggatgccgg    9060
gagcagacaa gcccgtcagg gcgcgtcagc gggtgttggc gggtgtcggg gctggcttaa    9120
ctatgcggca tcagagcaga ttgtactgag agtgcaccat aaaattgtaa acgttaatat    9180
```

-continued

```
tttgttaaaa ttcgcgttaa attttttgtta aatcagctca tttttttaacc aataggccga    9240
aatcggcaaa atcccttata aatcaaaaga atagcccgag atagggttga gtgttgttcc    9300
agtttggaac aagagtccac tattaaagaa cgtggactcc aacgtcaaag ggcgaaaaac    9360
cgtctatcag ggcgatggcc cactacgtga accatcaccc aaatcaagtt ttttggggtc    9420
gaggtgccgt aaagcactaa atcggaaccc taaagggagc ccccgattta gagcttgacg    9480
gggaaagccg cgaacgtgg cgagaaagga agggaagaaa gcgaaggag cgggcgctag      9540
ggcgctggca agtgtagcgg tcacgctgcg cgtaaccacc acaccccgccg cgcttaatgc    9600
gccgctacag ggcgcgtact atggttgctt tgacgtatgc ggtgtgaaat accgcacaga    9660
tgcgtaagga gaaaataccg catcaggcgc cattcgccat tcaggctgcg caactgttgg    9720
gaagggcgat cggtgcgggc ctcttcgcta ttacgccagc tggcgaaagg gggatgtgct    9780
gcaaggcgat taagttgggt aacgccaggg ttttcccagt cacgacgttg taaaacgacg    9840
gccagtgccc aagcttacta gtacttctcg agctctgtac atgtccggtc gcgacgtacg    9900
cgtatcgatg gcgccagctg caggcggccg c                                    9931
```

<210> SEQ ID NO 2
<211> LENGTH: 407
<212> TYPE: PRT
<213> ORGANISM: Trichoderma reesei

<400> SEQUENCE: 2

```
Met Gln Thr Phe Gly Ala Phe Leu Val Ser Phe Leu Ala Ala Ser Gly
1               5                   10                  15

Leu Ala Ala Ala Leu Pro Thr Glu Gly Gln Lys Thr Ala Ser Val Glu
                20                  25                  30

Val Gln Tyr Asn Lys Asn Tyr Val Pro His Gly Pro Thr Ala Leu Phe
            35                  40                  45

Lys Ala Lys Arg Lys Tyr Gly Ala Pro Ile Ser Asp Asn Leu Lys Ser
        50                  55                  60

Leu Val Ala Ala Arg Gln Ala Lys Gln Ala Leu Ala Lys Arg Gln Thr
65                  70                  75                  80

Gly Ser Ala Pro Asn His Pro Ser Asp Ser Ala Asp Ser Glu Tyr Ile
                85                  90                  95

Thr Ser Val Ser Ile Gly Thr Pro Ala Gln Val Leu Pro Leu Asp Phe
            100                 105                 110

Asp Thr Gly Ser Ser Asp Leu Trp Val Phe Ser Ser Glu Thr Pro Lys
        115                 120                 125

Ser Ser Ala Thr Gly His Ala Ile Tyr Thr Pro Ser Lys Ser Ser Thr
    130                 135                 140

Ser Lys Lys Val Ser Gly Ala Ser Trp Ser Ile Ser Tyr Gly Asp Gly
145                 150                 155                 160

Ser Ser Ser Ser Gly Asp Val Tyr Thr Asp Lys Val Thr Ile Gly Gly
                165                 170                 175

Phe Ser Val Asn Thr Gln Gly Val Glu Ser Ala Thr Arg Val Ser Thr
            180                 185                 190

Glu Phe Val Gln Asp Thr Val Ile Ser Gly Leu Val Gly Leu Ala Phe
        195                 200                 205

Asp Ser Gly Asn Gln Val Arg Pro His Pro Gln Lys Thr Trp Phe Ser
    210                 215                 220

Asn Ala Ala Ser Ser Leu Ala Glu Pro Leu Phe Thr Ala Asp Leu Arg
225                 230                 235                 240

His Gly Gln Asn Gly Ser Tyr Asn Phe Gly Tyr Ile Asp Thr Ser Val
```

```
                245                 250                 255
Ala Lys Gly Pro Val Ala Tyr Thr Pro Val Asp Asn Ser Gln Gly Phe
            260                 265                 270

Trp Glu Phe Thr Ala Ser Gly Tyr Ser Val Gly Gly Lys Leu Asn
        275                 280                 285

Arg Asn Ser Ile Asp Gly Ile Ala Asp Thr Gly Thr Thr Leu Leu Leu
    290                 295                 300

Leu Asp Asp Asn Val Val Asp Ala Tyr Tyr Ala Asn Val Gln Ser Ala
305                 310                 315                 320

Gln Tyr Asp Asn Gln Gln Glu Gly Val Val Phe Asp Cys Asp Glu Asp
                325                 330                 335

Leu Pro Ser Phe Ser Phe Gly Val Gly Ser Ser Thr Ile Thr Ile Pro
            340                 345                 350

Gly Asp Leu Leu Asn Leu Thr Pro Leu Glu Glu Gly Ser Ser Thr Cys
        355                 360                 365

Phe Gly Gly Leu Gln Ser Ser Ser Gly Ile Gly Ile Asn Ile Phe Gly
    370                 375                 380

Asp Val Ala Leu Lys Ala Ala Leu Val Val Phe Asp Leu Gly Asn Glu
385                 390                 395                 400

Arg Leu Gly Trp Ala Gln Lys
                405

<210> SEQ ID NO 3
<211> LENGTH: 1347
<212> TYPE: DNA
<213> ORGANISM: Artificial Sequence
<220> FEATURE:
<223> OTHER INFORMATION: synthetic pepA nucleotide

<400> SEQUENCE: 3
atggtcgtct tcagcaaaac cgctgccctc gttctgggtc tgtcctccgc cgtctctgcg     60
gcgccggctc ctactcgcaa gggcttcacc atcaaccaga ttgcccggcc tgccaacaag    120
acccgcacca tcaacctgcc aggcatgtac gcccgttccc tggccaagtt tggcggtacg    180
gtgccccaga gcgtgaagga ggctgccagc aagggtagtg ccgtgaccac gccccagaac    240
aatgacgagg agtacctgac tcccgtcact gtcggaaagt ccacccctcca tctggacttt    300 gacaccggat ctgcagatct gtaagcttcc ctgctcgggt gttcgggcaa atcgtgacta    360
acctggacta gctgggtctt ctcggacgag ctcccttcct cggagcagac cggtcacgat    420
ctgtacacgc ctagctccag cgcgaccaag ctgagcggct acacttggga catctcctac    480
ggtgacggca gctcggccag cggagacgtg taccgggata ctgtcactgt cggcggtgtc    540
accaccaaca agcaggctgt tgaagcagcc agcaagatca gctccgagtt cgttcagaac    600
acggccaatg acggcctttt gggactggcc tttagctcca tcaacactgg tgagtcaatc    660
ctacatcagc cggttgacc tacctgctga ccgatacaca gtccagccca aggcgcagac    720
caccttcttc gacaccgtca gtcccagct ggactctccc cttttcgccg tgcagctgaa    780
gcacgacgcc cccggtgttt acgactttgg ctacatcgat gactccaagt acaccggttc    840
tatcacctac acggatgccg atagctccca gggttactgg ggcttcagca ccgacggcta    900
cagtatcggt gacggcagct ccagctccag cggcttcagc gccattgctg gtaagaaccg    960
ccttcattta acacacaact tgtccacctc tttactaact agtgtataga caccggtacc    1020
accctcatcc tcctcgatga cgaaatcgtc tccgcctact acgagcaggt ttctggcgct    1080
caggagagcg aggaagccgg tggctacgtt ttctcttgct cgaccaaccc ccctgacttc    1140
```

-continued

| actgtcgtga ttggcgacta caaggccgtt gttccgggca agtacatcaa ctacgctccc | 1200 |
| atctcgactg gcagctccac ctgctttggc ggtatccaga gcaacagcgg tctgggactg | 1260 |
| tccatcctgg gtgatgtttt cttgaagagc cagtacgtgg tcttcaactc tgagggccct | 1320 |
| aagctgggat tcgccgctca ggcttag | 1347 |

<210> SEQ ID NO 4
<211> LENGTH: 1199
<212> TYPE: DNA
<213> ORGANISM: Artificial Sequence
<220> FEATURE:
<223> OTHER INFORMATION: synthetic NSP25 nucleotide

<400> SEQUENCE: 4

| atgcagccct catttggcag cttcctcgtc accgtcctgt ctgcctccat ggcagcaggc | 60 |
| agtgtcattc ccagcacaaa cgccaaccct ggctccttcg agatcaagag atccgccaac | 120 |
| aaagccttca caggccgcaa tggccctcta gcattagccc gtacatacgc caagtacggt | 180 |
| gttgaagtcc ccaaaactct ggtcgatgct attcaactcg tcaagtccat ccagctcgca | 240 |
| aagcgggaca cgccaccgt cactgccacg ccggaccacg acgacatcga gtatcttgtc | 300 |
| cccgtcaaga tcggaactcc tccccaaaca cttaacctgg attttgacac gggcagctcc | 360 |
| gatctctggg tcttctcatc agatgtcgac ccgacctcct cccagggcca tgacatctac | 420 |
| accccgtcca agagcacatc ttccaaaaag ttggaaggag cctcatggaa catcacatat | 480 |
| ggagaccgct catcatcatc cggcgatgtc taccacgata ttgtctccgt cggaaacctg | 540 |
| acagtaaagt cccaagccgt cgagtccgct cgaaacgtct cggccagttc acccagggca | 600 |
| acaacgacgg cctcgtcggc ctggcgttta gctccatcaa cacagtcaag cccacgccgc | 660 |
| aaaagacgtg gtacgacaac atcgtcggca gccttgactc tcccgtcttt gttgctgatc | 720 |
| tgcgccacga cacgcccggc agctaccact tcggctccat cccctccgaa gcaagcaaag | 780 |
| ccttctacgc cccatcgac aacagcaagg gcttctggca attcagcacg agcagcaaca | 840 |
| ttagcggcca gttcaacgcc gttgcagaca ctggcactac tctgctgctc gccagcgacg | 900 |
| acctcgtcaa ggcctactac gcaaaggtcc agggcgcccg tgtgaacgtc ttcctgggcg | 960 |
| gctacgtctt caactgcacc actcagctgc ccgactttac ctttactgtt ggagagggca | 1020 |
| acatcactgt ccccggtacc ttgataaact attccgaggc tggcaacggc cagtgttttg | 1080 |
| gcggtattca gccgtcgggg ggtcttcctt ttgctatctt tggtgacatt gctcttaagg | 1140 |
| ctgcgtatgt tattttgac agtggcaaca agcaggttgg ctgggcgcag aagaaatag | 1199 |

<210> SEQ ID NO 5
<211> LENGTH: 1347
<212> TYPE: DNA
<213> ORGANISM: Artificial Sequence
<220> FEATURE:
<223> OTHER INFORMATION: synthetic L388M pepA variant nucleotide

<400> SEQUENCE: 5

| atggtcgtct tcagcaaaac cgctgccctc gttctgggtc tgtcctccgc cgtctctgcg | 60 |
| gcgccggctc ctactcgcaa gggcttcacc atcaaccaga ttgcccggcc tgccaacaag | 120 |
| acccgcacca tcaacctgcc aggcatgtac gcccgttccc tggccaagtt tggcggtacg | 180 |
| gtgccccaga gcgtgaagga ggctgccagc aagggtagtg ccgtgaccac gccccagaac | 240 |
| aatgacgagg agtacctgac tcccgtcact gtcggaaagt ccaccctcca tctggacttt | 300 |
| gacaccggat ctgcagatct gtaagcttcc ctgctcgggt gttcgggcaa atcgtgacta | 360 |

| | |
|---|---|
| acctggacta gctgggtctt ctcggacgag ctcccttcct cggagcagac cggtcacgat | 420 |
| ctgtacacgc ctagctccag cgcgaccaag ctgagcggct acacttggga catctcctac | 480 |
| ggtgacggca gctcggccag cggagacgtg taccgggata ctgtcactgt cggcggtgtc | 540 |
| accaccaaca agcaggctgt tgaagcagcc agcaagatca gctccgagtt cgttcagaac | 600 |
| acggccaatg acggccttt gggactggcc tttagctcca tcaacactgg tgagtcaatc | 660 |
| ctacatcagc cggttgacc tacctgctga ccgatacaca gtccagccca aggcgcagac | 720 |
| caccttcttc gacaccgtca gtcccagct ggactctccc cttttcgccg tgcagctgaa | 780 |
| gcacgacgcc cccggtgttt acgactttgg ctacatcgat gactccaagt acaccggttc | 840 |
| tatcacctac acggatgccg atagctccca gggttactgg ggcttcagca ccgacggcta | 900 |
| cagtatcggt gacggcagct ccagctccag cggcttcagc gccattgctg gtaagaaccg | 960 |
| ccttcattta acacacaact tgtccacctc tttactaact agtgtataga caccggtacc | 1020 |
| accctcatcc tcctcgatga cgaaatcgtc tccgcctact acgagcaggt ttctggcgct | 1080 |
| caggagagcg aggaagccgg tggctacgtt ttctcttgct cgaccaaccc ccctgacttc | 1140 |
| actgtcgtga ttggcgacta caaggccgtt gttccgggca agtacatcaa ctacgctccc | 1200 |
| atctcgactg gcagctccac ctgctttggc ggtatccaga gcaacagcgg tctgggactg | 1260 |
| tccatcctgg gtgatgtttt cttgaagagc cagtacgtgg tcttcaactc tgagggccct | 1320 |
| aagatgggat tcgccgctca ggcttag | 1347 |

<210> SEQ ID NO 6
<211> LENGTH: 10286
<212> TYPE: DNA
<213> ORGANISM: Artificial Sequence
<220> FEATURE:
<223> OTHER INFORMATION: synthetic pSL899_pepA plasmid

<400> SEQUENCE: 6

| | |
|---|---|
| tacgtatttt gaatagctcg cccgctggag agcatcctga atgcaagtaa caaccgtaga | 60 |
| ggctgacacg gcaggtgttg ctagggagcg tcgtgttcta caaggccaga cgtcttcgcg | 120 |
| gttgatatat atgtatgttt gactgcaggc tgctcagcga cgacagtcaa gttcgccctc | 180 |
| gctgcttgtg caataatcgc agtggggaag ccacaccgtg actcccatct ttcagtaaag | 240 |
| ctctgttggt gtttatcagc aatacacgta atttaaactc gttagcatgg ggctgatagc | 300 |
| ttaattaccg tttaccagtg ccgcggttct gcagctttcc ttggcccgta aaattcggcg | 360 |
| aagccagcca atcaccagct aggcaccagc taaaccctat aattagtctc ttatcaacac | 420 |
| catccgctcc cccgggatca atgaggagaa tgaggggat gcggggctaa agaagcctac | 480 |
| ataaccctca tgccaactcc cagtttacac tcgtcgagcc aacatcctga ctataagcta | 540 |
| acacagaatg cctcaatcct gggaagaact ggccgctgat aagcgcgccc gcctcgcaaa | 600 |
| aaccatccct gatgaatgga agtccgacc gctgcctgcg gaagacagcg ttattgatt | 660 |
| cccaaagaaa tcggggatcc tttcagaggc cgaactgaag atcacagagg cctccgctgc | 720 |
| agatcttgtg tccaagctgg cggccggaga gttgacctcg gtggaagtta cgctagcatt | 780 |
| ctgtaaacgg gcagcaatcg cccagcagtt agtagggtcc cctctacctc tcagggagat | 840 |
| gtaacaacgc caccttatgg gactatcaag ctgacgctgg cttctgtgca gacaaactgc | 900 |
| gcccacgagt tcttccctga cgccgctctc gcgcaggcaa gggaactcga tgaatactac | 960 |
| gcaaagcaca agagacccgt tggtccactc catggcctcc ccatctctct caaagaccag | 1020 |
| cttcgagtca aggtacaccg ttgcccctaa gtcgttagat gtcccttttt gtcagctaac | 1080 |

```
atatgccacc agggctacga aacatcaatg ggctacatct catggctaaa caagtacgac    1140
gaaggggact cggttctgac aaccatgctc cgcaaagccg gtgccgtctt ctacgtcaag    1200
acctctgtcc cgcagaccct gatggtctgc gagacagtca acaacatcat cgggcgcacc    1260
gtcaacccac gcaacaagaa ctggtcgtgc ggcggcagtt ctggtggtga gggtgcgatc    1320
gttgggattc gtggtggcgt catcggtgta ggaacggata tcggtggctc gattcgagtg    1380
ccggccgcgt tcaacttcct gtacggtcta aggccgagtc atgggcggct gccgtatgca    1440
aagatggcga acagcatgga gggtcaggag acggtgcaca gcgttgtcgg gccgattacg    1500
cactctgttg agggtgagtc cttcgcctct tccttctttt cctgctctat accaggcctc    1560
cactgtcctc ctttcttgct ttttatacta tatacgagac cggcagtcac tgatgaagta    1620
tgttagacct ccgcctcttc accaaatccg tcctcggtca ggagccatgg aaatacgact    1680
ccaaggtcat ccccatgccc tggcgccagt ccgagtcgga cattattgcc tccaagatca    1740
agaacggcgg gctcaatatc ggctactaca acttcgacgg caatgtcctt ccacaccctc    1800
ctatcctgcg cggcgtggaa accaccgtcg ccgcactcgc caaagccggt cacaccgtga    1860
ccccgtggac gccatacaag cacgatttcg gccacgatct catctcccat atctacgcgg    1920
ctgacggcag cgccgacgta atgcgcgata tcagtgcatc cggcgagccg gcgattccaa    1980
atatcaaaga cctactgaac ccgaacatca aagctgttaa catgaacgag ctctgggaca    2040
cgcatctcca gaagtggaat taccagatgg agtaccttga gaaatggcgg gaggctgaag    2100
aaaaggccgg gaaggaactg gacgccatca tcgcgccgat tacgcctacc gctgcggtac    2160
ggcatgacca gttccggtac tatgggtatg cctctgtgat caacctgctg gatttcacga    2220
gcgtggttgt tccggttacc tttgcggata agaacatcga taagaagaat gagagtttca    2280
aggcggttag tgagcttgat gccctcgtgc aggaagagta tgatccggag cgtaccatg     2340 gggcaccggt tgcagtgcag gttatcggac ggagactcag tgaagagagg acgttggcga    2400
ttgcagagga agtggggaag ttgctgggaa atgtggtgac tccatagcta ataagtgtca    2460
gatagcaatt tgcacaagaa atcaatacca gcaactgtaa ataagcgctg aagtgaccat    2520
gccatgctac gaaagagcag aaaaaaacct gccgtagaac cgaagagata tgacacgctt    2580
ccatctctca aaggaagaat cccttcaggg ttgcgtttcc agtctagcta gagtcgagga    2640
ttgcctgaac attgacattc ggcgtccggc cgggaccacc gcggactcga agctgcctgt    2700
gctggtctgg atctttggcg gaggctttga acttggttca aaggcgatgt atgatggtac    2760
aacgatggta tcatcgtcga tagacaagaa catgcctatc gtgtttgtag caatgaatta    2820
tcgcgtggga ggtttcgggt tcttgcccgg aaaggagatc ctggaggacg ggtccgcgaa    2880
cctagggctc ctggaccaac gccttgccct gcagtgggtt gccgacaaca tcgaggcctt    2940
tggtggagac ccggacaagg tgacgatttg gggagaatca gcaggagcca tttccgtttt    3000
tgatcagatg atcttgtacg acggaaacat cacttacaag gataagcect tgttccgggg    3060 ggccatcatg gactccggta gtgttgttcc cgcagacccc gtcgatgggg tcaagggaca    3120
gcaagtatat gatgcggtag tggaatctgc aggctgttcc tcttctaacg acaccctagc    3180
ttgtctgcgt gaactagact acaccgactt cctcaatgcg gcaaactccg tgccaggcat    3240
tttaagctac cattctgtgg cgttatcata tgtgcctcga ccggacggga cggcgttgtc    3300
ggcatcaccg gacgttttgg gcaaagcagg gaaatatgct cgggtcccgt tcatcgtggg    3360
cgaccaagag gatgagggga ccttattcgc cttgtttcag tccaacatta cgacgatcga    3420
cgaggtggtc gactacctgg cctcatactt cttctatgac gctagccgag agcagcttga    3480
```

```
agaactagtg gccctgtacc cagacaccac cacgtacggg tctccgttca ggacaggcgc   3540
ggccaacaac tggtatccgc aatttaagcg attggccgcc attctcggcg acttggtctt   3600
caccattacc cggcgggcat tcctctcgta tgcagaggaa atctcccctg atcttccgaa   3660
ctggtcgtac ctggcgacct atgactatgg cacccagtt ctggggacct tccacggaag    3720
tgacctgctg caggtgttct atgggatcaa gccaaactat gcagctagtt ctagccacac   3780
gtactatctg agctttgtgt atacgctgga tccgaactcc aaccgggggg agtacattga   3840
gtggccgcag tggaaggaat cgcggcagtt gatgaatttc ggagcgaacg acgccagtct   3900
ccttacggat gatttccgca acgggacata tgagttcatc ctgcagaata ccgcggcgtt   3960
ccacatctga tgccattggc ggaggggtcc ggacggtcag gaacttagcc ttatgagatg   4020
aatgatggac gtgtctggcc tcggaaaagg atatatgggg atcatgatag tactagccat   4080
attaatgaag ggcatatacc acgcgttgga cctgcgttat agcttcccgt tagttatagt   4140
accatcgtta taccagccaa tcaagtcacc acgcacgacc ggggacgcg aatccccggg     4200 aattgaaaga aattgcatcc caggccagtg aggccagcga ttggccacct ctccaaggca   4260
cagggccatt ctgcagcgct ggtggattca tcgcaatttc ccccggcccg cccgacacc    4320 gctataggct ggttctccca caccatcgga gattcgtcgc ctaatgtctc gtccgttcac   4380
aagctgaaga gcttgaagtg gcgagatgtc tctgcaggaa ttcaagctag atgctaagcg   4440
atattgcatg gcaatatgtg ttgatgcatg tgcttcttcc ttcagcttcc cctcgtgcag   4500
atgaggtttg gctataaatt gaagtggttg gtcggggttc cgtgagggc tgaagtgctt     4560 cctcccttt agacgcaact gagagcctga gcttcatccc cagcatcatt acacctcgag    4620
atggtcgtct tcagcaaaac cgctgccctc gttctgggtc tgtcctccgc cgtctctgcg   4680
gcgccggctc ctactcgcaa gggcttcacc atcaaccaga ttgcccggcc tgccaacaag   4740
acccgcacca tcaacctgcc aggcatgtac gcccgttccc tggccaagtt tggcggtacg   4800
gtgccccaga gcgtgaagga ggctgccagc aagggtagtg ccgtgaccac gccccagaac   4860
aatgacgagg agtacctgac tcccgtcact gtcggaaagt ccaccctcca tctggacttt    4920
gacaccggat ctgcagatct gtaagcttcc ctgctcgggt gttcgggcaa atcgtgacta    4980
acctggacta gctgggtctt ctcggacgag ctcccttcct cggagcagac cggtcacgat   5040
ctgtacacgc ctagctccag cgcgaccaag ctgagcggct acacttggga catctcctac   5100
ggtgacggca gctcggccag cggagacgtg taccgggata ctgtcactgt cggcggtgtc    5160
accaccaaca agcaggctgt tgaagcagcc agcaagatca gctccgagtt cgttcagaac   5220
acggccaatg acggccttt gggactggcc tttagctcca tcaacactgg tgagtcaatc    5280
ctacatcagc cggttgacc tacctgctga ccgatacaca gtccagccca aggcgcagac    5340
caccttcttc gacaccgtca gtcccagct ggactctccc cttttcgccg tgcagctgaa     5400
gcacgacgcc cccggtgttt acgactttgg ctacatcgat gactccaagt acaccggttc   5460
tatcacctac acggatgccg atagctccca gggttactgg gcttcagca ccgacggcta    5520 cagtatcggt gacggcagct ccagctccag cggcttcagc gccattgctg gtaagaaccg   5580
ccttcattta acacacaact tgtccacctc tttactaact agtgtataga caccggtacc   5640 acctcatcc tcctcgatga cgaaatcgtc tccgcctact acgagcaggt ttctggcgct    5700
caggagagcg aggaagccgg tggctacgtt ttctcttgct cgaccaaccc ccctgacttc    5760
actgtcgtga ttggcgacta caaggccgtt gttccgggca agtacatcaa ctacgctccc   5820
atctcgactg gcagctccac ctgctttggc ggtatccaga gcaacagcgg tctgggactg   5880
```

```
tccatcctgg gtgatgtttt cttgaagagc cagtacgtgg tcttcaactc tgagggccct    5940
aagctgggat tcgccgctca ggcttagtct agagtcgacc gcgacggtga ccgacacctg    6000
gcggtagact atttattcct gttgatatga aggatgagca tgagggtaat tgctcatata    6060
atcatgtatg tagtggatgt gcataagagc aacgaaatgg aagcctgatc atgtgattgt    6120
attgcgaccg acggaattga ggatatgcgg agatacggac agtgccagag ccattgtctt    6180
cacgtaaagt accagacggt ccctgatttc ttcttgcaca tagcattagg caattgacat    6240
gttgtcgctc tactgatatc actgtccctc aaagcatagc catgagctca tcttagatcc    6300
aagcacgtaa ttccatagcc gaggtccaca gtggagcaac agcagcatcc atcattgctt    6360
ctcccccagg ggcctcttag cgactaaacc tggagtatgt ctcaaccagc caatgaatcg    6420
tcttcgcttc aatgtccttg acacttctga gagggtcccc atccctcaat gctaattcaa    6480
aatatagccg agatgcatgg tggagtccaa agtagacagt attgccggaa tgacggggcc    6540
agttgcgccg aggtcattgg ccggctgtga tgccatctgc cactaaatcc gatcattgat    6600
ccaccgccca cgagggccgt cttttgctttt gcgctgcgtc caggttcaca catctctctc    6660
tctgcagctc cagactgacc agactattct acttactggt ctgatcggct ccatcagagc    6720
tatggcgtta tcccgtgccg ttgctgcgcc atcgctatct gatcgcgag ctcgaactca    6780 cttcttgttt taatagttgt tctcggtgac tgagtgtcgg tgagtgacag accacaacac    6840
cattgttgca gggggtaaat ttattcaatt caggaattgg attgttcgtc ccgccatgat    6900
gttcttgccg gctttgttgg ccctgtttgt cggatgcgac gccctcgctg tgcagcaggc    6960
aggtactgct ggatgatgag ccgtcggtct ccgcgcgcaa gcctaacttc ctcttcattc    7020
ttacggatga tcaggatctg cagatcgaat tccaccggcg tatatgccgt atacacaggc    7080
gagaatcaag gagaagggta ctgagttttg aatcatttgt tactactggc tctgtgctgt    7140
ccgtcgcgcg tgagtctttg gacggaagac aggctcataa tactaatgtg acggatgtga    7200
acccgcctta tggtatgaat acctctcaga tcggtcatgt ttcttcggtg taaaattgct    7260
aatgcagcat aggcggatac cccaagttcg tcgcccaagg cttcaacgaa aacttcctcc    7320
ccgtttggct gcagtccgcc ggttacaata ccttctacac ggggaaactg ttcaactgcc    7380
acagcgtcgc tacctataat gcaccgtttg tgaacggctt caatggctct gatttcctcc    7440
tcgatcccca cacctattcc tactggaacg cgacgtacca acgaaaccat gagcctccgc    7500
ggagctacga gggacaatac acaacggatg tgatgcggga aaggcatcg gggttgttgg    7560 cagatgcgct ggacaggacg cgccgttctt ctgacggtgc ctatccgccg cacacgaaca    7620
tcgacctgca ggcatgcaag cttggcactg gccgtcgttt tacaacgtcg tgactgggaa    7680
aaccctggcg ttacccaact taatcgcctt gcagcacatc cccctttcgc cagctggcgt    7740
aatagcgaag aggcccgcac cgatcgccct tcccaacagt tgcgcagcct gaatggcgaa    7800
tggcgcctga tgcggtattt tctccttacg catctgtgcg gtatttcaca ccgcatatgg    7860
tgcactctca gtacaatctg ctctgatgcc gcatagttaa gccagccccg acacccgcca    7920
acacccgctg acgcgccctg acgggcttgt ctgctcccgg catccgctta cagacaagct    7980
gtgaccgtct ccgggagctg catgtgtcag aggttttcac cgtcatcacc gaaacgcgcg    8040
agacgaaagg gcctcgtgat acgcctattt ttataggtta atgtcatgat aataatggtt    8100
tcttagacgt caggtggcac ttttcgggga atgtgcgcg gaacccctat ttgtttattt    8160
ttctaaatac attcaaatat gtatccgctc atgagacaat aaccctgata aatgcttcaa    8220
taatattgaa aaaggaagag tatgagtatt caacatttcc gtgtcgccct tattcccttt    8280
```

```
tttgcggcat tttgccttcc tgttttgct cacccagaaa cgctggtgaa agtaaaagat    8340
gctgaagatc agttgggtgc acgagtgggt tacatcgaac tggatctcaa cagcggtaag    8400
atccttgaga gttttcgccc cgaagaacgt tttccaatga tgagcacttt taaagttctg    8460
ctatgtggcg cggtattatc ccgtattgac gccgggcaag agcaactcgg tcgccgcata    8520
cactattctc agaatgactt ggttgagtac tcaccagtca cagaaaagca tcttacggat    8580
ggcatgacag taagagaatt atgcagtgct gccataacca tgagtgataa cactgcggcc    8640
aacttacttc tgacaacgat cggaggaccg aaggagctaa ccgcttttt gcacaacatg    8700
ggggatcatg taactcgcct tgatcgttgg gaaccggagc tgaatgaagc cataccaaac    8760
gacgagcgtg acaccacgat gcctgtagca atggcaacaa cgttgcgcaa actattaact    8820
ggcgaactac ttactctagc ttcccggcaa caattaatag actggatgga ggcggataaa    8880
gttgcaggac cacttctgcg ctcggccctt ccggctggct ggtttattgc tgataaatct    8940
ggagccggtg agcgtgggtc tcgcggtatc attgcagcac tggggccaga tggtaagccc    9000
tcccgtatcg tagttatcta cacgacgggg agtcaggcaa ctatggatga acgaaataga    9060
cagatcgctg agataggtgc ctcactgatt aagcattggt aactgtcaga ccaagtttac    9120
tcatatatac tttagattga tttaaaactt catttttaat ttaaaaggat ctaggtgaag    9180
atccttttg ataatctcat gaccaaaatc ccttaacgtg agttttcgtt ccactgagcg    9240
tcagacccg tagaaaagat caaaggatct tcttgagatc cttttttct gcgcgtaatc    9300
tgctgcttgc aaacaaaaaa accaccgcta ccagcggtgg tttgtttgcc ggatcaagag    9360
ctaccaactc ttttccgaa ggtaactggc ttcagcagag cgcagatacc aaatactgtc    9420
cttctagtgt agccgtagtt aggccaccac ttcaagaact ctgtagcacc gcctacatac    9480
ctcgctctgc taatcctgtt accagtggct gctgccagtg cgataagtc gtgtcttacc    9540
gggttggact caagacgata gttaccggat aaggcgcagc ggtcgggctg aacggggggt    9600
tcgtgcacac agcccagctt ggagcgaacg acctacaccg aactgagata cctacagcgt    9660
gagctatgag aaagcgccac gcttcccgaa gggagaaagg cggacaggta tccggtaagc    9720
ggcagggtcg gaacaggaga gcgcacgagg gagcttccag ggggaaacgc ctggtatctt    9780
tatagtcctg tcgggtttcg ccacctctga cttgagcgtc gatttttgtg atgctcgtca    9840
ggggggcgga gcctatggaa aaacgccagc aacgcggcct ttttacggtt cctggccttt    9900
tgctggcctt ttgctcacat gttctttcct gcgttatccc ctgattctgt ggataaccgt    9960
attaccgcct ttgagtgagc tgataccgct cgccgcagcc gaacgaccga gcgcagcgag   10020
tcagtgagcg aggaagcgga agagcgccca atacgcaaac cgcctctccc cgcgcgttgg   10080
ccgattcatt aatgcagctg gcacgacagg tttcccgact ggaaagcggg cagtgagcgc   10140
aacgcaatta atgtgagtta gctcactcat taggcacccc aggctttaca ctttatgctt   10200
ccggctcgta tgttgtgtgg aattgtgagc ggataacaat ttcacacagg aaacagctat   10260
gaccatgatt acgaattcga gctcgg                                        10286
```

<210> SEQ ID NO 7
<211> LENGTH: 394
<212> TYPE: PRT
<213> ORGANISM: Artificial Sequence
<220> FEATURE:
<223> OTHER INFORMATION: synthetic L388M pepA variant peptide

<400> SEQUENCE: 7

```
Met Val Val Phe Ser Lys Thr Ala Ala Leu Val Leu Gly Leu Ser Ser
1               5                   10                  15
```

Ala Val Ser Ala Ala Pro Ala Pro Thr Arg Lys Gly Phe Thr Ile Asn
            20                  25                  30

Gln Ile Ala Arg Pro Ala Asn Lys Thr Arg Thr Ile Asn Leu Pro Gly
            35                  40                  45

Met Tyr Ala Arg Ser Leu Ala Lys Phe Gly Gly Thr Val Pro Gln Ser
 50                  55                  60

Val Lys Glu Ala Ala Ser Lys Gly Ser Ala Val Thr Thr Pro Gln Asn
 65                  70                  75                  80

Asn Asp Glu Glu Tyr Leu Thr Pro Val Thr Val Gly Lys Ser Thr Leu
                85                  90                  95

His Leu Asp Phe Asp Thr Gly Ser Ala Asp Leu Trp Val Phe Ser Asp
               100                 105                 110

Glu Leu Pro Ser Ser Glu Gln Thr Gly His Asp Leu Tyr Thr Pro Ser
           115                 120                 125

Ser Ser Ala Thr Lys Leu Ser Gly Tyr Thr Trp Asp Ile Ser Tyr Gly
       130                 135                 140

Asp Gly Ser Ser Ala Ser Gly Asp Val Tyr Arg Asp Thr Val Thr Val
145                 150                 155                 160

Gly Gly Val Thr Thr Asn Lys Gln Ala Val Glu Ala Ala Ser Lys Ile
                165                 170                 175

Ser Ser Glu Phe Val Gln Asn Thr Ala Asn Asp Gly Leu Leu Gly Leu
           180                 185                 190

Ala Phe Ser Ser Ile Asn Thr Val Gln Pro Lys Ala Gln Thr Thr Phe
       195                 200                 205

Phe Asp Thr Val Lys Ser Gln Leu Asp Ser Pro Leu Phe Ala Val Gln
210                 215                 220

Leu Lys His Asp Ala Pro Gly Val Tyr Asp Phe Gly Tyr Ile Asp Asp
225                 230                 235                 240

Ser Lys Tyr Thr Gly Ser Ile Thr Tyr Thr Asp Ala Asp Ser Ser Gln
                245                 250                 255

Gly Tyr Trp Gly Phe Ser Thr Asp Gly Tyr Ser Ile Gly Asp Gly Ser
           260                 265                 270

Ser Ser Ser Ser Gly Phe Ser Ala Ile Ala Asp Thr Gly Thr Thr Leu
       275                 280                 285

Ile Leu Leu Asp Asp Glu Ile Val Ser Ala Tyr Tyr Glu Gln Val Ser
290                 295                 300

Gly Ala Ser Gly Glu Thr Glu Ala Gly Gly Tyr Val Phe Ser Cys Ser
305                 310                 315                 320

Thr Asn Pro Pro Asp Phe Thr Val Val Ile Gly Asp Tyr Lys Ala Val
                325                 330                 335

Val Pro Gly Lys Tyr Ile Asn Tyr Ala Pro Ile Ser Thr Gly Ser Ser
           340                 345                 350

Thr Cys Phe Gly Gly Ile Gln Ser Asn Ser Gly Leu Gly Leu Ser Ile
       355                 360                 365

Leu Gly Asp Val Phe Leu Lys Ser Gln Tyr Val Val Phe Asn Ser Glu
370                 375                 380

Gly Pro Lys Met Gly Phe Ala Ala Gln Ala
385                 390

<210> SEQ ID NO 8
<211> LENGTH: 1302
<212> TYPE: DNA
<213> ORGANISM: Trichoderma reesei

<400> SEQUENCE: 8

```
atgcagacct tggagctttt tctcgtttcc ttcctcgccg ccagcggcct ggccgcggcc      60
ctccccaccg agggtcagaa gacggcttcc gtcgaggtcc agtacaacaa gaactacgtc     120
ccccacggcc ctactgctct cttcaaggcc aagagaaagt atggcgctcc catcagcgac     180
aacctgaagt ctctcgtggc tgccaggcag gccaagcagg ctctcgccaa gcgccagacc     240
ggctcggcgc ccaaccaccc cagtgacagc gccgattcgg agtacatcac ctccgtctcc     300
atcggcactc cggctcaggt cctcccctg  gactttgaca ccggctcctc cgacctgtgg     360
gtctttagct ccgagacgcc caagtcttcg gccaccggcc acgccatcta cacgccctcc     420
aagtcgtcca cctccaagaa ggtgtctggc gccagctggt ccatcagcta cggcgacggc     480
agcagctcca gcggcgatgt ctacaccgac aaggtcacca tcggaggctt cagcgtcaac     540
acccagggcg tcgagtctgc cacccgcgtg tccaccgagt tcgtccagga cacggtcatc     600
tctggcctcg tcggccttgc ctttgacagc ggcaaccagg tcaggccgca cccgcagaag     660
acgtggttct ccaacgccgc cagcagcctg gctgagcccc ttttcactgc cgacctgagg     720
cacggacaga gtaagtagac actcactgga attcgttcct ttcccgatca tcatgaaagc     780
aagtagactg actgaaccaa caactagacg gcagctaca  actttggcta catcgacacc     840
agcgtcgcca agggccccgt tgcctacacc cccgttgaca cagccaggg  cttctgggag     900
ttcactgcct cgggctactc tgtcggcggc ggcaagctca accgcaactc catcgacggc     960
attgccgaca ccggcaccac cctgctcctc ctcgacgaca acgtcgtcga tgcctactac    1020
gccaacgtcc agtcggccca gtacgacaac cagcaggagg gtgtcgtctt cgactgcgac    1080
gaggacctcc cttcgttcag cttcggtgtt ggaagctcca ccatcaccat ccctggcgat    1140
ctgctgaacc tgactcccct cgaggagggc agctccacct gcttcggtgg cctccagagc    1200
agctccggca ttggcatcaa catctttggt gacgttgccc tcaaggctgc cctggttgtc    1260
tttgacctcg gcaacgagcg cctgggctgg gctcagaaat aa                       1302
```

<210> SEQ ID NO 9
<211> LENGTH: 399
<212> TYPE: PRT
<213> ORGANISM: Artificial Sequence
<220> FEATURE:
<223> OTHER INFORMATION: synthetic NSP25 peptide
<220> FEATURE:
<221> NAME/KEY: misc_feature
<222> LOCATION: (195)..(195)
<223> OTHER INFORMATION: Xaa can be any naturally occurring amino acid

<400> SEQUENCE: 9

```
Met Gln Pro Ser Phe Gly Ser Phe Leu Val Thr Val Leu Ser Ala Ser
1               5                   10                  15

Met Ala Ala Gly Ser Val Ile Pro Ser Thr Asn Ala Asn Pro Gly Ser
            20                  25                  30

Phe Glu Ile Lys Arg Ser Ala Asn Lys Ala Phe Thr Gly Arg Asn Gly
        35                  40                  45

Pro Leu Ala Leu Ala Arg Thr Tyr Ala Lys Tyr Gly Val Glu Val Pro
    50                  55                  60

Lys Thr Leu Val Asp Ala Ile Gln Leu Val Lys Ser Ile Gln Leu Ala
65                  70                  75                  80

Lys Arg Asp Ser Ala Thr Val Thr Ala Thr Pro Asp His Asp Ile
            85                  90                  95

Glu Tyr Leu Val Pro Val Lys Ile Gly Thr Pro Pro Gln Thr Leu Asn
            100                 105                 110
```

-continued

Leu Asp Phe Asp Thr Gly Ser Ser Asp Leu Trp Val Phe Ser Ser Asp
            115                 120                 125

Val Asp Pro Thr Ser Ser Gln Gly His Asp Ile Tyr Thr Pro Ser Lys
130                 135                 140

Ser Thr Ser Ser Lys Lys Leu Glu Gly Ala Ser Trp Asn Ile Thr Tyr
145                 150                 155                 160

Gly Asp Arg Ser Ser Ser Gly Asp Val Tyr His Asp Ile Val Ser
            165                 170                 175

Val Gly Asn Leu Thr Val Lys Ser Gln Ala Val Glu Ser Ala Arg Asn
                180                 185                 190

Val Ser Xaa Gln Phe Thr Gln Gly Asn Asn Asp Gly Leu Val Gly Leu
            195                 200                 205

Ala Phe Ser Ser Ile Asn Thr Val Lys Pro Thr Pro Gln Lys Thr Trp
210                 215                 220

Tyr Asp Asn Ile Val Gly Ser Leu Asp Ser Pro Val Phe Val Ala Asp
225                 230                 235                 240

Leu Arg His Asp Thr Pro Gly Ser Tyr His Phe Gly Ser Ile Pro Ser
            245                 250                 255

Glu Ala Ser Lys Ala Phe Tyr Ala Pro Ile Asp Asn Ser Lys Gly Phe
                260                 265                 270

Trp Gln Phe Ser Thr Ser Ser Asn Ile Ser Gly Gln Phe Asn Ala Val
            275                 280                 285

Ala Asp Thr Gly Thr Thr Leu Leu Leu Ala Ser Asp Asp Leu Val Lys
290                 295                 300

Ala Tyr Tyr Ala Lys Val Gln Gly Ala Arg Val Asn Val Phe Leu Gly
305                 310                 315                 320

Gly Tyr Val Phe Asn Cys Thr Thr Gln Leu Pro Asp Phe Thr Phe Thr
            325                 330                 335

Val Gly Glu Gly Asn Ile Thr Val Pro Gly Thr Leu Ile Asn Tyr Ser
                340                 345                 350

Glu Ala Gly Asn Gly Gln Cys Phe Gly Gly Ile Gln Pro Ser Gly Gly
            355                 360                 365

Leu Pro Phe Ala Ile Phe Gly Asp Ile Ala Leu Lys Ala Ala Tyr Val
    370                 375                 380

Ile Phe Asp Ser Gly Asn Lys Gln Val Gly Trp Ala Gln Lys Lys
385                 390                 395

<210> SEQ ID NO 10
<211> LENGTH: 355
<212> TYPE: PRT
<213> ORGANISM: Trichoderma reesei

<400> SEQUENCE: 10

Lys Tyr Gly Ala Pro Ile Ser Asp Asn Leu Lys Ser Leu Val Ala Ala
1               5                   10                  15

Arg Gln Ala Lys Gln Ala Leu Ala Lys Arg Gln Thr Gly Ser Ala Pro
            20                  25                  30

Asn His Pro Ser Asp Ser Ala Asp Ser Glu Tyr Ile Thr Ser Val Ser
        35                  40                  45

Ile Gly Thr Pro Ala Gln Val Leu Pro Leu Asp Phe Asp Thr Gly Ser
    50                  55                  60

Ser Asp Leu Trp Val Phe Ser Ser Glu Thr Pro Lys Ser Ser Ala Thr
65                  70                  75                  80

Gly His Ala Ile Tyr Thr Pro Ser Lys Ser Ser Thr Ser Lys Lys Val
                85                  90                  95

```
Ser Gly Ala Ser Trp Ser Ile Ser Tyr Gly Asp Gly Ser Ser Ser Ser
            100                 105                 110
Gly Asp Val Tyr Thr Asp Lys Val Thr Ile Gly Phe Ser Val Asn
            115                 120                 125
Thr Gln Gly Val Glu Ser Ala Thr Arg Val Ser Thr Glu Phe Val Gln
        130                 135                 140
Asp Thr Val Ile Ser Gly Leu Val Gly Leu Ala Phe Asp Ser Gly Asn
145                 150                 155                 160
Gln Val Arg Pro His Pro Gln Lys Thr Trp Phe Ser Asn Ala Ala Ser
            165                 170                 175
Ser Leu Ala Glu Pro Leu Phe Thr Ala Asp Leu Arg His Gly Gln Asn
            180                 185                 190
Gly Ser Tyr Asn Phe Gly Tyr Ile Asp Thr Ser Val Ala Lys Gly Pro
            195                 200                 205
Val Ala Tyr Thr Pro Val Asp Asn Ser Gln Gly Phe Trp Glu Phe Thr
        210                 215                 220
Ala Ser Gly Tyr Ser Val Gly Gly Lys Leu Asn Arg Asn Ser Ile
225                 230                 235                 240
Asp Gly Ile Ala Asp Thr Gly Thr Thr Leu Leu Leu Asp Asp Asn
            245                 250                 255
Val Val Asp Ala Tyr Tyr Ala Asn Val Gln Ser Ala Gln Tyr Asp Asn
        260                 265                 270
Gln Gln Glu Gly Val Val Phe Asp Cys Asp Glu Asp Leu Pro Ser Phe
    275                 280                 285
Ser Phe Gly Val Gly Ser Ser Thr Ile Thr Ile Pro Gly Asp Leu Leu
        290                 295                 300
Asn Leu Thr Pro Leu Glu Glu Gly Ser Ser Thr Cys Phe Gly Gly Leu
305                 310                 315                 320
Gln Ser Ser Ser Gly Ile Gly Ile Asn Ile Phe Gly Asp Val Ala Leu
            325                 330                 335
Lys Ala Ala Leu Val Val Phe Asp Leu Gly Asn Glu Arg Leu Gly Trp
            340                 345                 350
Ala Gln Lys
    355

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
caccatgcag acctttggag ct                                              22

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
ttatttctga gcccagccca g                                               21

<210> SEQ ID NO 13
<211> LENGTH: 24
<212> TYPE: DNA
<213> ORGANISM: Artificial Sequence
```

```
<220> FEATURE:
<223> OTHER INFORMATION: primer

<400> SEQUENCE: 13
caccatgcag ccctcatttg gcag                                              24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
ctatttcttc tgcgcccagc caac                                              24
```